(12) United States Patent
Stevens et al.

(10) Patent No.: US 8,450,479 B2
(45) Date of Patent: May 28, 2013

(54) 3-SUBSTITUTED-4-OXO-3,4-DIHYDRO-IMIDAZO[5,1-D][1,2,3,5-TETRAZINE-8-CARBOXYLIC ACID AMIDES AND THEIR USE

(75) Inventors: Malcolm Francis Graham Stevens, Loughborough (GB); David Cousin, Sneinton (GB); Sharon Jennings, Leicester (GB); Andrew James McCarroll, Sneinton (GB); John Gareth Williams, Nottingham (GB); Marc Geoffery Hummersone, Nottingham (GB); Jihong Zhang, Nottingham (GB)

(73) Assignee: Pharminox Limited, Nottingham (GB)

( * ) Notice: Subject to any disclaimer, the term of this patent is extended or adjusted under 35 U.S.C. 154(b) by 157 days.

(21) Appl. No.: 12/808,604

(22) PCT Filed: Dec. 16, 2008

(86) PCT No.: PCT/GB2008/004140
§ 371 (c)(1),
(2), (4) Date: Jun. 16, 2010

(87) PCT Pub. No.: WO2009/077741
PCT Pub. Date: Jun. 25, 2009

(65) Prior Publication Data
US 2010/0286088 A1 Nov. 11, 2010

Related U.S. Application Data

(60) Provisional application No. 61/014,520, filed on Dec. 18, 2007.

(51) Int. Cl.
| C07D 487/04 | (2006.01) |
| C07D 519/00 | (2006.01) |
| C07F 7/10 | (2006.01) |
| C07F 9/141 | (2006.01) |
| A61K 31/395 | (2006.01) |
| A61K 31/4188 | (2006.01) |
| A61P 35/00 | (2006.01) |

(52) U.S. Cl.
USPC ........................................... 544/179; 514/183

(58) Field of Classification Search
USPC .................................. 544/179; 514/183, 179
See application file for complete search history.

(56) References Cited

U.S. PATENT DOCUMENTS
| 4,504,475 | A | 3/1985 | Cheng |
| 5,260,291 | A | 11/1993 | Lunt et al. |
| 7,087,751 | B2 | 8/2006 | Kuo et al. |
| 2006/0047117 | A1 | 3/2006 | Wang et al. |
| 2012/0083513 | A1 | 4/2012 | Hummersone et al. |

FOREIGN PATENT DOCUMENTS
| FR | 2 511 679 A | 2/1983 |
| GB | 2 125 402 | 3/1984 |
| WO | WO 96/27588 | 9/1996 |
| WO | WO 2006/024238 | 3/2006 |
| WO | WO 2009/077741 | 6/2009 |
| WO | WO 2009/127815 | 10/2009 |
| WO | WO 2010/149968 | 12/2010 |

OTHER PUBLICATIONS

Cecil Textbook of Medicine, edited by Bennet, J.C., and Plum F., 20th edition,vol. 1, 1004-1010, 1996.*
West, Anthony R., Solid State Chemistry and its Applications, Wiley, New York, 1988, pp. 358 & 365.*
Vippagunta et al., Advanced Drug Delivery Reviews 48: 3-26, 2001.*
Wood et al., Current Opinion in Pharmacology, 1,370-377, 2001.*
Ruchelman et al., Biorganic & Medicinal Chemistry, 12, 795-806, 2004.*
Collins et al., Curr Opin Pharmacol. 5(4):366-73, 2005.*
Blain, S. W., Cell Cycle 7(7), 892-898, 2008.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Arrowsmith et al. (1999) "Antitumour imidazotetrazines Part 37", Anti-Cancer Drug Design, 14(3):205-217.
Arrowsmith et al. (2000) "Antitumour imidazotetrazines. Part 39.1 Synthesis of bis(imidazotetrazine)s with saturated spacer groups", J. Chem. Soc. Perkin Trans. 1, 24:4432-4438.
Arrowsmith et al. (2002) "Antitumor Imidazotetrazines. 41. Conjugation of the Antitumor Agents mitozolomide and Temozolomide to Peptides and Leitropsins Bearing DNA Major and Minor Groove-Binding Structural motifs", J. Med. Chem., 45:5458-5470.
Balba et al. (1968) "Synthesis of Possible Metabolites of Methylcarbamate Insecticide Chemicals", J. Agric. Food Chem., 16(5):821-825.
Bennett et al. (1957) "Synthesis of Potential Anticancer Agents. IV. 4-Nitro- and 4-Amino-5-imidazole Sulfones", J. Am. Chem. Soc., 79:2188-2191.
Berge et al. (1977) "Pharmaceutically Acceptable Salts", J. Pharm. Sci., 66:1-19.
Brown et al. (1999) "Apoptosis, p53 and tumor cell sensitivity to anticancer agents", Cancer Research, 59(7):1391-1399.
Brown et al. (2002) "Antitumor Imidazotetrazines. 40. Radiosyntheses of [4-IIC-Carbonyl]- and [3-N-IIC-Methyl]-8-carbamoyl-3-methylimidazo[5,1-d]-1,2,3,5-tetrazi n-4(3H)-one (Temozolomide) for Positron Emission Tomography (PET) Studies", J. Med. Chem., 45(25):5448-5457.

(Continued)

*Primary Examiner* — Venkataraman Balasubramanian
(74) *Attorney, Agent, or Firm* — Swanson & Bratschun, L.L.C.

(57) ABSTRACT

The present invention pertains generally to the field of therapeutic compounds, and more specifically to certain 3-substituted-4-oxo-3,4-dihydro-imidazo[5,1-d][1,2,3,5]tetrazine-8-carboxylic acid amide (collectively referred to herein as 3TM compounds). The present invention also pertains to pharmaceutical compositions comprising such compounds, and the use of such compounds and compositions, both in vitro and in vivo, to inhibit cell proliferation, and in the treatment of proliferative disorders such as cancer, etc., and methods of preparing such compounds.

38 Claims, No Drawings

OTHER PUBLICATIONS

Clark et al. (1995) "Antitumor Imidazotetrazines. 32. Synthesis of Novel Imidazotetrazinones and Related Bicyclic Heterocycles to Probe the Mode of Action of the Antitumor Drug Temozolomide", J. Med. Chem., 38(9):1493-1504.

Diana et al. (2009) "Pyrido[2',3':4,5]pyrrolo[2,1-d][1,2,3,5]tetrazine-4(3H)-ones, a new class of temozolomide heteroanalogues", ARKIVOC, (viii):177-186.

Diana et al. (2009) "Pyrido[4',3':4,5]pyrrolo[2,1-d][1,2,3,5]tetrazine a new class of Temozolomide heteroanalogues", ARKIVOC, (x):1-11.

Fisher et al. (1961) "Nitro- and amino-imidazolesulphonamides", Can. J. Chem., 39:501-504.

Gao et al. (2010) "Synthesis of Pyrazolo[5,1-d][1,2,3,5]tetrazine-4(3H)-ones", J. Comb. Chem., 12:69-74.

Hartley et al. (1988) "DNA sequence specificity of guanine N7-alkylations for a series of structurally related triazenes", Carcinogenesis, 9:669-674.

Hegi et al. (2004) "Clinical trial substantiates the predictive value of O-6-Methylguanin-DNA-Methyltransferase promoter methylation in glioblastmoa patients treated with temozolomide", Clin. Cancer Res., 10:1871-1874.

Hegi et al. (2005) "MGMT Gene Silencing and Benefit from Temozolomide in Glioblastoma", New England J. Med., 352:997-1003.

Horspool et al. (1990) "Antitumor Imidazotetrazines. 20. Preparation of the 8-Acid Derivatives of Mitozolomide and Its Utility in the Preparation of Active Antitumor Agents", J. Med. Chem. 33(5):1393-1399.

Jones et al. (1924) "A study of some new hydroxamic acids of hydroxyl and alkoxy fatty acids", J. Am. Chem. Soc., 46:2518.

Langnel et al. (2000) "Anti-tumor imidazotetrazines. 38. New 8-substituted derivatives of the imidazo[5,1-d]-1,2,3,5-tetrazines temozolomide and mitozolomide", ARKIVOC, (iii):421-437.

Lee et al. (1994) "Inactivation of O6-alkylguanine-DNA alkyltransferase in human peripeheral blood mononuclear cells by temozolomide", Br. J. Cancer, 69:452-456.

Lowe et al. (1992) "Antitumor imidazotetrazines. 25. Crystal structure of 8-carbamoyl-3-methylimidazo[5,1-d]-1,2,3,5-tetrazin-4(3H)-one (temozolomide) and structural comparisons with the related drugs mitozolomide and DTIC", J. Med. Chem., 35(18):3377-3382.

Lowe et al. (1994) "DCMCIT, an Analogue of the Antitumour Drugs Mitozolomide and Temozolomide", Acta Crystallographica Sect. C, 50:1629-1631.

Lunt et al. (1987) "Antitumor Imidazotetrazines. 14. Synthesis and Antitumor Activity of 6- and 8-Substituted Imidazo Not 5,1-D 3/4 -1,2,3,5-Tetrazinones and 8-Substituted Pyrazolo Not 5,1-D 3/4 -1,2,3,5-Tetrazinones", J. Med. Chem., 30(2):357-366.

Mosmann (1983) "Rapid colorimetric assay for cellular growth and survival: Application to proliferation and cytotoxicity assays", Journal of Immunological Methods, 65(1-2):55-63.

Newlands et al. (1997) "Temozolomide: a review of its discovery, chemical properties, pre-clinical development and clinical trials", Cancer Treat. Rev., 23:35-61.

Ozaki (1972) "Recent Advances in isocyanate chemistry", Chem. Rev., 72:457-496.

Saunders et al. (1948) "The chemistry of organic isocyanates", Chem. Rev., 43:203-218.

Shioiri et al. (1972) "Diphenylphosphoryl Azide. A New Convenient Reagent for a Modified Curtius Reaction and for the Peptide Synthesis", J. Am. Chem. Soc., 94:6203-6205.

Stevens and Newlands (1993) "From Triazines and Triazenes to Temozolomide", Eur. J. Cancer, 29A:1045-1047.

Stevens et al. (1984) "Antitumour imidazotetrazines. Part 1. Synthesis and chemistry of 8-carbamoyl-3-(2-chloroethyl)imidazo[1,5-d]-1,2,3,5-tetrazin-4(3H)-one, a novel broad spectrum antitumour agent", J. Med. Chem., 27:196-201.

Suresh Babu et al. (2000) "(Fluoren-9-ylmethoxy)carbonyl (Fmoc) amino acid azides: Synthesis, isolation, characterisation, stability and application to synthesis of peptides", J. Chem. Soc. Perkin Trans. 1, 4328-4331.

Tisdale et al. (1985) "Induction of Haemoglobin Synthesis in the Human leukaemia Cell line K562 by Monomethyltriazenes and Imidazotetrazinones", Biochem. Pharmacol., 34(12):2077-2082.

Viola et al. (2009) "Pyrrolotetrazinones deazaanalogues of temozolomide induce apoptosis in Jurkat cell line: involvement of tubulin polymerization inhibition", Cancer Chemother. Pharmacol., 64:1235-1251.

Walsh et al. (1996) "Solid phase synthesis of a mitozolomide-oligonucleotide conjugate using a novel silyl-linked solid support", Pharmaceutical Sciences, 2(1):33-38.

Wang et al. (1996) "Synthetic studies of 8-carbamoylimidazo-[5,1-D]-1,2,3,5-tetrazin-4(3H)-one: a key derivative of antitumour drug temozolomide", Bioorg. Med. Chem. Lett., 6(2):185-188.

Wang et al. (2002) "Synthesis and antibacterial activity of dual-action agents of a b-lactam antibiotic with cytotoxic agent mitozolomide or temozolomide", Eur. J. Med. Chem., 37:323-332.

Wang et al. (1998) "Antitumour imidazotetrazines. Part 36. Conversion of 5-amino-imidazole-4-carboxamide to imidazo[5,1-d][1,2,3,5]tetrazin-4(3H)-ones and imidazo[1,5-a][1,3,5]triazin-4(3H)-ones related in structure to the antitumour agents temozolomide and mitozolomide", J. Chem. Soc. Perkin Trans. 1, 10:1669-1675.

Wang et al. (1995) "Antitumour imidazotetrazines. Part 33. New syntheses of the antitumour drug temozolomide using 'masked' methyl isocyanates", J. Chem. Soc. Perkin Trans. 1, 21:2783-2787.

Wanner et al. (2002) "A new synthesis of temozolomide", J. Chem. Soc. Perkin Trans. 1, 1877-1880.

Wedge et al. (1996) "3-Aminobenzamide and/or 06-benzylguanine evaluated as an adjuvant to temozolomide or BCNU treatment in cell lines of variable mismatch repair status and 06-alkylguanine-DNA alkyltransferase activity", Br. J. Cancer, 74:1030-1036.

Wermuth (1996) "Molecular Variations Based on Isosteric Replacements", Practice of Medicinal Chemistry, 203-327.

Yalpn et al. (1992) "The synthesis and the structure-activity relationships of some substituted benzoxazoles, oxazolo(4,5=b)pyridines, benzothiazoles and benzimidazoles as antimicrobial agents", Eur. J. Med. Chem., 27:401-406.

Zhao et al. (2001) "Synthesis and Antitumour Activities of 3-Substituted 4-Oxo-3H-imidazo(5,1-d)(1,2,3,5)tetrazine- 8-carboxylic Acids and Their Derivatives", Chinese J. Med. Chem., 11(5):263-269.

Zhu et al. (2007) "Design, Synthesis, and Quantitative Structure-Activity Relationship Study of Herbicidal Analogues of Pyrazolo[5,1-d][1,2,3,5]tetrazin-4(3H)ones", J. Agric. Food Chem., 55:1364-1369.

International Preliminary Report on Patentability dated Jan. 12, 2012 from PCT/GB2010/001233.

International Search Report and the Written Opinion dated Oct. 6, 2010 from PCT/GB2010/001233.

* cited by examiner

3-SUBSTITUTED-4-OXO-3,4-DIHYDRO-IMIDAZO[5,1-D][1,2,3,5-TETRAZINE-8-CARBOXYLIC ACID AMIDES AND THEIR USE

RELATED APPLICATION

This application is a 35 U.S.C. §371 national phase application of PCT/GB2008/004140 (WO 2009/077741) filed 16 Dec. 2008, entitled "3-Substituted-4-oxo-3,4-Dihydro-Imidazo[5,1-d][1,2,3,5-Tetrazine-8-Carboxylic Acid Amides and Their Use." PCT/GB2008/004140 is a non-provisional application of U.S. provisional patent application No. 61/014,520 filed 18 Dec. 2007, the contents of which are incorporated herein by reference in their entirety.

TECHNICAL FIELD

The present invention pertains generally to the field of therapeutic compounds, and more specifically to certain 3-substituted-4-oxo-3,4-dihydro-imidazo[5,1-d][1,2,3,5]tetrazine-8-carboxylic acid amide (collectively referred to herein as 3TM compounds). The present invention also pertains to pharmaceutical compositions comprising such compounds, and the use of such compounds and compositions, both in vitro and in vivo, to inhibit cell proliferation, and in the treatment of proliferative disorders such as cancer, etc., and methods of preparing such compounds.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.
Temozolomide Temozolomide (also known as 3,4-dihydro-3-methyl-4-oxoimidazo[5,1-d]-1,2,3,5-tetrazine-8-carboxamide; 8-carbamoyl-3-methylimidazo[5,1-d]-1,2,3,5-tetrazin-4(3H)-one; methazolastone; M & B 39831; CCRG-81045; NSC-362856; Temodal; Temodar) is a well known anti-neoplastic agent that acts as an alkylating agent. Its primary application is in the treatment of brain cancer (e.g., glioma).

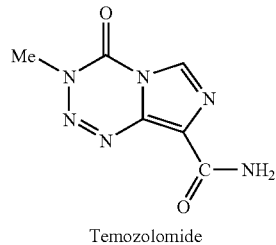 [SMILES: Cn1nnc2c(C(N)=O)ncn2c1=O]

Temozolomide

Temozolomide is a prodrug, being cleaved in a multi-step pathway firstly to liberate an unstable monomethyltriazene (MTIC), which then suffers proteolytic fragmentation to generate a highly-reactive methylating agent (methanediazonium ion) and 5-aminoimidazole-4-carboxamide (see, e.g., Arrowsmith et al., 2002, J. Med. Chem., Vol. 45, pp. 5458-5470). Support for this process comes from the isolation of MTIC from the degradation of temozolomide in aqueous sodium carbonate solution (see, e.g., Stevens et al., 1984, J. Med. Chem., Vol. 27, pp. 196-201). There is only a small pH window around physiological pH where ring-opening of temozolomide is accompanied by fragmentation of MTIC in a methylating mode.

The methanediazonium active species derived from MTIC (or temozolomide) is believed to covalently methylate guanine residues of DNA in tracts of three or more guanines (see, e.g., Hartley et al., 1988, Carcinogenesis, Vol. 9, pp. 669-674; Clark et al., 1995, J. Med. Chem., Vol. 38, pp. 1493-1504). The significant site of DNA methylation is the O-6 position of guanine residues and tumours which express high levels of the DNA repair protein O(6)-methylguanine methyltransferase (MGMT; also known as ATase) are inherently resistant to the drug (see, e.g., Wedge et al., 1996, Br. J. Cancer, Vol. 74, pp. 1030-1036; Lee et al., 1994, Br. J. Cancer, Vol. 69, pp. 452-456.) These studies have been reviewed (see, e.g., Stevens and Newlands, 1993, Eur. J. Cancer, Vol. 29A, pp. 1045-1047; Newlands et al., 1997, Cancer Treat. Rev., Vol. 23, pp. 35-61). O-6 guanine methylation is a cytotoxic (anti-tumor) lesion since it provokes base mis-pairing with thymine during DNA replication. Unless repaired by MGMT, mis-pairing on the daughter strand is recognised by mismatch repair proteins which trigger futile cycles of thymine excision and re-insertion leading to persistent DNA strand breaks.

In a significant development in our understanding of the molecular determinants influencing tumor responses to temozolomide, it is now clear that the promoter methylation status (at cytosine C-5 in CpG sequences of the MGMT gene) is a powerful predictor of clinical outcome in glioblastoma patients (see, e.g., Hegi et al., 2004, Clin. Cancer Res. Vol. 10, pp. 1871-1874; Hegi et al., 2005, New England J. Med., Vol. 352, pp. 997-1003). Tumors with the MGMT gene switched off, as in some brain tumors, are unable to repair the O-6 guanine lesions and are particularly sensitive to temozolomide. Conversely, most common tumors with the MGMT repair gene switched on, leading to high cellular levels of MGMT, can repair the O-6 guanine lesions and are resistant to the drug. This epigenetic feature considerably restricts the spectrum of action of temozolomide and its penetration of the cancer market.

A new strategy to overcome these deficiencies proposes that compounds structurally related in structure to temozolomide and retaining the drug's favourable pharmaceutical profile—such as ease of synthesis, acid stability, oral bioavailability, freedom from metabolic complications, transmission across the blood-brain barrier, and an acceptable toxicological profile—could be developed which create an alternative anti-tumor lesion at O-6 residues of guanines in DNA (i.e., not methylation) which cannot be repaired by MGMT. Such compounds would be likely to retain useful therapeutic activity against all brain tumors, but also those major killer tumor types (e.g., lung, breast, ovarian, colorectal, renal, pancreatic, melanoma) which are currently inherently resistant to temozolomide.

Temozolomide is the subject of granted claim 13 of U.S. Pat. No. 5,260,291 to Lunt et al. granted 9 Nov. 1993.

SUMMARY OF THE INVENTION

One aspect of the invention pertains to certain 3-substituted-4-oxo-3,4-dihydro-imidazo[5,1-d][1,2,3,5]tetrazine-8-carboxylic acid amide (collectively referred to herein as 3TM compounds), as described herein.

Another aspect of the invention pertains to compositions (e.g., a pharmaceutical compositions) comprising a 3TM compound, as described herein, and a pharmaceutically acceptable carrier or diluent.

Another aspect of the invention pertains to methods of preparing a composition (e.g., a pharmaceutical composition) comprising the step of admixing a 3TM compound, as described herein, and a pharmaceutically acceptable carrier or diluent.

Another aspect of the present invention pertains to methods of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of a 3TM compound, as described herein.

Another aspect of the present invention pertains to corresponding methods (e.g., methods of regulating, etc.), employing a PX compound or a salt, hydrate, and solvate thereof, as described herein.

Another aspect of the present invention pertains to methods of treatment comprising administering to a subject in need of treatment a therapeutically-effective amount of a 3TM compound, as described herein, preferably in the form of a pharmaceutical composition.

Another aspect of the present invention pertains to corresponding methods of treatment employing a PX compound or a salt, hydrate, and solvate thereof, as described herein.

Another aspect of the present invention pertains to a 3TM compound as described herein for use in a method of treatment of the human or animal body by therapy.

Another aspect of the present invention pertains to a PX compound or a salt, hydrate, and solvate thereof, as described herein, for use in a method of treatment of the human or animal body by therapy.

Another aspect of the present invention pertains to use of a 3TM compound, as described herein, in the manufacture of a medicament for use in treatment.

Another aspect of the present invention pertains to use of a PX compound or a salt, hydrate, and solvate thereof, as described herein, in the manufacture of a medicament for use in treatment.

In one embodiment, the treatment is treatment of a proliferative disorder.

In one embodiment, the treatment is treatment of cancer.

In one embodiment, the treatment is treatment of: lung cancer, breast cancer, ovarian cancer, colorectal cancer, melanoma, renal cancer, prostate cancer, esophageal cancer, squamous carcinoma of the head or neck, or glioma.

Another aspect of the present invention pertains to a kit comprising (a) a 3TM compound, as described herein, preferably provided as a pharmaceutical composition and in a suitable container and/or with suitable packaging; and (b) instructions for use, for example, written instructions on how to administer the compound.

Another aspect of the present invention pertains to certain methods of synthesis, as described herein.

Another aspect of the present invention pertains to a compound (e.g., a 3TM compound) obtainable by a method of synthesis as described herein, or a method comprising a method of synthesis as described herein.

Another aspect of the present invention pertains to a compound (e.g., a 3TM compound) obtained by a method of synthesis as described herein, or a method comprising a method of synthesis as described herein.

Another aspect of the present invention pertains to certain novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Compounds

One aspect of the present invention pertains to certain compounds that may be considered to be 3-derivatives of Temozolomide (also known as 3-methyl-4-oxo-3,4-dihydro-imidazo[5,1-d][1,2,3,5]tetrazine-8-carboxylic acid amide):

Temozolomide

Thus, one aspect of the present invention pertains to compounds selected from compounds of the following formula and salts, hydrates, and solvates thereof (e.g., pharmaceutically acceptable salts, hydrates, and solvates thereof), wherein Q is as defined herein (collectively denoted herein as "3TM compounds"):

Certain aspects of the present invention (e.g., methods of treatment, compounds for use in a method of treatment, etc.) relate to compounds selected from those compounds identified herein with PX code numbers (which may already be known compounds) and collectively referred to herein as "PX Compounds".

Aryl-Alkyl Compounds

It appears that the following compounds may be known:

| Code No. | Structure | Registry No. |
|---|---|---|
| PX-001 | 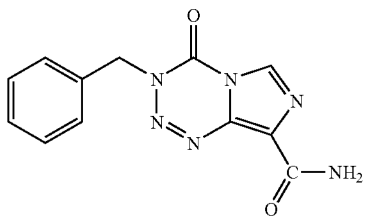 [SMILES: NC(=O)c1ncn2c(=O)n(Cc3ccccc3)nnc12] | 85623-02-5 |
| PX-002 | 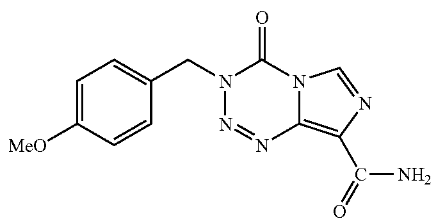 [SMILES: COc1ccc(Cn2nnc3c(C(N)=O)ncn3c2=O)cc1] | 85623-05-8 |
| PX-003 | 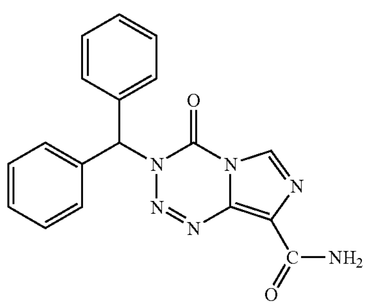 [SMILES: NC(=O)c1ncn2c(=O)n(C(c3ccccc3)c3ccccc3)nnc12] | 172988-52-2 |
| PX-004 | 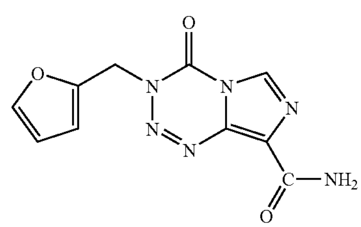 [SMILES: NC(=O)c1ncn2c(=O)n(Cc3ccco3)nnc12] | 208107-16-8 |
| PX-005 | 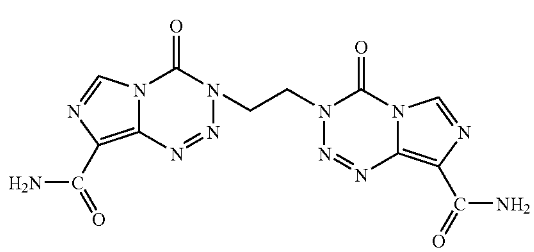 [SMILES: NC(=O)c1ncn2c(=O)n(CCn3nnc4c(C(N)=O)ncn4c3=O)nnc12] | 331456-41-8 |

(For aspects of the invention relating to new uses of these compounds, see the section below entitled "Uses of Certain Known Compounds".)

In one embodiment, -Q is independently a group of the following formula:

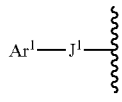

wherein:

—Ar$^1$ is independently phenyl or C$_{5-6}$heteroaryl, and is optionally substituted;

-J$^1$- is independently saturated aliphatic C$_{1-4}$alkylene;

with the proviso that -Q is not benzyl, para-methoxy-benzyl, or furan-2-yl-methyl.

In one embodiment, —Ar$^1$ is independently phenyl and is optionally substituted.

In one embodiment, —Ar$^1$ is independently $C_{5-6}$heteroaryl and is optionally substituted.

In one embodiment, —Ar$^1$ is independently $C_5$heteroaryl and is optionally substituted.

In one embodiment, —Ar$^1$ is independently thienyl and is optionally substituted.

In one embodiment, —Ar$^1$ is independently thien-2-yl and is optionally substituted.

In one embodiment, —Ar$^1$ is independently thien-3-yl and is optionally substituted.

In one embodiment, —Ar$^1$ is independently pyrazolyl and is optionally substituted.

In one embodiment, —Ar$^1$ is independently pyrazol-1-yl and is optionally substituted.

In one embodiment, —Ar$^1$ is independently oxadiazolyl and is optionally substituted.

In one embodiment, —Ar$^1$ is independently [1,2,4]oxadiazolyl and is optionally substituted.

In one embodiment, —Ar$^1$ is independently [1,2,4]oxadiazol-5-yl and is optionally substituted.

In one embodiment, —Ar$^1$ is independently triazolyl and is optionally substituted.

In one embodiment, —Ar$^1$ is independently [1,2,3]triazolyl and is optionally substituted.

In one embodiment, —Ar$^1$ is independently [1,2,3]triazol-5-yl and is optionally substituted.

In one embodiment, —Ar$^1$ is independently isoxazolyl and is optionally substituted.

In one embodiment, —Ar$^1$ is independently isoxazol-5-yl and is optionally substituted.

In one embodiment, -J$^1$- is independently saturated aliphatic $C_{1-3}$alkylene.

In one embodiment, -J$^1$- is independently saturated aliphatic $C_{1-2}$alkylene.

In one embodiment, -J$^1$- is independently saturated aliphatic $C_{2-4}$alkylene.

In one embodiment, -J$^1$- is independently saturated aliphatic $C_{2-3}$alkylene.

In one embodiment, -J$^1$- is independently —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, or —CH(CH$_2$CH$_3$)—.

In one embodiment, -J$^1$- is independently —CH$_2$CH$_2$—, —CH$_2$CH$_2$CH$_2$—, —CH(CH$_3$)—, —CH(CH$_3$)CH$_2$—, —CH$_2$CH(CH$_3$)—, or —CH(CH$_2$CH$_3$)—.

In one embodiment, -J$^1$- is independently —CH$_2$—, —CH(CH$_3$)—, or —CH(CH$_2$CH$_3$)—.

In one embodiment, -J$^1$- is independently —CH(CH$_3$)— or —CH(CH$_2$CH$_3$)—.

In one embodiment, -J$^1$- is independently —CH(CH$_3$)—.

In one embodiment, -J$^1$- is independently —CH(CH$_2$CH$_3$)—.

In one embodiment, -J$^1$- is independently —CH$_2$CH$_2$—, —CH(CH$_3$)CH$_2$—, or —CH$_2$CH(CH$_3$)—.

In one embodiment, -J$^1$- is independently —CH$_2$CH$_2$—.

In one embodiment, —Ar$^1$ is independently unsubstituted or substituted with one or more substituents independently selected from: —F, —Cl, —Br, —I, —OH, —OR$^{Z1}$, —SH, —SR$^{Z1}$, —NO$_2$, —CN, —NH$_2$, —NHR$^{Z1}$, —NR$^{Z1}_2$, —COOH, —COOR$^{Z1}$, —CONH$_2$, —CONHR$^{Z1}$, —CONR$^{Z1}_2$, —NHCOOH, —NR$^{11}$COOH, —NHCOOR$^{Z1}$, and —NR$^{Z1}$COOR$^{Z1}$, wherein each —R$^{Z1}$ is independently saturated aliphatic $C_{1-4}$alkyl, phenyl, or benzyl, wherein said phenyl and benzyl are independently optionally substituted with one or more substituents selected from —F, —Cl, —Br, —I, —R$^{Z1R}$, —CF$_3$, —OH, and —OR$^{Z1R}$, wherein each —R$^{Z1R}$ is independently saturated aliphatic $C_{1-4}$alkyl.

In one embodiment, —Ar$^1$ is independently unsubstituted or substituted with one or more substituents independently selected from: —F, —Cl, —Br, —I, —OH, —OR$^{Z1}$, —SH, —SR$^{Z1}$, —NO$_2$, —CN, —NH$_2$, —NHR$^{Z1}$, —NR$^{Z1}_2$, —COOH, —COOR$^{Z1}$, —CONH$_2$, —CONHR$^{Z1}$, —CONR$^{Z1}_2$, —NHCOOH, —NR$^{Z1}$COOH, —NHCOOR$^{Z1}$, and —NR$^{Z1}$COOR$^{Z1}$, wherein each R$^{Z1}$ is independently saturated aliphatic $C_{1-4}$alkyl, phenyl, or benzyl.

In one embodiment, —Ar$^1$ is independently unsubstituted or substituted with one or more substituents independently selected from: —F, —Cl, —Br, —I, —OH, and —OR$^{Z1}$, wherein R$^{Z1}$ is independently saturated aliphatic $C_{1-4}$alkyl.

In one embodiment, —Ar$^1$ is independently unsubstituted or substituted with one or more substituents independently selected from: —OR$^{Z1}$, wherein R$^{Z1}$ is independently saturated aliphatic $C_{1-4}$alkyl.

In one embodiment, —Ar$^1$ is independently unsubstituted or substituted with one or more substituents independently selected from: —F, —Cl, —Br, and —I.

In one embodiment, —Ar$^1$ is independently unsubstituted or substituted with one or more substituents independently selected from: —OMe or —Br.

In one embodiment, —Ar$^1$ is independently unsubstituted or substituted with one or more —OMe substituents.

In one embodiment, —Ar$^1$ is independently unsubstituted or substituted with one or more —Br substituents.

In one embodiment, —Ar$^1$ is independently unsubstituted.

In one embodiment, the compound is selected from compounds of the following formulae and salts, hydrates, and solvates thereof (e.g., pharmaceutically acceptable salts, hydrates, and solvates thereof):

| Code No. | Synthesis No. | Structure |
| --- | --- | --- |
| AA-001 | Synthesis 25 | 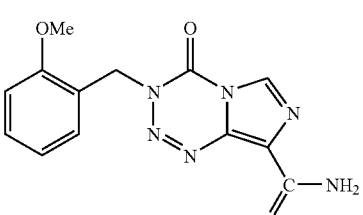 |

-continued
| Code No. | Synthesis No. | Structure |
|---|---|---|
| AA-002 | Synthesis 26 | 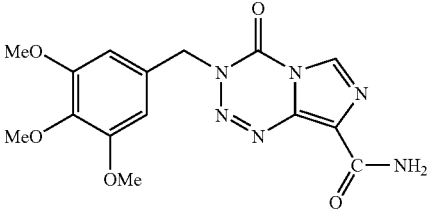 [SMILES: COc1cc(Cn2nnc3c(C(N)=O)ncn3c2=O)cc(OC)c1OC] |
| AA-003 | Synthesis 27 | 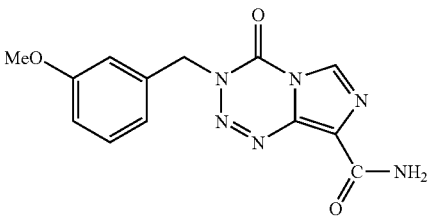 [SMILES: COc1cccc(Cn2nnc3c(C(N)=O)ncn3c2=O)c1] |
| AA-004 | Synthesis 29 | 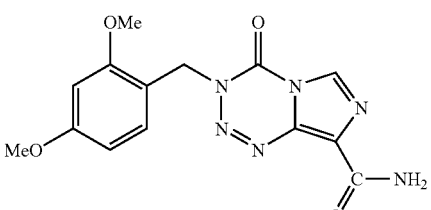 |
| AA-005 | Synthesis 30 | 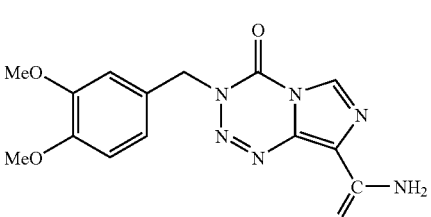 |
In one embodiment, the compound is selected from compounds of the following formulae and salts, hydrates, and solvates thereof (e.g., pharmaceutically acceptable salts, hydrates, and solvates thereof):
| Code No. | Synthesis No. | Structure |
|---|---|---|
| BB-001 | Synthesis 13 | 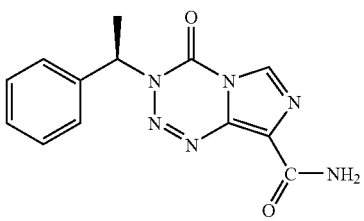 [SMILES: C[C@H](c1ccccc1)n1nnc2c(C(N)=O)ncn2c1=O] |

-continued

| Code No. | Synthesis No. | Structure |
|---|---|---|
| BB-002 | Synthesis 14 | 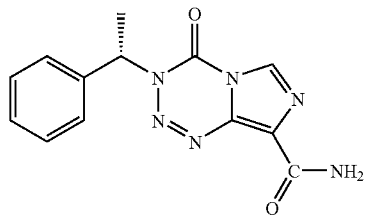 [SMILES: C[C@@H](c1ccccc1)n1nnc2c(C(N)=O)ncn2c1=O] |
| BB-003 | Synthesis 18 | 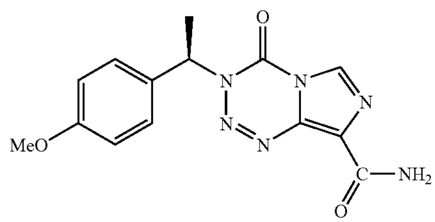 [SMILES: COc1ccc([C@@H](C)n2nnc3c(C(N)=O)ncn3c2=O)cc1] |
| BB-004 | Synthesis 20 | 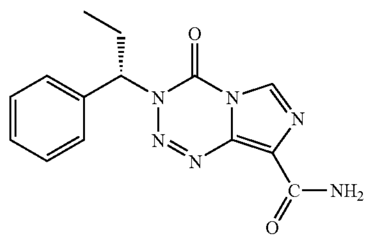 [SMILES: CC[C@@H](c1ccccc1)n1nnc2c(C(N)=O)ncn2c1=O] |
| BB-005 | Synthesis 21 | 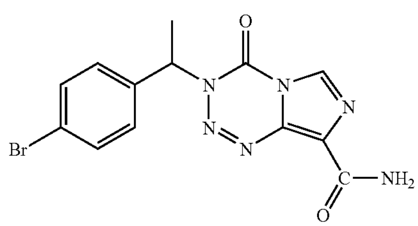 [SMILES: CC(c1ccc(Br)cc1)n1nnc2c(C(N)=O)ncn2c1=O] |
| BB-006 | Synthesis 24 | 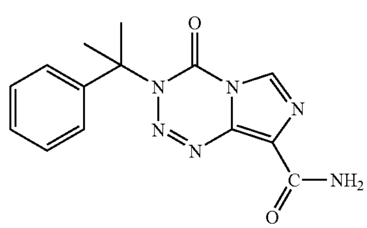 [SMILES: CC(C)(c1ccccc1)n1nnc2c(C(N)=O)ncn2c1=O] |
| BB-007 | Synthesis 42 | 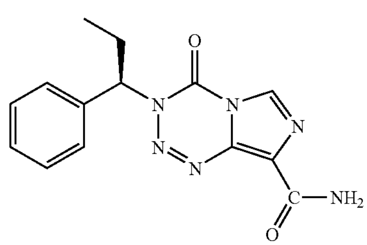 [SMILES: CC[C@H](c1ccccc1)n1nnc2c(C(N)=O)ncn2c1=O] |

In one embodiment, the compound is selected from compounds of the following formulae and salts, hydrates, and solvates thereof (e.g., pharmaceutically acceptable salts, hydrates, and solvates thereof):

| Code No. | Synthesis No. | Structure |
|---|---|---|
| CC-001 | Synthesis 31 | 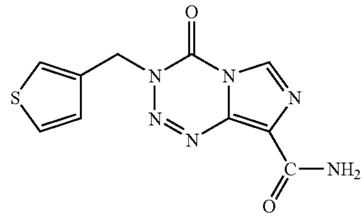 [SMILES: NC(=O)c1ncn2c(=O)n(Cc3ccsc3)nnc12] |
| CC-002 | Synthesis 32 | 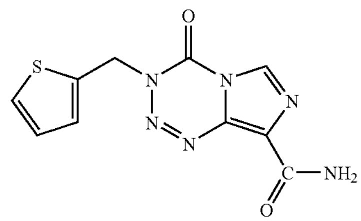 |
| CC-003 | Synthesis 42 | 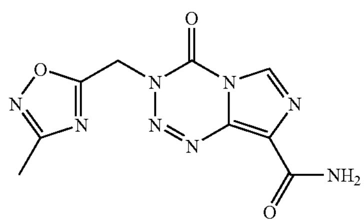 [SMILES: Cc1noc(Cn2nnc3c(C(N)=O)ncn3c2=O)n1] |
| CC-004 | Synthesis 43 | 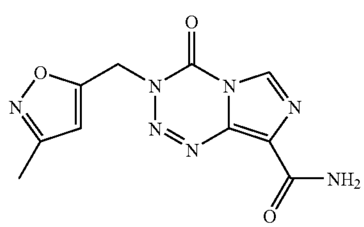 [SMILES: Cc1cc(Cn2nnc3c(C(N)=O)ncn3c2=O)on1] |
| CC-005 | Synthesis 44 | 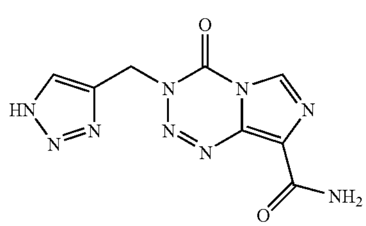 [SMILES: NC(=O)c1ncn2c(=O)n(Cc3c[nH]nn3)nnc12] |

In one embodiment, the compound is selected from compounds of the following formulae and salts, hydrates, and solvates thereof (e.g., pharmaceutically acceptable salts, hydrates, and solvates thereof):

| Code No. | Synthesis No. | Structure |
|---|---|---|
| DD-001 | Synthesis 28 | 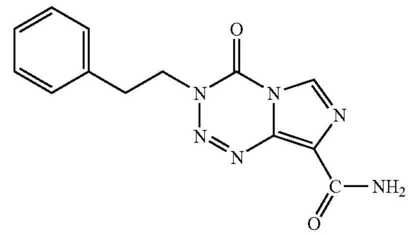 [SMILES: NC(=O)c1ncn2c(=O)n(CCc3ccccc3)nnc12] |

Alkynyl Compounds

In one embodiment, -Q is independently a group of the following formula:

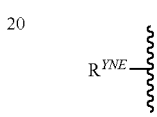

wherein —$R^{YNE}$ is independently aliphatic $C_{2-6}$alkynyl, and is optionally substituted.

As used herein, the term "alkynyl" relates to an aliphatic hydrocarbyl group (i.e., a group having only carbon atoms and hydrogen atoms) having at least one carbon-carbon triple bond.

In one embodiment, —$R^{YNE}$ is independently aliphatic $C_{3-5}$alkynyl, and is optionally substituted.

In one embodiment, —$R^{YNE}$ is independently unsubstituted or substituted with one or more substituents independently selected from: —F, —Cl, —Br, —I, —OH, —$OR^{Z3}$, —SH, —$SR^{Z3}$, —$SiR^{Z3}{}_3$, —$NO_2$, —CN, —$NH_2$, —$NHR^{Z3}$, —$NR^{Z3}{}_2$, —COOH, —$COOR^{Z3}$, —$CONH_2$, —$CONHR^{Z3}$, —$CONR^{Z3}{}_2$, —NHCOOH, —$NR^{Z3}COOH$, —$NHCOOR^{Z3}$, and —$NR^{Z3}COOR^{Z3}$, wherein each $R^{Z3}$ is independently saturated aliphatic $C_{1-4}$alkyl, phenyl, or benzyl, wherein said phenyl and benzyl are independently optionally substituted with one or more substituents selected from —F, —Cl, —Br, —I, —$R^{Z3R}$, —$CF_3$, —OH, and —$OR^{Z3R}$, wherein each —$R^{Z3R}$ is independently saturated aliphatic $C_{1-4}$alkyl.

In one embodiment, —$R^{YNE}$ is independently unsubstituted or substituted with one or more substituents independently selected from: —F, —Cl, —Br, —I, —OH, —$OR^{Z3}$, —SH, —$SR^{Z3}$, —$NO_2$, —CN, —$NH_2$, —$NHR^{Z3}$, —$NR^{Z3}{}_2$, —COOH, —$COOR^{Z3}$, —$CONH_2$, —$CONHR^{Z3}$, —$CONR^{Z3}{}_2$, —NHCOOH, —$NR^{Z3}COOH$, —$NHCOOR^{Z3}$, and —$NR^{Z3}COOR^{Z3}$, wherein each $R^{Z3}$ is independently saturated aliphatic $C_{1-4}$alkyl, phenyl, or benzyl.

In one embodiment, —$R^{YNE}$ is independently unsubstituted.

In one embodiment, —$R^{YNE}$ is independently:
—C≡CH,
—C≡C—$CH_3$, —$CH_2$—C≡CH,
—C≡C—$CH_2$—$CH_3$, —C≡C—CH=$CH_2$, —C≡C—C≡CH,
—$CH_2$—$CH_2$—C≡CH, —CH=CH—C≡CH, —C≡C—C≡CH,
—$CH_2$—C≡C—$CH_3$, or
—CH($CH_3$)—C≡CH.

In one embodiment, —$R^{YNE}$ is independently —$CH_2$—C≡CH.

In one embodiment, the compound is selected from compounds of the following formula and salts, hydrates, and solvates thereof (e.g., pharmaceutically acceptable salts, hydrates, and solvates thereof):

| Code No. | Synthesis No. | Structure |
|---|---|---|
| EE-001 | Synthesis 19 | *(structure shown)* |
| EE-002 | Synthesis 45 | *(structure shown)* |
| EE-003 | Synthesis 46 | *(structure shown)* |

Cyclic-Alkyl Compounds

It appears that the following compound may be known:

| Code No. | Structure | Registry No. |
|---|---|---|
| PX-006 | *(structure shown)* | 85623-04-7 |

(For aspects of the invention relating to new uses of these compounds, see the section below entitled "Uses of Certain Known Compounds".)

In one embodiment, -Q is independently a group of the following formula:

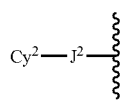

wherein:
-$Cy^2$ is independently:
saturated $C_{3-7}$cycloalkyl and is optionally substituted, or non-aromatic $C_{3-7}$heterocyclyl and is optionally substituted;

-$J^2$- is independently a covalent bond or saturated aliphatic $C_{1-4}$alkylene; with proviso that if -Q is not cyclohexyl.

In one embodiment, -$Cy^2$ is independently saturated $C_{3-7}$cycloalkyl and is optionally substituted.

In one embodiment, -$Cy^2$ is independently saturated $C_{3-6}$cycloalkyl and is optionally substituted.

In one embodiment, -$Cy^2$ is independently cyclopropyl, cyclopentyl, or cyclohexyl, and is optionally substituted.

In one embodiment, -$Cy^2$ is independently non-aromatic $C_{3-7}$heterocyclyl and is optionally substituted.

In one embodiment, -$Cy^2$ is independently non-aromatic $C_{6-6}$heterocyclyl and is optionally substituted.

In one embodiment, -$Cy^2$ is independently piperidinyl and is optionally substituted.

In one embodiment, -$Cy^2$ is independently piperidin-4-yl and is optionally substituted.

In one embodiment, -$J^2$- is independently a covalent bond.

In one embodiment, -$J^2$- is independently saturated aliphatic $C_{1-3}$alkylene.

In one embodiment, -$J^2$- is independently saturated aliphatic $C_{7-2}$alkylene.

In one embodiment, -$J^2$- is independently —$CH_2$—, —$CH_2CH_2$—, —$CH_2CH_2CH_2$—, —$CH(CH_3)$—, —$CH(CH_3)CH_2$—, —$CH_2CH(CH_3)$—, or —$CH(CH_2CH_3)$—.

In one embodiment, -$J^2$- is independently —$CH_2$—, —$CH(CH_3)$—, or —$CH(CH_2CH_3)$—.

In one embodiment, -$J^2$- is independently —$CH(CH_3)$— or —$CH(CH_2CH_3)$—.

In one embodiment, -$J^2$- is independently —$CH(CH_3)$—.

In one embodiment, -$J^2$- is independently —$CH(CH_2CH_3)$—.

In one embodiment, -$J^2$- is independently —$CH_2CH_2$—, —$CH(CH_3)CH_2$—, or —$CH_2CH(CH_3)$—.

In one embodiment, -$J^2$- is independently —$CH_2CH_2$—.

In one embodiment, -$Cy^2$ is independently unsubstituted or substituted with one or more substituents independently selected from: —F, —Cl, —Br, —I, —OH, —$OR^{Z2}$, —SH, —$SR^{Z2}$, —$NO_2$, —CN, —$NH_2$, —$NHR^{Z2}$, —$NR^{Z2}_2$, —COOH, —$COOR^{Z2}$, —$CONH_2$, —$CONHR^{Z2}$, —$CONR^{Z2}_2$, —NHCOOH, —$NR^{Z2}COOH$, —$NHCOOR^{Z2}$, and —$NR^{Z2}COOR^{Z2}$, wherein each $R^{Z2}$ is independently saturated aliphatic $C_{1-4}$alkyl, phenyl, or benzyl, wherein said phenyl and benzyl are independently optionally substituted with one or more substituents selected from —F, —Cl, —Br, —I, —$R^{Z1R}$, —$CF_3$, —OH, and —$OR^{Z1R}$, wherein each —$R^{Z1R}$ is independently saturated aliphatic $C_{1-4}$alkyl.

In one embodiment, -$Cy^2$ is independently unsubstituted or substituted with one or more substituents independently selected from: —F, —Cl, —Br, —I, —OH, —$OR^{Z2}$, —SH, —$NO_2$, —CN, —$NH_2$, —$NHR^{Z2}$, —$NR^{Z2}_2$, —COOH, —$COOR^{Z2}$, —$CONH_2$, —$CONHR^{Z2}$, —$CONR^{Z2}_2$, —NHCOOH, —$NR^{Z2}COOH$, —$NHCOOR^{Z2}$, and —$NR^{Z2}COOR^{Z2}$, wherein each $R^{Z2}$ is independently saturated aliphatic $C_{1-4}$alkyl, phenyl, or benzyl.

In one embodiment, -$Cy^2$ is independently unsubstituted or substituted with one or more substituents independently selected from: —F, —Cl, —Br, —I, —OH, and —$OR^{Z2}$, wherein —$R^{Z2}$ is independently saturated aliphatic $C_{1-4}$alkyl, phenyl, or benzyl.

In one embodiment, -$Cy^2$ is independently unsubstituted or substituted with one or more substituents independently selected from: —OMe or —Br.

In one embodiment, -$Cy^2$ is independently unsubstituted.

In one embodiment, the compound is selected from compounds of the following formulae and salts, hydrates, and solvates thereof (e.g., pharmaceutically acceptable salts, hydrates, and solvates thereof):

| Code No. | Synthesis No. | Structure |
|---|---|---|
| FF-001 | Synthesis 3 | 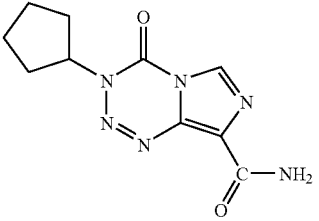 [SMILES: NC(=O)c1ncn2c(=O)n(C3CCCC3)nnc12] |
| FF-002 | Synthesis 5 | 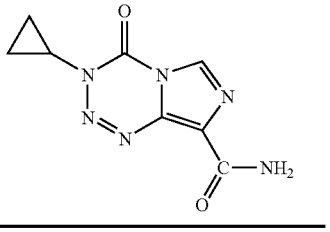 |

In one embodiment, the compound is selected from compounds of the following formulae and salts, hydrates, and solvates thereof (e.g., pharmaceutically acceptable salts, hydrates, and solvates thereof):

| Code No. | Synthesis No. | Structure |
|---|---|---|
| GG-001 | Synthesis 1 | 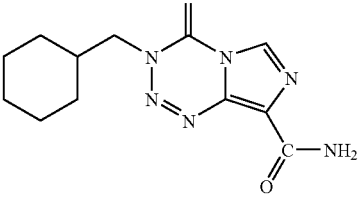 |
| GG-002 | Synthesis 12 | 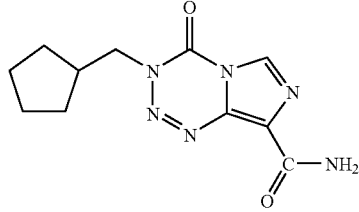 [SMILES: NC(=O)c1ncn2c(=O)n(CC3CCCC3)nnc12] |
| GG-003 | Synthesis 40 | 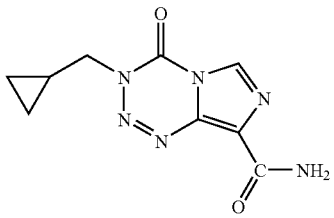 [SMILES: NC(=O)c1ncn2c(=O)n(CC3CC3)nnc12] |

In one embodiment, the compound is selected from compounds of the following formulae and salts, hydrates, and solvates thereof (e.g., pharmaceutically acceptable salts, hydrates, and solvates thereof):

| Code No. | Synthesis No. | Structure |
|---|---|---|
| HH-001 | Synthesis 4 | 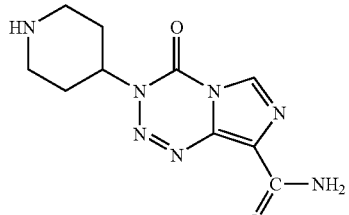 |

Amide-Substituted Alkyl Compounds

It appears that the following compounds may be known:

| Code No. | Structure | Registry No. |
|---|---|---|
| PX-007 | 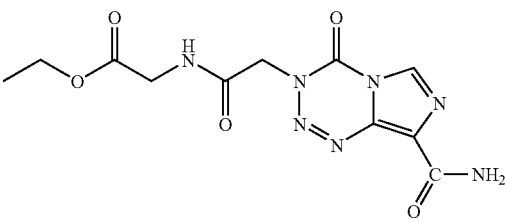 [SMILES: CCOC(=O)CNC(=O)Cn1nnc2c(C(N)=O)ncn2c1=O] | 172988-48-6 |
| PX-008 | 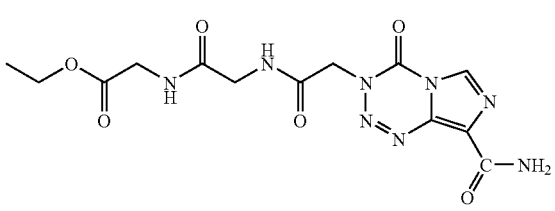 [SMILES: CCOC(=O)CNC(=O)CNC(=O)Cn1nnc2c(C(N)=O)ncn2c1=O] | 172988-49-7 |

(For aspects of the invention relating to new uses of these compounds, see the section below entitled "Uses of Certain Known Compounds".)

In one embodiment, -Q is independently a group of the following formula:

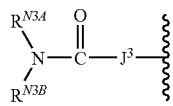

wherein:
- $-J^3-$ is independently saturated aliphatic $C_{1-4}$alkylene; and either:
  - $-R^{N3A}$ is independently —H or $-R^{N3C}$;
  - $-R^{N3B}$ is independently —H or $-R^{N3D}$;
  - $-R^{N3C}$ is independently saturated aliphatic $C_{1-4}$alkyl;
  - $-R^{N3D}$ is independently saturated aliphatic $C_{1-4}$alkyl;
  or:
  - $-R^{N3A}$ and $-R^{N3B}$, taken together with the nitrogen atom to which they are attached, form a 4-, 5-, 6-, or 7-membered non-aromatic ring having exactly one ring heteroatom which is nitrogen, or having exactly two ring heteroatoms, which are nitrogen and oxygen, or nitrogen and nitrogen.

In one embodiment, $-J^3-$ is independently saturated aliphatic $C_{1-3}$alkylene.

In one embodiment, $-J^3-$ is independently saturated aliphatic $C_{1-2}$alkylene.

In one embodiment, $-J^3-$ is independently —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, or —CH(CH$_2$CH$_3$)—.

In one embodiment, $-J^3-$ is independently —CH$_2$—, —CH$_2$CH$_2$—, or —CH$_2$CH$_2$CH$_2$—.

In one embodiment, $-J^3-$ is independently —CH$_2$— or —CH$_2$CF$_{12}$—

In one embodiment, $-J^3-$ is independently —CH$_2$CH$_2$—

In one embodiment, $-J^3-$ is independently —CH$_2$—.

In one embodiment:
- $-R^{N3A}$ is independently —H or $-R^{N3C}$;
- $-R^{N3B}$ is independently —H or $-R^{N3D}$.

In one embodiment:
- $-R^{N3A}$ is independently $-R^{N3C}$;
- $-R^{N3B}$ is independently —H or $-R^{N3D}$.

In one embodiment:
- $-R^{N3A}$ is independently —H;
- $-R^{N3B}$ is independently —H or $-R^{N3D}$.

In one embodiment:
- $-R^{N3A}$ is independently —H;
- $-R^{N3B}$ is independently —H.

In one embodiment:
- $-R^{N3A}$ is independently $-R^{N3C}$;
- $-R^{N3B}$ is independently $-R^{N3D}$.

In one embodiment, $-R^{N3C}$, if present, is independently -Me, -Et, -nPr, -iPr, -nBu, -sBu, -iBu, or -tBu.

In one embodiment, $-R^{N3C}$, if present, is independently -Me or -Et.

In one embodiment, $-R^{N3D}$, if present, is independently -Me, -Et, -nPr, -iPr, -nBu, -sBu, -iBu, or -tBu.

In one embodiment, $-R^{N3D}$, if present, is independently -Me or -Et.

In one embodiment, $-R^{N3A}$ and $-R^{N3B}$, taken together with the nitrogen atom to which they are attached, form a 4-, 5-, 6-, or 7-membered non-aromatic ring having exactly one ring heteroatom, which is nitrogen, or having exactly two ring heteroatoms, which are nitrogen and oxygen, or nitrogen and nitrogen.

In one embodiment, $-R^{N3A}$ and $-R^{N3B}$, taken together with the nitrogen atom to which they are attached, form piperidino or morpholino, and is optionally substituted, for example, with one or more substituents selected from halogen (e.g., —F, —Cl) and saturated aliphatic $C_{1-4}$alkyl.

In one embodiment, $-R^{N3A}$ and $-R^{N3B}$, taken together with the nitrogen atom to which they are attached, form piperidino, N—($C_{1-3}$alkyl)piperidino, or morpholino.

In one embodiment, the compound is selected from compounds of the following formulae and salts, hydrates, and solvates thereof (e.g., pharmaceutically acceptable salts, hydrates, and solvates thereof):

| Code No. | Synthesis No. | Structure |
|---|---|---|
| JJ-001 | Synthesis 11 | [chemical structure] |
| JJ-002 | Synthesis 16 | [chemical structure] |
| JJ-003 | Synthesis 17 | [chemical structure] |
| JJ-004 | Synthesis 9 | [chemical structure] |
| JJ-005 | Synthesis 15 | [chemical structure] |

Thiol-Substituted Alkyl Compounds

It appears that the following compounds may be known:

| Code No. | Structure | Registry No. |
|---|---|---|
| PX-009 | 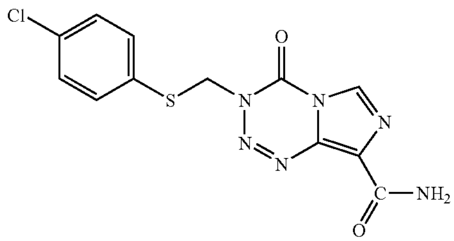 [SMILES: NC(=O)c1ncn2c(=O)n(CSc3ccc(Cl)cc3)nnc12] | 331456-39-4 |
| PX-010 | 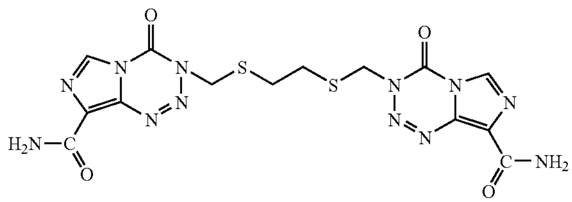 [SMILES: NC(=O)c1ncn2c(=O)n(CSCCSCn3nnc4c(C(N)=O)ncn4c3=O)nnc12] | 331456-49-6 |
| PX-011 | 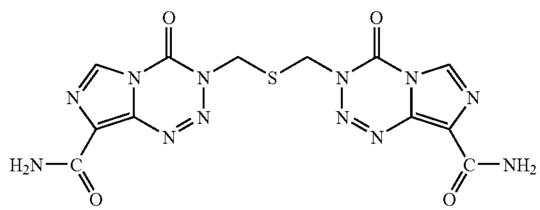 [SMILES: NC(=O)c1ncn2c(=O)n(CSCn3nnc4c(C(N)=O)ncn4c3=O)nnc12] | 331456-46-3 |
| PX-012 | 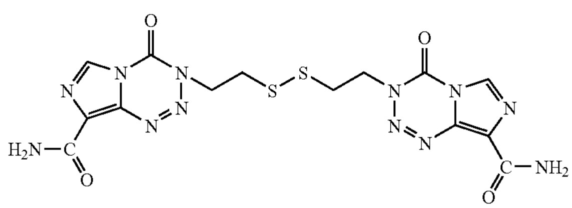 [SMILES: NC(=O)c1ncn2c(=O)n(CCSSCCn3nnc4c(C(N)=O)ncn4c3=O)nnc12] | 331456-52-1 |
| PX-013 | 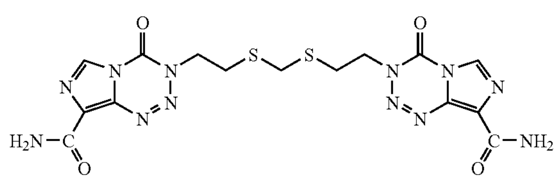 [SMILES: NC(=O)c1ncn2c(=O)n(CCSCSCCn3nnc4c(C(N)=O)ncn4c3=O)nnc12] | 331456-51-0 |
| PX-014 | 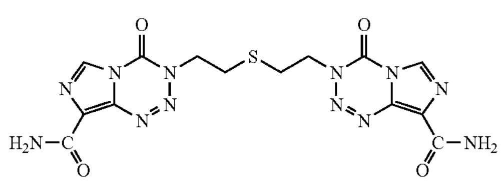 [SMILES: NC(=O)c1ncn2c(=O)n(CCSCCn3nnc4c(C(N)=O)ncn4c3=O)nnc12] | 331456-50-9 |

(For aspects of the invention relating to new uses of these compounds, see the section below entitled "Uses of Certain Known Compounds".)

In one embodiment, -Q is independently a group of the following formula:

$$R^S-S-J^4-$$

wherein:

-$J^4$- is independently saturated aliphatic $C_{1-4}$alkylene; and

—$R^S$ is independently saturated aliphatic $C_{1-4}$alkyl.

In one embodiment, -J⁴- is independently saturated aliphatic $C_{1-3}$alkylene.

In one embodiment, -J⁴- is independently saturated aliphatic $C_{1-2}$alkylene.

In one embodiment, -J⁴- is independently —CH₂—, —CH₂CH₂—, —CH₂CH₂CH₂—, —CH(CH₃)—, —CH(CH₃)CH₂—, —CH₂CH(CH₃)—, or —CH(CH₂CH₃)—.

In one embodiment, -J⁴- is independently —CH₂—, —CH₂CH₂—, or —CH₂CH₂CH₂—.

In one embodiment, -J⁴- is independently —CH₂— or —CH₂CH₂—.

In one embodiment, -J⁴- is independently —CH₂CH₂—.

In one embodiment, -J⁴- is independently —CH₂—.

In one embodiment, —R$^S$ is independently -Me, -Et, -nPr, -iPr, -nBu, -sBu, -iBu, or -tBu.

In one embodiment, —R$^S$ is independently -Me, -Et, -nPr, or -iPr.

In one embodiment, —R$^S$ is independently -Me or -Et.

In one embodiment, the compound is selected from compounds of the following formulae and salts, hydrates, and solvates thereof (e.g., pharmaceutically acceptable salts, hydrates, and solvates thereof):

| Code No. | Synthesis No. | Structure |
|---|---|---|
| KK-001 | Synthesis 6 | (structure) |
| KK-002 | Synthesis 47 | (structure) |

Carboxylic Acid-Substituted Alkyl Compounds

It appears that the following compounds may be known:

| Code No. | Structure | Registry No. |
|---|---|---|
| PX-015 | (structure) | 157466-98-3 |
| PX-016 | (structure) | 157466-97-2 |
| PX-017 | (structure) | 157466-99-4 |
| PX-018 | (structure) | 157467-00-0 |

(For aspects of the invention relating to new uses of these compounds, see the section below entitled "Uses of Certain Known Compounds".)

In one embodiment, -Q is independently a group selected from groups of the following formulae:

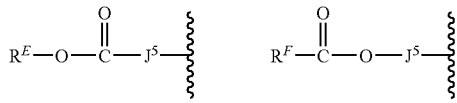

wherein:
-J⁵- is independently saturated aliphatic $C_{1-4}$alkylene, and is optionally substituted with one or more substituents independently selected from —OH and —OR$^{EER}$, wherein each —R$^{EER}$ is independently saturated aliphatic $C_{1-4}$alkyl;
—R$^E$ is independently —H or —R$^{EE}$;
—R$^F$ is independently —R$^{EE}$;
—R$^{EE}$ is independently saturated aliphatic $C_{1-4}$alkyl;
with the proviso that -Q is not —CH₂C(=O)OH or —CH₂C(=O)OCH₂CH₃.

In one embodiment, -Q is independently a group selected from groups of the following formulae:

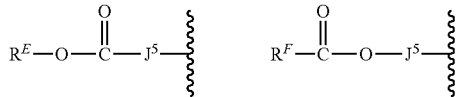

wherein:
-J⁵- is independently saturated aliphatic $C_{1-4}$alkylene;
—R$^E$ is independently —H or —R$^{EE}$;

—$R^F$ is independently —$R^{EE}$;

—$R^{EE}$ is independently saturated aliphatic $C_{1-4}$alkyl;

with the proviso that -Q is not —$CH_2C(=O)OH$ or —$CH_2C(=O)OCH_2CH_3$.

In one embodiment, -Q is independently a group of the following formula:

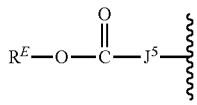

In one embodiment, -Q is independently a group of the following formula:

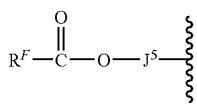

In one embodiment, -$J^5$- is independently saturated aliphatic $C_{2-4}$alkylene.

In one embodiment, -$J^5$- is independently saturated aliphatic $C_{2-3}$alkylene.

In one embodiment, -$J^5$- is independently —$CH_2$—, —$CH_2CH_2$—, —$CH_2CH_2CH_2$—, —$CH(CH_3)$—, —$CH(CH_3)CH_2$—, —$CH_2CH(CH_3)$—, or —$CH(CH_2CH_3)$—.

In one embodiment, -$J^5$- is independently —$CH_2CH_2$—, —$CH_2CH_2CH_2$—, —$CH(CH_3)$—, —$CH(CH_3)CH_2$—, —$CH_2CH(CH_3)$—, or —$CH(CH_2CH_3)$—.

In one embodiment, -$J^5$- is independently —$CH_2$—, —$CH_2CH_2$—, —$CH(CH_3)CH_2$—, —$CH_2CH(CH_3)$—, or —$CH_2CH_2CH_2$—.

In one embodiment, -$J^5$- is independently —$CH_2CH_2$—, —$CH(CH_3)CH_2$—, —$CH_2CH(CH_3)$—, or —$CH_2CH_2CH_2$—.

In one embodiment, -$J^5$- is independently —$CH_2$—, —$CH_2CH_2$— or —$CH_2CH_2CH_2$—.

In one embodiment, -$J^5$- is independently —$CH_2CH_2$— or —$CH_2CH_2CH_2$—.

In one embodiment, -$J^5$- is independently —$CH_2$—.

In one embodiment, -$J^5$- is independently —$CH_2CH_2$—.

In one embodiment, -$J^5$- is independently —$CH_2CH_2CH_2$—.

In one embodiment, -$J^5$- is independently —$CH(CH_2OH)$—.

In one embodiment, —$R^E$, if present, is independently —H.

In one embodiment, —$R^E$, if present, is independently —$R^{EE}$.

In one embodiment, —$R^{EE}$, if present, is independently -Me, -Et, -nPr, -iPr, -nBu, -sBu, -iBu, or -tBu.

In one embodiment, —$R^{EE}$, if present, is independently -Me, -Et, -nPr, or -iPr.

In one embodiment, —$R^{EE}$, if present, is independently -Me.

In one embodiment, the compound is selected from compounds of the following formulae and salts, hydrates, and solvates thereof (e.g., pharmaceutically acceptable salts, hydrates, and solvates thereof):

| Code No. | Synthesis No. | Structure |
|---|---|---|
| LL-001 | Synthesis 8 | 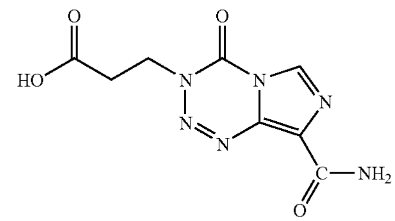 [SMILES: NC(=O)c1ncn2c(=O)n(CCC(=O)O)nnc12] |
| LL-002 | Synthesis 7 | 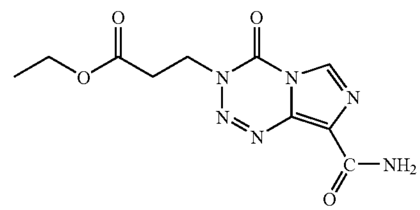 [SMILES: CCOC(=O)CCn1nnc2c(C(N)=O)ncn2c1=O] |
| LL-003 | Synthesis 38 | 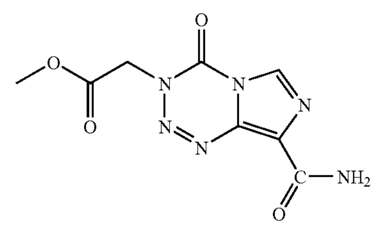 [SMILES: COC(=O)Cn1nnc2c(C(N)=O)ncn2c1=O] |
| LL-006 | Synthesis 48 | 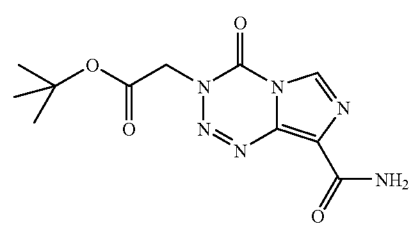 [SMILES: CC(C)(C)OC(=O)Cn1nnc2c(C(N)=O)ncn2c1=O] |
| LL-007 | Synthesis 49 | 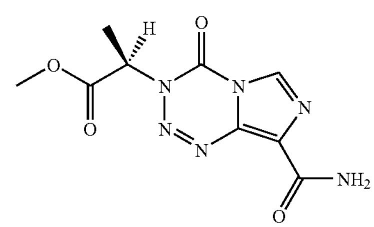 [SMILES: COC(=O)[C@@H](C)n1nnc2c(C(N)=O)ncn2c1=O] |
| LL-008 | Synthesis 50 | 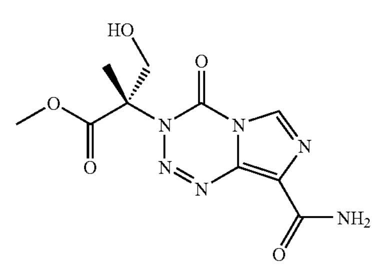 [SMILES: COC(=O)[C@](C)(CO)n1nnc2c(C(N)=O)ncn2c1=O] |

In one embodiment, the compound is selected from compounds of the following formulae and salts, hydrates, and solvates thereof (e.g., pharmaceutically acceptable salts, hydrates, and solvates thereof):

| Code No. | Synthesis No. | Structure |
|---|---|---|
| LL-004 | Synthesis 41 | (structure) |
| LL-005 | — | (structure) |

Oxy-Alkyl Compounds

It appears that the following compounds may be known:

| Code No. | Structure | Registry No. |
|---|---|---|
| PX-019 | (structure) | 331456-38-3 |
| PX-020 | (structure) | 331456-37-2 |
| PX-021 | (structure) | 172988-51-1 |
| PX-022 | (structure) | 331456-48-5 |
| PX-023 | (structure) | 331456-47-4 |

| Code No. | Structure | Registry No. |
|---|---|---|
| PX-024 | 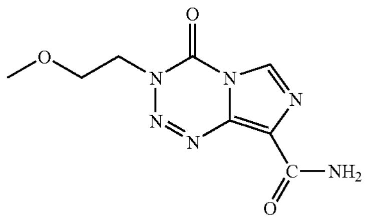 [SMILES: COCCn1nnc2c(C(N)=O)ncn2c1=O] | 85623-03-6 |

(For aspects of the invention relating to new uses of these compounds, see the section below entitled "Uses of Certain Known Compounds".)

In one embodiment, -Q is independently a group of the following formula:

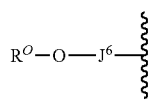

wherein:
- $-J^6-$ is independently saturated aliphatic $C_{1-4}$alkylene;
- $-R^O$ is independently $-H$ or $-R^{OO}$;
- $-R^{OO}$ is independently saturated aliphatic $C_{1-4}$alkyl, phenyl, benzyl, or $-Si(R^{SI})_3$;
- each $-R^{SI}$ is independently saturated aliphatic $C_{1-4}$alkyl;

with the proviso that -Q is not $-CH_2-O-CH_3$, $-CH_2-O-CH_2CH_3$, or $-CH_2CH_2-O-CH_3$.

In one embodiment, $-J^6-$ is independently saturated aliphatic $C_{1-3}$alkylene.

In one embodiment, $-J^6-$ is independently saturated aliphatic $C_{1-2}$alkylene.

In one embodiment, $-J^6-$ is independently saturated aliphatic $C_{2-4}$alkylene.

In one embodiment, $-J^6-$ is independently saturated aliphatic $C_{2-3}$alkylene.

In one embodiment, $-J^6-$ is independently saturated aliphatic $C_2$alkylene.

In one embodiment, $-J^6-$ is independently $-CH_2-$, $-CH_2CH_2-$, $-CH_2CH_2CH_2-$, $-CH(CH_3)-$, $-CH(CH_3)CH_2-$, $-CH_2CH(CH_3)-$, or $-CH(CH_2CH_3)-$.

In one embodiment, $-J^6-$ is independently $-CH_2-$, $-CH_2CH_2-$, or $-CH_2CH_2CH_2-$.

In one embodiment, $-J^6-$ is independently $-CH_2-$ or $-CH_2CH_2-$.

In one embodiment, $-J^6-$ is independently $-CH_2CH_2-$.

In one embodiment, $-J^6-$ is independently $-CH_2-$.

In one embodiment, $-R^O$ is independently $-H$.

In one embodiment, $-R^O$ is independently $-R^{OO}$.

In one embodiment, $-R^{OO}$, if present, is independently -Me, -Et, -nPr, -iPr, -nBu, -sBu, -iBu, or -tBu.

In one embodiment, $-R^{OO}$, if present, is independently -Me, -Et, -nPr, or -iPr.

In one embodiment, $-R^{OO}$, if present, is independently phenyl.

In one embodiment, $-R^{OO}$, if present, is independently benzyl.

In one embodiment, $-R^{OO}$, if present, is independently $-Si(R^{SI})_3$.

In one embodiment, $-R^{OO}$, if present, is independently $-Si(Me)_2(t-Bu)$.

In one embodiment, the compound is selected from compounds of the following formulae and salts, hydrates, and solvates thereof (e.g., pharmaceutically acceptable salts, hydrates, and solvates thereof):

| Code No. | Synthesis No. | Structure |
|---|---|---|
| MM-001 | Synthesis 35 | 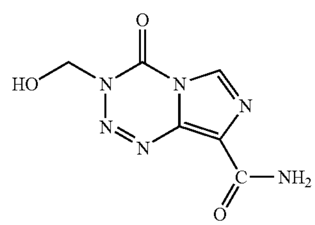 |
| MM-002 | Synthesis 33 | 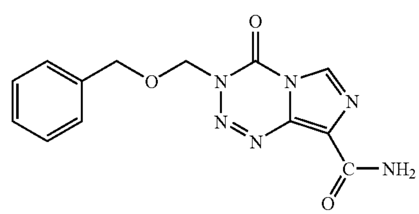 [SMILES: NC(=O)c1ncn2c(=O)n(COCc3ccccc3)nnc12] |

In one embodiment, the compound is selected from compounds of the following formulae and salts, hydrates, and solvates thereof (e.g., pharmaceutically acceptable salts, hydrates, and solvates thereof):

| Code No. | Synthesis No. | Structure |
|---|---|---|
| NN-001 | Synthesis 22 | 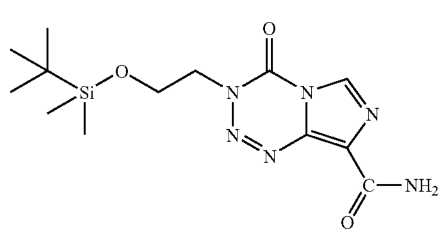 [SMILES: CC(C)(C)[Si](C)(C)OCCn1nnc2c(C(N)=O)ncn2c1=O] |

-continued

| Code No. | Synthesis No. | Structure |
|---|---|---|
| NN-002 | Synthesis 23 | (2-hydroxyethyl imidazotetrazine carboxamide structure) |

Unsubstituted Alkyl Compounds

It appears that the following compounds may be known:

(For aspects of the invention relating to new uses of these compounds, see the section below entitled "Uses of Certain Known Compounds".)

In one embodiment, -Q is independently —$CH(CH_3)_2$.

In one embodiment, the compound is selected from compounds of the following formulae and salts, hydrates, and solvates thereof (e.g., pharmaceutically acceptable salts, hydrates, and solvates thereof):

| # | Structure | Registry No. |
|---|---|---|
| PX-025 | (methyl) | 85622-93-1 (Temozolomide) |
| PX-026 | (ethyl) | 97716-74-0 |
| PX-027 | (propyl) | 85622-94-2 |
| PX-028 | (pentyl) | 112557-09-2 |
| PX-029 | (sec-butyl) | 112557-08-1 |

| Code No. | Synthesis No. | Structure |
|---|---|---|
| PP-001 | Synthesis 3 | (structure) |

Alkyl-Acyl-Substituted Alkyl Compounds

In one embodiment, -Q is independently a group of the following formula:

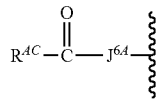

wherein:
-$J^{6A}$- is independently saturated aliphatic $C_{1-4}$alkylene; and
—$R^{AC}$ is independently saturated aliphatic $C_{1-4}$alkyl.

In one embodiment, -$J^{6A}$- is independently saturated aliphatic $C_{2-4}$alkylene.

In one embodiment, -$J^{6A}$- is independently saturated aliphatic $C_{2-3}$alkylene.

In one embodiment, -$J^{6A}$- is independently saturated aliphatic $C_{1-3}$alkylene.

In one embodiment, -$J^{6A}$- is independently saturated aliphatic $C_{1-2}$alkylene.

In one embodiment, -$J^{6A}$- is independently —$CH_2$—, —$CH_2CH_2$—, —$CH_2CH_2CH_2$—, —$CH(CH_3)$—, —$CH(CH_3)CH_2$—, —$CH_2CH(CH_3)$—, or —$CH(CH_2CH_3)$—.

In one embodiment, -$J^{6A}$- is independently —$CH_2$—, —$CH_2CH_2$—, —$CH(CH_3)CH_2$—, —$CH_2CH(CH_3)$—, or —$CH_2CH_2CH_2$—.

In one embodiment, -$J^{6A}$- is independently —$CH_2$—, —$CH_2CH_2$— or —$CH_2CH_2CH_2$—.

In one embodiment, -$J^{6A}$- is independently —$CH_2$—.

In one embodiment, —$R^{AC}$ is independently -Me, -Et, -nPr, -iPr, -nBu, -sBu, -iBu, or -tBu.

In one embodiment, —$R^{AC}$ is independently -Me, -Et, -nPr, or -iPr.

In one embodiment, —$R^{AC}$ is independently -Me.

In one embodiment, the compound is selected from compounds of the following formulae and salts, hydrates, and solvates thereof (e.g., pharmaceutically acceptable salts, hydrates, and solvates thereof):

| Code No. | Synthesis No. | Structure |
|---|---|---|
| QQ-001 | Synthesis 39 | (structure) |

Halo-Alkyl Compounds

It appears that the following compounds may be known:

| Code No. | Structure | Registry No. |
|---|---|---|
| PX-030 | (structure) | 331456-36-1 |
| PX-031 | (structure) | 208107-15-1 |
| PX-032 | (structure) | 85622-95-3 |
| PX-033 | (structure) | 85623-01-4 |
| PX-034 | (structure) | 85622-97-5 |
| PX-035 | (structure) | 85622-98-6 |

(For aspects of the invention relating to new uses of these compounds, see the section below entitled "Uses of Certain Known Compounds".)

In one embodiment, -Q is independently a group of the formula:

wherein:
  $R^X$ is independently saturated aliphatic $C_{1-6}$hydrocarbyl;
  n is independently 1, 2, 3, 4, or 5; and
  each —X is independently —F, —Cl, —Br, or —I;
with the proviso that -Q is not: —CH$_2$Cl, —CH$_2$CF$_3$, —CH$_2$CH$_2$Cl, —CH$_2$CH$_2$Br, —CH$_2$CH$_2$CH$_2$Cl, or —CH$_2$CHClCH$_2$Cl.

In this context, the term "hydrocarbyl" means a moiety having only carbon atoms, or only carbon atoms and hydrogen atoms. The prefix (e.g., $C_{1-6}$) indicates the number of carbon atoms in the moiety.

For example, when n is 1, then $R^X$ is saturated aliphatic $C_1$ alkylene, for example, the —CH$_2$CH$_2$— in the group —CH$_2$CH$_2$F.

For example, when n is 2, then $R^X$ is saturated aliphatic $C_{1-6}$alk-tri-yl, for example, the —CH$_2$CH< in the group —CH$_2$CHF$_2$.

In one embodiment, $R^X$ is independently saturated aliphatic $C_{2-6}$hydrocarbyl.
In one embodiment, $R^X$ is independently saturated aliphatic $C_{3-6}$hydrocarbyl.
In one embodiment, $R^X$ is independently saturated aliphatic $C_{1-4}$hydrocarbyl.
In one embodiment, $R^X$ is independently saturated aliphatic $C_{2-4}$hydrocarbyl.
In one embodiment, $R^X$ is independently saturated aliphatic $C_{3-4}$hydrocarbyl.
In one embodiment, $R^X$ is independently saturated linear $C_{2-6}$hydrocarbyl.
In one embodiment, $R^X$ is independently saturated linear $C_{3-6}$hydrocarbyl.
In one embodiment, $R^X$ is independently saturated linear $C_{1-4}$hydrocarbyl.
In one embodiment, $R^X$ is independently saturated linear $C_{2-4}$hydrocarbyl.
In one embodiment, $R^X$ is independently saturated linear $C_{3-4}$hydrocarbyl.
In one embodiment, $R^X$ is independently saturated aliphatic $C_2$hydrocarbyl.
In one embodiment, $R^X$ is independently saturated aliphatic $C_3$hydrocarbyl.
In one embodiment, $R^X$ is independently saturated aliphatic $C_4$hydrocarbyl.
In one embodiment, $R^X$ is independently saturated aliphatic $C_5$hydrocarbyl.
In one embodiment, $R^X$ is independently saturated aliphatic $C_6$hydrocarbyl.
In one embodiment, $R^X$ is independently saturated linear $C_2$hydrocarbyl.
In one embodiment, $R^X$ is independently saturated linear $C_3$hydrocarbyl.
In one embodiment, $R^X$ is independently saturated linear $C_4$hydrocarbyl.
In one embodiment, $R^X$ is independently saturated linear $C_5$hydrocarbyl.
In one embodiment, $R^X$ is independently saturated linear $C_6$hydrocarbyl.

In one embodiment, n is 1.
In one embodiment, n is 2.
In one embodiment, n is 3.
In one embodiment, n is 4.
In one embodiment, n is 5.
In one embodiment, if n is more than 1, then each —X is the same.
In one embodiment, each —X is —F.
In one embodiment, each —X is —Cl.
In one embodiment, each —X is —Br.
In one embodiment, each —X is —I.
In one embodiment, n is 2 and each —X is —F.
In one embodiment, n is 3 and each —X is —F.
In one embodiment, n is 1 and —X is —F.
In one embodiment, n is 1 and —X is —Cl.
In one embodiment, n is 1 and —X is —Br.
In one embodiment, n is 1 and —X is —I.
In one embodiment, -Q is independently:
  —CH$_2$F, —CH$_2$Br, —CH$_2$I,
  —CH$_2$CH$_2$I,
  —CH$_2$CH$_2$CH$_2$F, —CH$_2$CH$_2$CH$_2$Br, —CH$_2$CH$_2$CH$_2$I,
  —CH$_2$CHF$_2$, —CH$_2$CH$_2$CHF$_2$, or
  —CH$_2$CH$_2$CF$_3$.
In one embodiment, -Q is independently —CH$_2$CHF$_2$.

In one embodiment, the compound is selected from compounds of the following formulae and salts, hydrates, and solvates thereof (e.g., pharmaceutically acceptable salts, hydrates, and solvates thereof):

| Code No. | Synthesis No. | Structure |
|---|---|---|
| RR-001 | — | ![structure with F] |
| RR-002 | — | ![structure with Br] |
| RR-003 | — | ![structure with I] |

| Code No. | Synthesis No. | Structure |
|---|---|---|
| RR-004 | — | 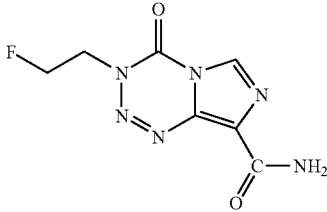 |
| RR-005 | — | 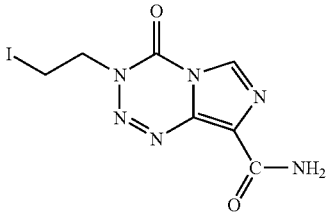 |
| RR-006 | — | 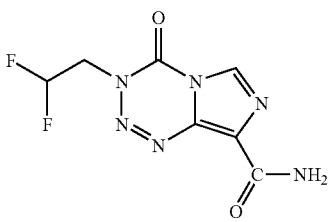 [SMILES: NC(=O)c1ncn2c(=O)n(CCF)nnc12] |

Nitro-Alkyl Compounds

It appears that the following compound may be known:

| Code No. | Structure | Registry No. |
|---|---|---|
| PX-036 | 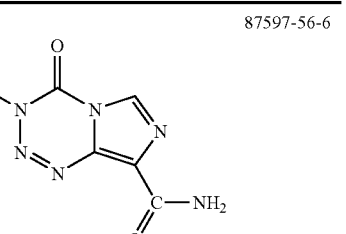 | 87597-56-6 |

(For aspects of the invention relating to new uses of these compounds, see the section below entitled "Uses of Certain Known Compounds".)

In one embodiment, -Q is independently a group of the following formula:

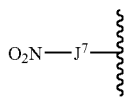

wherein -$J^7$- is independently saturated aliphatic $C_{1-4}$alkylene.

In one embodiment, -$J^7$- is independently saturated aliphatic $C_{2-4}$alkylene.

In one embodiment, -$J^7$- is independently saturated aliphatic $C_{2-3}$alkylene.

In one embodiment, -$J^7$- is independently saturated aliphatic $C_{1-3}$alkylene.

In one embodiment, -$J^7$- is independently saturated aliphatic $C_{1-2}$alkylene.

In one embodiment, -$J^7$- is independently —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, or —CH(CH$_2$CH$_3$)—.

In one embodiment, -$J^7$- is independently —CH$_2$—, —CH$_2$CH$_2$—, —CH(CH$_3$)CH$_2$—, —CH$_2$CH(CH$_3$)—, or —CH$_2$CH$_2$CH$_2$—.

In one embodiment, -$J^7$- is independently —CH$_2$—, —CH$_2$CH$_2$— or —CH$_2$CH$_2$CH$_2$—.

In one embodiment, -$J^7$- is independently —CH$_2$—.

In one embodiment, the compound is selected from compounds of the following formulae and salts, hydrates, and solvates thereof (e.g., pharmaceutically acceptable salts, hydrates, and solvates thereof):

| Code No. | Synthesis No. | Structure |
|---|---|---|
| SS-001 | — | 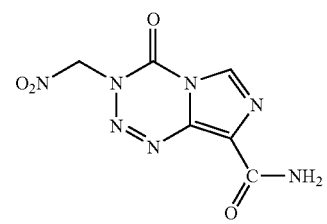 [SMILES: NC(=O)c1ncn2c(=O)n(C[N+](=O)[O-])nnc12] |

Cyano-Alkyl Compounds

It appears that the following compound may be known:

| Code No. | Structure | Registry No. |
|---|---|---|
| PX-037 | 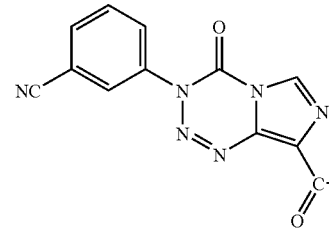 | 87579-57-7 |

(For aspects of the invention relating to new uses of these compounds, see the section below entitled "Uses of Certain Known Compounds".)

In one embodiment, -Q is independently a group of the following formula:

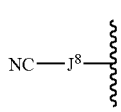

wherein -$J^8$- is independently saturated aliphatic $C_{1-4}$alkylene.

In one embodiment, -$J^8$- is independently saturated aliphatic $C_{2-4}$alkylene.

In one embodiment, -$J^8$- is independently saturated aliphatic $C_{2-3}$alkylene.

In one embodiment, -J$^8$- is independently saturated aliphatic C$_{1-3}$alkylene.

In one embodiment, -J$^8$- is independently saturated aliphatic C$_{1-2}$alkylene.

In one embodiment, -J$^8$- is independently —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, or —CH(CH$_2$CH$_3$)—.

In one embodiment, -J$^8$- is independently —CH$_2$—, —CH$_2$CH$_2$—, —CH(CH$_3$)CH$_2$—, —CH$_2$CH(CH$_3$)—, or —CH$_2$CH$_2$CH$_2$—.

In one embodiment, -J$^8$- is independently —CH$_2$—, —CH$_2$CH$_2$— or —CH$_2$CH$_2$CH$_2$—.

In one embodiment, -J$^8$- is independently —CH$_2$—.

In one embodiment, the compound is selected from compounds of the following formulae and salts, hydrates, and solvates thereof (e.g., pharmaceutically acceptable salts, hydrates, and solvates thereof):

| Code No. | Synthesis No. | Structure |
|---|---|---|
| TT-001 | — | (structure) |

Sulfonyl-Alkyl Compounds

In one embodiment, -Q is independently a group of the following formula:

$$R^{SO}-S(=O)_t-J^9-\xi$$

wherein:
-J$^9$- is independently saturated aliphatic C$_{1-4}$alkylene;
t is independently 1 or 2; and
—R$^{SO}$ is independently saturated aliphatic C$_{1-4}$alkyl, phenyl, or benzyl, wherein said phenyl and benzyl are independently optionally substituted with one or more substituents selected from —F, —Cl, —Br, —I, —R$^{SOR}$, —CF$_3$, —OH, —OR$^{SOR}$, and —OCF$_3$, wherein each —R$^{SOR}$ is independently saturated aliphatic C$_{1-4}$alkyl.

In one embodiment, t is independently 1.

In one embodiment, t is independently 2.

In one embodiment, -J$^9$- is independently saturated aliphatic C$_{1-3}$alkylene.

In one embodiment, -J$^9$- is independently saturated aliphatic C$_{1-2}$alkylene.

In one embodiment, -J$^9$- is independently —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, or —CH(CH$_2$CH$_3$)—.

In one embodiment, -J$^9$- is independently —CH$_2$— or —CH$_2$CH$_2$—.

In one embodiment, -J$^9$- is independently —CH$_2$—.

In one embodiment, -J$^9$- is independently —CH$_2$CH$_2$—.

In one embodiment, —R$^{SO}$ is independently saturated aliphatic C$_{1-4}$alkyl.

In one embodiment, —R$^{SO}$ is independently -Me or -Et.

In one embodiment, —R$^{SO}$ is independently -Me.

In one embodiment, the compound is selected from compounds of the following formulae and salts, hydrates, and solvates thereof (e.g., pharmaceutically acceptable salts, hydrates, and solvates thereof):

| Code No. | Synthesis No. | Structure |
|---|---|---|
| UU-001 | Synthesis 51 | (structure) |
| UU-002 | Synthesis 52 | (structure) |
| UU-003 | Synthesis 53 | (structure) |

Phosphate-Alkyl Compounds

In one embodiment, -Q is independently a group of the following formula:

$$\begin{array}{c} R^{PR}\diagdown O \\ O=P-J^{10}-\xi \\ R^{PR}\diagup O \end{array}$$

wherein:
-J$^{10}$- is independently saturated aliphatic C$_{1-4}$alkylene;
each —R$^{PR}$ is independently saturated aliphatic C$_{1-4}$alkyl, phenyl, or benzyl, wherein said phenyl and benzyl are independently optionally substituted with one or more substituents selected from —F, —Cl, —Br, —I, —R$^{PRR}$, —CF$_3$, —OH, —OR$^{PRR}$, and —OCF$_3$, wherein each —R$^{PRR}$ is independently saturated aliphatic C$_{1-4}$alkyl.

In one embodiment, -J$^{10}$- is independently saturated aliphatic C$_{1-3}$alkylene.

In one embodiment, -J$^{10}$- is independently saturated aliphatic C$_{1-2}$alkylene.

In one embodiment, -J$^{10}$- is independently —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, or —CH(CH$_2$CH$_3$)—.

In one embodiment, -J$^{10}$- is independently —CH$_2$— or —CH$_2$CH$_2$—.

In one embodiment, -J$^{10}$- is independently —CH$_2$—.

In one embodiment, -J$^{10}$- is independently —CH$_2$CH$_2$—.

In one embodiment, each —$R^{PR}$ is independently saturated aliphatic $C_{1-4}$alkyl.

In one embodiment, each —$R^{PR}$ is independently -Me or -Et.

In one embodiment, each —$R^{PR}$ is independently -Et.

In one embodiment, the compound is selected from compounds of the following formulae and salts, hydrates, and solvates thereof (e.g., pharmaceutically acceptable salts, hydrates, and solvates thereof):

| Code No. | Synthesis No. | Structure |
|---|---|---|
| VV-001 | Synthesis 54 | 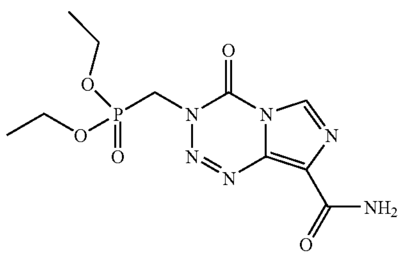 [SMILES: CCOP(=O)(Cn1nnc2c(C(N)=O)ncn2c1=O)OCC] |

Carbamate-Alkyl Compounds

In one embodiment, -Q is independently a group of the following formula:

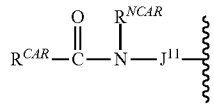

wherein:
- -$J^{11}$- is independently saturated aliphatic $C_{1-4}$alkylene; and —$R^{NCAR}$ is independently —H or —$R^{CAR}$;
- each —$R^{CAR}$ is independently saturated aliphatic $C_{1-4}$alkyl, phenyl, benzyl, fluorenyl, or —$CH_2$-fluorenyl, wherein said phenyl, benzyl, and fluorenyl are independently optionally substituted with one or more substituents selected from —F, —Cl, —Br, —I, —$R^{CARR}$, —$CF_3$, —OH, —$OR^{CARR}$, and —$OCF_3$, wherein each —$R^{CARR}$ is independently saturated aliphatic $C_{1-4}$alkyl.

In one embodiment, -$J^{11}$- is independently saturated aliphatic $C_{1-3}$alkylene.

In one embodiment, -$J^{11}$- is independently saturated aliphatic $C_{1-2}$alkylene.

In one embodiment, -$J^{11}$- is independently —$CH_2$—, —$CH_2CH_2$—, —$CH_2CH_2CH_2$—, —$CH(CH_3)$—, —$CH(CH_3)CH_2$—, —$CH_2CH(CH_3)$—, or —$CH(CH_2CH_3)$—.

In one embodiment, -$J^{11}$- is independently —$CH_2$— or —$CH_2CH_2$—.

In one embodiment, -$J^{11}$- is independently —$CH_2$—.

In one embodiment, -$J^{11}$- is independently —$CH_2CH_2$—.

In one embodiment, —$R^{NCAR}$ is independently —H.

In one embodiment, each —$R^{CAR}$ is independently saturated aliphatic $C_{1-4}$alkyl.

In one embodiment, each —$R^{CAR}$ is independently phenyl, benzyl, fluorenyl, or —$CH_2$-fluorenyl, wherein said phenyl, benzyl, and fluorenyl are independently optionally substituted with one or more substituents selected from —F, —Cl, —Br, —I, —$R^{CARR}$, —$CF_3$, —OH, —$OR^{CARR}$, and —$OCF_3$, wherein each —$R^{CARR}$ is independently saturated aliphatic $C_{1-4}$alkyl.

In one embodiment, each —$R^{CAR}$ is independently fluorenyl or —$CH_2$-fluorenyl, wherein said fluorenyl is independently optionally substituted with one or more substituents selected from —F, —Cl, —Br, —I, —$R^{CARR}$, —$CF_3$, —OH, —$OR^{CARR}$, and —$OCF_3$, wherein each —$R^{CARR}$ is independently saturated aliphatic $C_{1-4}$alkyl.

In one embodiment, each —$R^{CAR}$ is independently 9H-fluoren-9-yl or —$CH_2$-(9H-fluoren-9-yl), wherein said 9H-fluoren-9-yl is independently optionally substituted with one or more substituents selected from —F, —Cl, —Br, —I, —$R^{CARR}$, —$CR_3$, —OH, —$OR^{CARR}$, and —$OCF_3$, wherein each —$R^{CARR}$ is independently saturated aliphatic $C_{1-4}$alkyl.

In one embodiment, the compound is selected from compounds of the following formulae and salts, hydrates, and solvates thereof (e.g., pharmaceutically acceptable salts, hydrates, and solvates thereof):

| Code No. | Synthesis No. | Structure |
|---|---|---|
| WW-001 | Synthesis 55 | 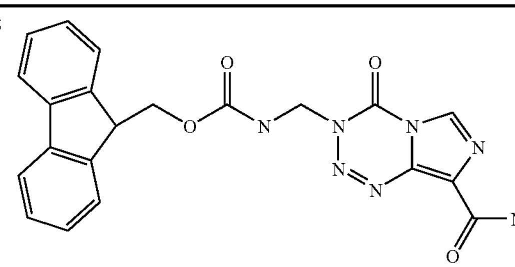 |

Oxime-Alkyl Compounds

In one embodiment, -Q is independently a group of the following formula:

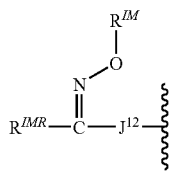

wherein:
- -$J^{12}$- is independently saturated aliphatic $C_{1-4}$alkylene; and —$R^{IM}$ is independently —H or —$R^{IMR}$;

each —$R^{IMR}$ is independently saturated aliphatic $C_{1-4}$alkyl, phenyl, or benzyl, wherein said phenyl and benzyl are independently optionally substituted with one or more substituents selected from —F, —Cl, —Br, —I, —$R^{IMRR}$, —$CF_3$, —OH, —$OR^{IMRR}$, and —$OCF_3$, wherein each —$R^{IMRR}$ is independently saturated aliphatic $C_{1-4}$alkyl.

In one embodiment, -$J^{12}$- is independently saturated aliphatic $C_{1-3}$alkylene.

In one embodiment, -$J^{12}$- is independently saturated aliphatic $C_{1-2}$alkylene.

In one embodiment, -$J^{12}$- is independently —$CH_2$—, —$CH_2CH_2$—, —$CH_2CH_2CH_2$—, —$CH(CH_3)$—, —$CH(CH_3)CH_2$—, —$CH_2CH(CH_3)$—, or —$CH(CH_2CH_3)$—.

In one embodiment, -$J^{12}$- is independently —$CH_2$— or —$CH_2CH_2$—.

In one embodiment, -$J^{12}$- is independently —$CH_2$—.
In one embodiment, -$J^{12}$- is independently —$CH_2CH_2$—.
In one embodiment, -$J^{12}$- is independently —H.
In one embodiment, -$J^{12}$- is independently —$R^{IMR}$.

In one embodiment, each —$R^{IM}$ is independently saturated aliphatic $C_{1-4}$alkyl.

In one embodiment, each —$R^{IMR}$ is independently -Me or -Et.

In one embodiment, the compound is selected from compounds of the following formulae and salts, hydrates, and solvates thereof (e.g., pharmaceutically acceptable salts, hydrates, and solvates thereof):

| Code No. | Synthesis No. | Structure |
|---|---|---|
| XX-001 | Synthesis 56 | (structure shown) |

Molecular Weight

In one embodiment, the 3TM compound has a molecular weight of from 200 to 1200.

In one embodiment, the bottom of range is from 210, 220, 225, 250, 275, 300, or 350.

In one embodiment, the top of range is 1100, 1000, 900, 800, 700, or 600.

In one embodiment, the range is 220 to 600.

Combinations

Each and every compatible combination of the embodiments described above is explicitly disclosed herein, as if each and every combination was individually and explicitly recited.

Substantially Purified Forms

One aspect of the present invention pertains to 3TM compounds, as described herein, in substantially purified form and/or in a form substantially free from contaminants.

In one embodiment, the compound is in a substantially purified form with a purity of least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form.

For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to a equimolar mixture of enantiomers (i.e., a racemic mixture, a racemate). In one embodiment, the substantially purified form refers to one enantiomer, e.g., optically pure enantiomer.

In one embodiment, the compound is in a form substantially free from contaminants wherein the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the compound is in a substantially purified form with an optical purity of at least 60% (i.e., 60% of the compound, on a molar basis, is the desired enantiomer, and 40% is the undesired enantiomer), e.g., at least 70%, e.g., at least 80%, e.g., at least 90%, e.g., at least 95%, e.g., at least 97%, e.g., at least 98%, e.g., at least 99%.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

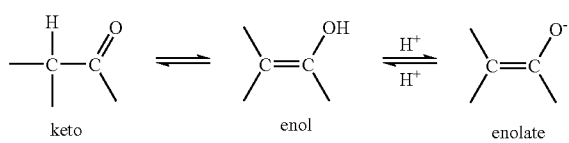

keto ⇌ enol ⇌ enolate

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Hydrates and Solvates

It may be convenient or desirable to prepare, purify, and/or handle a corresponding hydrate or solvate of the compound (e.g., pharmaceutically acceptable hydrates or solvates of the compound). The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes hydrate and solvate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 4th Edition; John Wiley and Sons, 2006).

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O.).

For example, a carboxylic acid group may be protected as an ester for example, as: an $C_{1-7}$alkyl ester (e.g., a methyl ester; a t-butyl ester); a $C_{1-7}$haloalkyl ester (e.g., a $C_{1-7}$trihaloalkyl ester); a tri$C_{1-7}$alkylsilyl-$C_{1-7}$alkyl ester; or a $C_{5-20}$aryl-$C_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

For example, a carbonyl group may be protected as an oxime (—C(=NOH)—) or a substituted oxime (—C(=NOR)—), for example, where R is saturated aliphatic $C_{1-4}$alkyl.

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Several methods for the chemical synthesis of 3TM compounds of the present invention are described herein. These and/or other well known methods may be modified and/or adapted in known ways in order to facilitate the synthesis of additional compounds within the scope of the present invention.

In one approach, a suitable isocyanate is reacted with 5-diazoimidazole-4-carboxamide (a well-known reagent) to give the corresponding 3-substituted imidazotetrazine, for example as illustrated in the following scheme.

Scheme 1

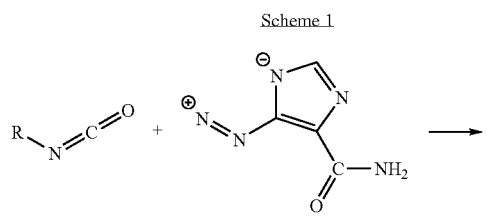

-continued

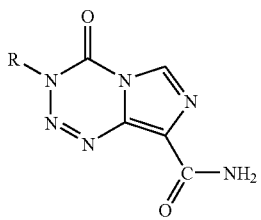

See, for example, Wang, Y., et al., 1998, "Antitumour imidazotetrazines. Part 36. Conversion of 5-amino-imidazole-4-carboxamide to imidazo[5,1-d][1,2,3,5]tetrazin-4(3H)-ones and imidazo[1,5-a][1,3,5]triazin-4(3H)-ones related in structure to the antitumour agents temozolomide and mitozolomide," *J. Chem. Soc., Perkin Trans* 1, Vol. 10, pp. 1669-1675;

Stevens, M. F. G., et al., 1984, "Antitumour imidazotetrazines. Part 1. Synthesis and chemistry of 8-carbamoyl-3-(2-chloroethyl)imidazo[1,5-d]-1,2,3,5-tetrazin-4(3H)-one, a novel broad spectrum antitumour agent", *J. Med. Chem.*, Vol. 27, pp. 196-201.

Suitable isocyanates may be obtained from commercial sources, or prepared using known methods, or by adapting known methods in known ways. For example, methods for preparing certain isocyanates are described in WO 96/27588.

The classical routes to isocyanates are treatment of a primary amine with phosgene, or a phosgene equivalent, and the Curtius rearrangement of an acyl azide (see, e.g., Ozaki, S., 1972, *Chem. Rev.*, Vol. 72, pp. 457-496; Saunders, J. H., et al., 1948, *Chem. Rev.*, Vol. 43, pp. 203-218). Acyl azides are commonly prepared by the treatment of an acid chloride with sodium azide or, more conveniently, are prepared directly from the carboxylic acid using diphenylphosphoryl azide (dppa) (see, e.g., Shioiri, T., et al., 1972, *J. Am. Chem. Soc.*, Vol. 94, pp. 6203-6205) and are not normally isolated.

In another approach, the 3-(hydroxymethyl) compound (3-hydroxymethyl-4-oxo-3,4-dihydro-imidazo[5,1-d][1,2,3,5]tetrazine-8-carboxylic acid amide) is used as a key intermediate. This key intermediate may be prepared by methods described here, and illustrated, for example, in the following scheme.

Scheme 2

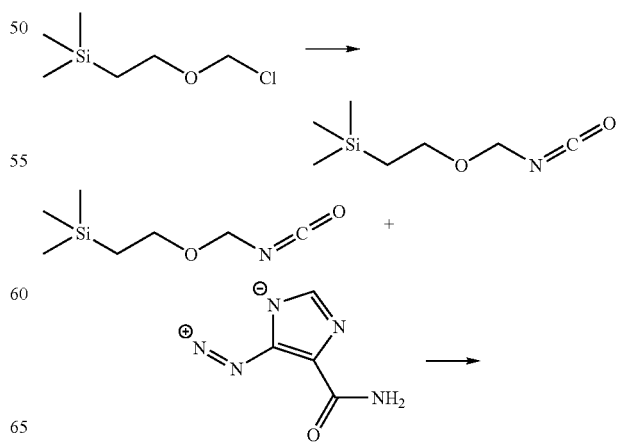

-continued

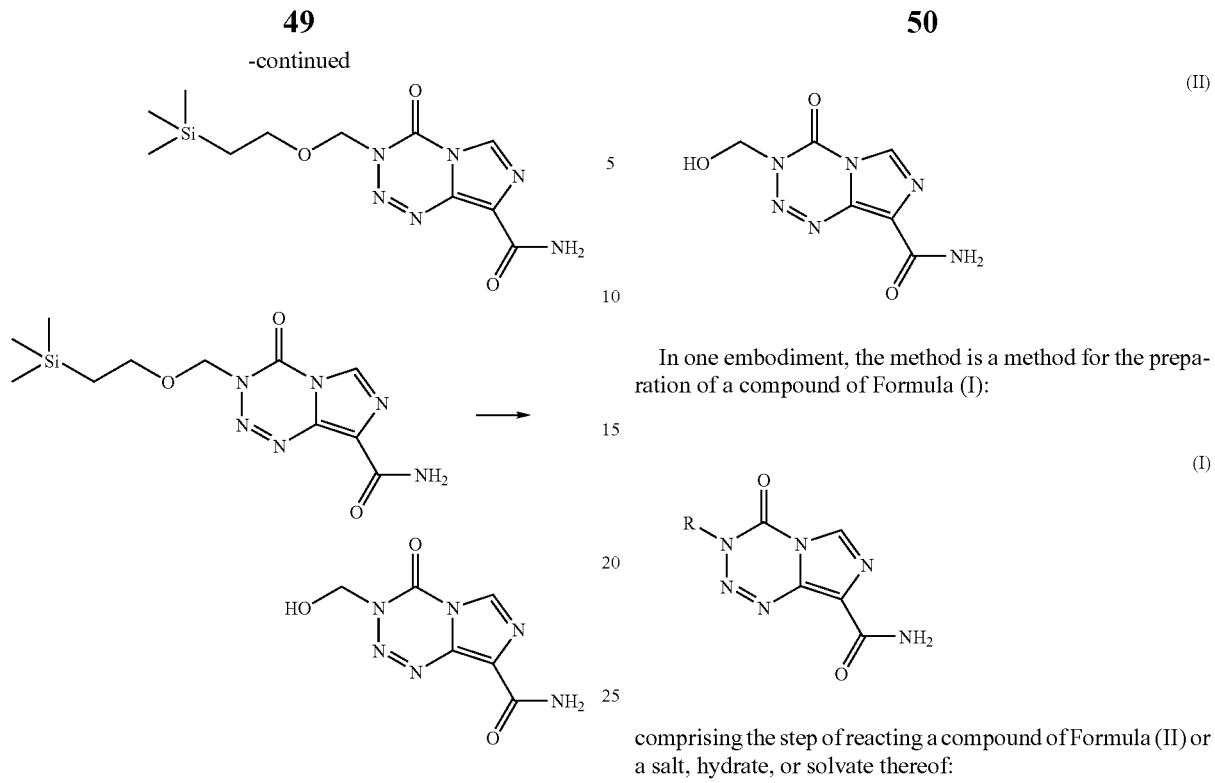

This key intermediate may then be used to prepare a range of other 3-substituted compounds by reaction with a suitable halide (e.g., R—X, where X is, for example, —I), for example, in the presence of a suitable base. An example of this method is illustrated in the following scheme.

Scheme 3

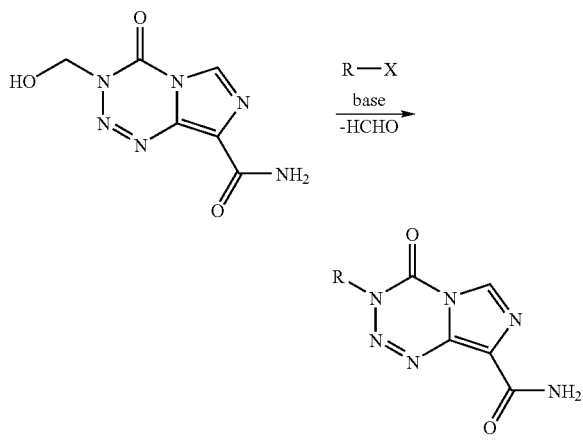

This approach has the particular advantage that is employs halides (e.g., R—X) instead of isocyanates (e.g., R—N=C=O). A wider variety of halides is known and/or can be relatively easily prepared, as compared to the corresponding isocyanates. (Of course, an isocyanate is used in the preparation of the key intermediate, but it is an isocyanate that is known and relatively easy to prepare and handle.)

Thus, another aspect of the present invention is a method of synthesis that employs the key intermediate described above, specifically, a compound of Formula (II) or a salt, hydrate, or solvate thereof:

(II)

In one embodiment, the method is a method for the preparation of a compound of Formula (I):

(I)

comprising the step of reacting a compound of Formula (II) or a salt, hydrate, or solvate thereof:

(II)

with a compound of the formula R—X, wherein: —R is a group having: from 1 to 15 carbon atoms; at least one hydrogen atom; from 0 to 6 atoms selected from N, O, S, F, Cl, Br, I, and P; and at least one non-aromatic carbon atom; —X is a halogen atom; and —X is attached to said non-aromatic carbon atom;
under conditions suitable to form said compound of Formula (I).

In one embodiment, the compound of the formula R—X is a compound of the formula R—X wherein: —R is a group having: from 1 to 15 carbon atoms; at least one hydrogen atom; from 0 to 6 atoms selected from N, O, S, F, Cl, Br, I, and P; and at least one non-aromatic fully saturated carbon atom; —X is a halogen atom; and —X is attached to said non-aromatic fully saturated carbon atom (as in, for example, n-hexyl-iodide).

In one embodiment, the compound of the formula R—X is a compound of the formula $R^{T1}$—$R^{ALK}$—X, wherein:
 —X is independently a halogen atom;
 —$R^{ALK}$— is independently saturated aliphatic $C_{1-4}$alkylene that is optionally substituted with one or more fluorine atoms;
 —$R^{T1}$ is independently —OH, —$OR^{T2}$, —C(=O)OH, —C(=O)$OR^{T2}$, —C(=O)$R^{T2}$, —C(=NOH)$R^{T2}$, —C(=$NOR^{T2}$)$R^{T2}$, —$NO_2$, —CN, —S(=O)$R^{T2}$, —S(=O)$_2 R^{T2}$, —$R^{T3}$, or —$R^{T4}$;

each —$R^{T2}$ is independently saturated aliphatic $C_{1-4}$alkylene, phenyl, or benzyl;

—$R^{T3}$ is independently non-aromatic $C_{5-6}$heterocyclyl, and is optionally substituted (e.g., with one or more groups selected from —F, —Cl, —Br, —I, —OH, and —OMe);

—$R^{T4}$ is independently $C_{5-6}$heteroaryl, and is optionally substituted (e.g., with one or more groups selected from —F, —Cl, —Br, —I, —OH, and —OMe).

In one embodiment, —X is independently —F, —Cl, —Br, or —I.

In one embodiment, —X is independently —Cl, —Br, or —I.

In one embodiment, —X is independently —Cl.

In one embodiment, —X is independently —Br.

In one embodiment, —X is independently —I.

In one embodiment, —$R^{ALK}$— is independently —$CH_2$—, —$CH_2CH_2$—, —$CH_2CH_2CH_2$—, —$CH(CH_3)$—, —$CH(CH_3)CH_2$—, —$CH_2CH(CH_3)$—, —$CH(CH_2CH_3)$—, —CHF—, —$CHFCH_2$—, or —$CH_2CF$—.

In one embodiment, —$R^{ALK}$— is independently —$CH_2$— or —CHF—.

In one embodiment, —$R^{T1}$ is independently —OH and —$OR^{T2}$.

In one embodiment, —$R^{T1}$ is independently —C(=O)OH and —C(=O)$OR^{T2}$.

In one embodiment, —$R^{T1}$ is independently —C(=O)$R^{T2}$, —C(=NOH)$R^{T2}$, or —C(=$NOR^{T2}$)$R^{T2}$.

In one embodiment, —$R^{T1}$ is independently —$NO_2$.

In one embodiment, —$R^{T1}$ is independently —CN.

In one embodiment, —$R^{T1}$ is independently —S(=O)$R^{T2}$ or —$S(=O)_2R^{T2}$.

In one embodiment, —$R^{T1}$ is independently —$S(=O)_2R^{T2}$.

In one embodiment, —$R^{T1}$ is independently —$R^{T3}$ and —$R^{T4}$.

In one embodiment, —$R^{T1}$ is independently —$R^{T3}$.

In one embodiment, —$R^{T1}$ is independently —$R^{T4}$.

In one embodiment, each —$R^{T2}$ is independently saturated aliphatic $C_{1-4}$alkylene.

In one embodiment, each —$R^{T2}$ is independently -Me or -Et.

In one embodiment, —$R^{T3}$ is independently azetidinyl, pyrrolidinyl, imidazolidinyl, pyrazolidinyl, piperidinyl, piperazinyl, morpholinyl, azepinyl, diazepinyl, tetrahydrofuranyl, tetrahydropyranyl, dioxolanyl, or dioxanyl, and is optionally substituted (e.g., with one or more groups selected from —F, —Cl, —Br, —I, —OH, and —OMe).

In one embodiment, —$R^{T3}$ is independently tetrahydrofuranyl or dioxolanyl, and is optionally substituted.

In one embodiment, —$R^{T3}$ is independently tetrahydrofuranyl or [1,3]-dioxolanyl, and is optionally substituted.

In one embodiment, —$R^{T3}$ is independently tetrahydrofuran-2-yl or [1,3]-dioxolan-2-yl, and is optionally substituted.

In one embodiment, —$R^{T4}$ is independently furanyl, thienyl, pyrrolyl, imidazolyl, pyrazolyl, triazolyl, tetrazolyl, oxazolyl, isoxazolyl, thiazolyl, isothiazolyl, oxadiazolyl, pyridinyl, pyrimidinyl, pyrazinyl, or pyridazinyl, and is optionally substituted (e.g., with one or more groups selected from —F, —Cl, —Br, —I, —OH, and —OMe).

In one embodiment, —$R^{T4}$ is independently [1,2,4]-oxadiazolyl, and is optionally substituted.

In one embodiment, —$R^{T4}$ is independently [1,2,4]-oxadiazol-3-yl, and is optionally substituted.

In one embodiment, the step of reacting a compound of Formula (II) or a salt, hydrate, or solvate thereof with a compound of the formula R—X is performed in the presence of a base.

In one embodiment, the base is an organic base.

In one embodiment, the base is a non-nucleophilic organic base.

In one embodiment, the base is 1,8-diazabicycloundec-7-ene (DBU) or diisopropylethylamine (DIPEA).

In one embodiment, the base is 1,8-diazabicycloundec-7-ene (DBU).

In one embodiment, the step of reacting a compound of Formula (II) or a salt, hydrate, or solvate thereof with a compound of the formula R—X is performed in a reaction solvent.

In one embodiment, the reaction solvent comprises acetonitrile.

In one embodiment, the reaction solvent is acetonitrile.

In one embodiment, the step of reacting a compound of Formula (II) or a salt, hydrate, or solvate thereof with a compound of the formula R—X is performed at a reaction temperature of about 0° C. to about 30° C.

In one embodiment, the step of reacting a compound of Formula (II) or a salt, hydrate, or solvate thereof with a compound of the formula R—X is performed for a reaction time of about 1 to about 48 hours.

In one embodiment, the step of reacting a compound of Formula (II) or a salt, hydrate, or solvate thereof with a compound of the formula R—X is followed by a step of acidifying the resulting reaction mixture.

In one embodiment, the step of acidifying is by addition of acid.

In one embodiment, the step of acidifying is by addition of aqueous acid.

In one embodiment, the step of acidifying is by addition of aqueous HCl.

Another aspect of the present invention pertains to a compound obtained by such a method of synthesis.

Compositions

One aspect of the present invention pertains to a composition (e.g., a pharmaceutical composition) comprising a 3TM compound, as described herein, and a pharmaceutically acceptable carrier, diluent, or excipient.

Another aspect of the present invention pertains to a method of preparing a composition (e.g., a pharmaceutical composition) comprising admixing a 3TM compound, as described herein, and a pharmaceutically acceptable carrier, diluent, or excipient.

Uses

The 3TM compounds described herein are useful, for example, in the treatment of proliferative disorders, such as, for example, cancer, etc.

Use in Methods of Inhibiting Cell Proliferation, Etc.

The 3TM compounds described herein, e.g., (a) regulate (e.g., inhibit) cell proliferation; (b) inhibit cell cycle progression; (c) promote apoptosis; or (d) a combination of one or more of these.

One aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of a 3TM compound, as described herein.

In one embodiment, the method is a method of regulating (e.g., inhibiting) cell proliferation (e.g., proliferation of a cell), in vitro or in vivo, comprising contacting a cell with an effective amount of a 3TM compound, as described herein.

In one embodiment, the method is performed in vitro.

In one embodiment, the method is performed in vivo.

In one embodiment, the 3TM compound is provided in the form of a pharmaceutically acceptable composition.

Any type of cell may be treated, including but not limited to, cancer cells derived from tumours or the lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays which may conveniently be used to assess the activity offered by a particular compound are described herein.

For example, a sample of cells (e.g., from a tumour) may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to a 3TM compound, as described herein, for use in a method of treatment of the human or animal body by therapy.

Use in the Manufacture of Medicaments

Another aspect of the present invention pertains to use of a 3TM compound, as described herein, in the manufacture of a medicament for use in treatment.

In one embodiment, the medicament comprises the 3TM compound.

Methods of Treatment

Another aspect of the present invention pertains to a method of treatment comprising administering to a patient in need of treatment a therapeutically effective amount of a 3TM compound, as described herein, preferably in the form of a pharmaceutical composition.

Uses of Certain Known Compounds

Additionally, many of those compounds identified herein with PX code numbers (which may already be known compounds) (collectively referred to herein as "PX Compounds") are also useful in the same was as the 3TM compounds described herein, for example, in the treatment of proliferative disorders, such as, for example, cancer, etc. The various uses of 3TM compounds, as described herein, are also applicable to the PX compounds and salts, hydrates, and solvates thereof.

For example:

Another aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of a PX compound, or a salt, hydrate, or solvate thereof, as described herein.

Another aspect of the present invention pertains to a PX compound, or a salt, hydrate, or solvate thereof, as described herein, for use in a method of treatment of the human or animal body by therapy.

Another aspect of the present invention pertains to use of a PX compound, or a salt, hydrate, or solvate thereof, as described herein, in the manufacture of a medicament for use in treatment. In one embodiment, the medicament comprises the PX compound.

Another aspect of the present invention pertains to a method of treatment comprising administering to a patient in need of treatment a therapeutically effective amount of a PX compound, or a salt, hydrate, or solvate thereof, as described herein, preferably in the form of a pharmaceutical composition.

In one preferred embodiment, the PX compound is a compound selected from PX-001, PX-002, PX-004, PX-016, PX-020, PX-021, and PX-030, and salts, hydrates, and solvates thereof.

| Code No. | Structure | Registry No. |
|---|---|---|
| PX-001 | 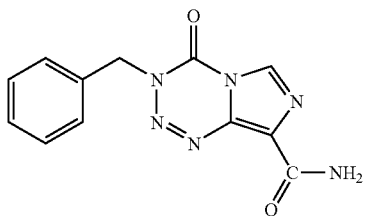 [SMILES: NC(=O)c1ncn2c(=O)n(Cc3ccccc3)nnc12] | 85623-02-5 |
| PX-002 | 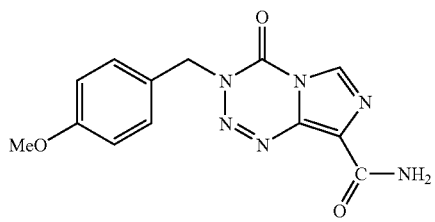 [SMILES: COc1ccc(Cn2nnc3c(C(N)=O)ncn3c2=O)cc1] | 85623-05-8 |

| Code No. | Structure | Registry No. |
|---|---|---|
| PX-004 | 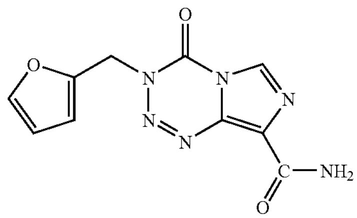 | 208107-16-8 |
| PX-016 | 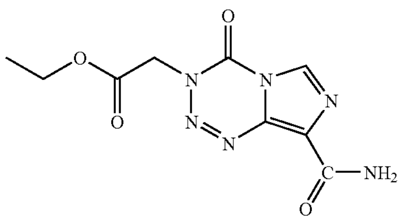 [SMILES: CCOC(=O)Cn1nnc2c(C(N)=O)ncn2c1=O] | 157466-97-2 |
| PX-020 | 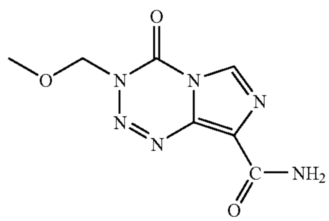 [SMILES: COCn1nnc2c(C(N)=O)ncn2c1=O] | 331456-37-2 |
| PX-021 | 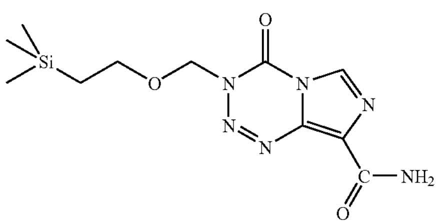 [SMILES: C[Si](C)(C)CCOCn1nnc2c(C(N)=O)ncn2c1=O] | 172988-51-1 |
| PX-030 | 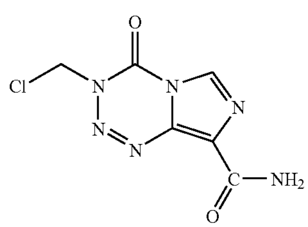 [SMILES: NC(=O)c1ncn2c(=O)n(CCl)nnc12] | 331456-36-1 |

In one preferred embodiment, the PX compound is a compound selected from PX-004, PX-016, PX-020, PX-021, and PX-030, and salts, hydrates, and solvates thereof.

| Code No. | Structure | Registry No. |
|---|---|---|
| PX-004 | 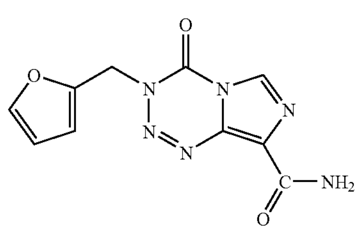 [SMILES: NC(=O)c1ncn2c(=O)n(Cc3ccco3)nnc12] | 208107-16-8 |

-continued

| Code No. | Structure | Registry No. |
|---|---|---|
| PX-016 | 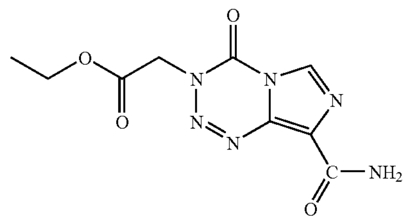 [SMILES: CCOC(=O)Cn1nnc2c(C(N)=O)ncn2c1=O] | 157466-97-2 |
| PX-020 | 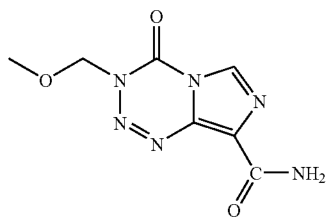 [SMILES: COCn1nnc2c(C(N)=O)ncn2c1=O] | 331456-37-2 |
| PX-021 | 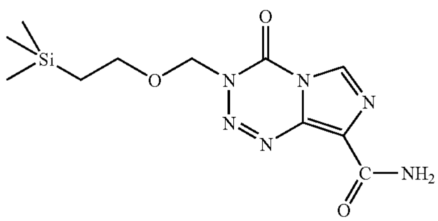 [SMILES: C[Si](C)(C)CCOCn1nnc2c(C(N)=O)ncn2c1=O] | 172988-51-1 |
| PX-030 | 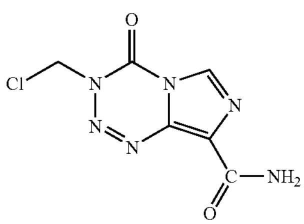 [SMILES: NC(=O)c1ncn2c(=O)n(CCl)nnc12] | 331456-36-1 |

Conditions Treated—Proliferative Disorders and Cancer

In one embodiment (e.g., of use in methods of therapy, of use in the manufacture of medicaments, of methods of treatment), the treatment is treatment of a proliferative disorder.

The term "proliferative condition," as used herein, pertains to an unwanted or uncontrolled cellular proliferation of excessive or abnormal cells which is undesired, such as, neoplastic or hyperplastic growth.

In one embodiment, the treatment is treatment of: a proliferative condition characterised by benign, pre-malignant, or malignant cellular proliferation, including but not limited to, neoplasms, hyperplasias, and tumours (e.g., histocytoma, glioma, astrocyoma, osteoma), cancers (see below), psoriasis, bone diseases, fibroproliferative disorders (e.g., of connective tissues), pulmonary fibrosis, atherosclerosis, smooth muscle cell proliferation in the blood vessels, such as stenosis or restenosis following angioplasty.

In one embodiment, the treatment is treatment of: cancer.

In one embodiment, the treatment is treatment of: lung cancer, small cell lung cancer, non-small cell lung cancer, gastrointestinal cancer, stomach cancer, bowel cancer, colon cancer, rectal cancer, colorectal cancer, thyroid cancer, breast cancer, ovarian cancer, endometrial cancer, prostate cancer, testicular cancer, liver cancer, kidney cancer, renal cell carcinoma, bladder cancer, pancreatic cancer, brain cancer, glioma, sarcoma, osteosarcoma, bone cancer, nasopharyngeal cancer, squamous carcinoma of the head or neck, skin cancer, squamous cancer, Kaposi's sarcoma, melanoma, malignant melanoma, lymphoma, or leukemia.

In one embodiment, the treatment is treatment of:
a carcinoma, for example a carcinoma of the bladder, breast, colon (e.g., colorectal carcinomas such as colon adenocarcinoma and colon adenoma), kidney, epidermal, liver, lung (e.g., adenocarcinoma, small cell lung cancer and non-small cell lung carcinomas), oesophagus, gall bladder, ovary, pancreas (e.g., exocrine pancreatic carcinoma), stomach, cervix, thyroid, prostate, skin (e.g., squamous cell carcinoma);

a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma;

a hematopoietic tumor of myeloid lineage, for example acute and chronic myelogenous leukemias, myelodysplastic syndrome, or promyelocytic leukemia;

a tumour of mesenchymal origin, for example fibrosarcoma or habdomyosarcoma;

a tumor of the central or peripheral nervous system, for example astrocytoma, neuroblastoma, glioma or schwannoma;

melanoma; seminoma; teratocarcinoma; osteosarcoma; xenoderoma pigmentoum; keratoctanthoma; thyroid follicular cancer; or Kaposi's sarcoma.

In one embodiment, the treatment is treatment of solid tumour cancer.

In one embodiment, the treatment is treatment of haematological cancer.

In one embodiment, the treatment is treatment of: lung cancer, breast cancer, ovarian cancer, colorectal cancer, melanoma, renal cancer, prostate cancer, esophageal cancer, squamous carcinoma of the head or neck, or glioma.

In one embodiment, the cancer is characterised by, or further characterised by, cancer stem cells.

In one embodiment, the cancer is MGMT− cancer.

In one embodiment, the cancer is MGMT+ cancer.

In one embodiment, the cancer is MMR proficient cancer.

In one embodiment, the cancer is MMR deficient cancer.

In one embodiment, the cancer is temozolomide resistant or temozolomide refractory.

In one embodiment, the cancer is inherently temozolomide resistant or inherently temozolomide refractory.

In one embodiment, the cancer is temozolomide resistant or temozolomide refractory following exposure to (e.g., treatment with) temozolomide.

The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death). The compounds of the present invention may be used in the treatment of the cancers described herein, independent of the mechanisms discussed herein.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviatiation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents, for example, cytotoxic agents, anticancer agents, molecularly-targeted agents, etc. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

For example, it may be beneficial to combine treatment with a 3TM compound as described herein with one or more other (e.g., 1, 2, 3, 4) agents or therapies that regulates cell growth or survival or differentiation via a different mechanism, thus treating several characteristic features of cancer development.

One aspect of the present invention pertains to a 3TM compound as described herein, in combination with one or more additional therapeutic agents, as described below.

The particular combination would be at the discretion of the physician who would select dosages using his common general knowledge and dosing regimens known to a skilled practitioner.

The agents (i.e., the 3TM compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the 3TM compound described here, plus one or more other agents) may be formulated together in a single dosage form, or alternatively, the individual agents may be formulated separately and presented together in the form of a kit, optionally with instructions for their use.

Other Uses

The 3TM compounds described herein may also be used as cell culture additives to inhibit cell proliferation, etc.

The 3TM compounds described herein may also be used as part of an in vitro assay, for example, in order to determine whether a candidate host is likely to benefit from treatment with the compound in question.

The 3TM compounds described herein may also be used as a standard, for example, in an assay, in order to identify other compounds, other anti-proliferative agents, other anti-cancer agents, etc.

Kits

One aspect of the invention pertains to a kit comprising (a) a 3TM compound as described herein, or a composition comprising a 3TM compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The 3TM compound or pharmaceutical composition comprising the 3TM compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the 3TM compound to be administered alone, it is preferable to present it as a pharmaceutical formulation (e.g., composition, preparation, medicament) comprising at least one 3TM compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one 3TM compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the 3™ compounds, and compositions comprising the 3TM compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular 3TM compound, the route of administration, the time of administration, the rate of excretion of the 3TM compound, the duration of the treatment, other drugs, compounds, and/or materials used in combination, the severity of the condition, and the species, sex, age, weight, condition, general health, and prior medical history of the patient. The amount of 3TM compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the 3TM compound is in the range of about 10 µg to about 250 mg (more typically about 100 µg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

Synthesis 1

3-Cyclohexylmethyl-8-carbamoylimidazotetrazin-4-one (GG-001)

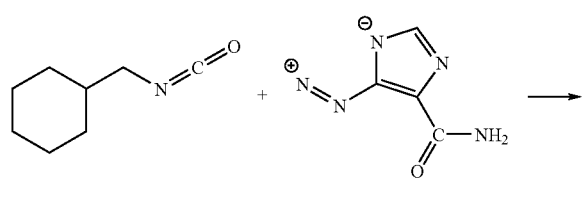

Cyclohexylmethyl isocyanate (0.6 mL, 4.2 mmol) was added drop wise to a suspension of 5-diazoimidazole-4-carboxamide (0.5 g, 3.65 mmol) in dry dimethylsulfoxide (5 mL) at room temperature under nitrogen. After 24 hours, the reaction mixture was poured onto ice. The resulting mixture was extracted with dichloromethane (3×25 mL) and the combined organic extracts were washed with water (25 mL) and brine (25 mL), dried over sodium sulfate, and evaporated to dryness. The resulting solid was triturated with ethyl acetate and filtered. The residue was then suspended in ether, filtered, and air dried to afford the target compound as a beige solid. Yield: 150 mg, 0.54 mmol 15%. LCMS (ES+) m/z 277 (M+H)+ at 2.67 minutes. $^1$H NMR (400 MHz, $d_6$-DMSO) δ: 8.78 (1H, s), 7.78 (1H, br s), 7.66 (1H, bs), 4.13 (2H, d), 1.87 (1H, m), 1.55-1.75 (5H, overlapping m), 1.10-1.25 (3H, overlapping m), 1.04 (2H, m).

Synthesis 2

3-Isopropyl-8-carbamoylimidazotetrazin-4-one (PP-001)

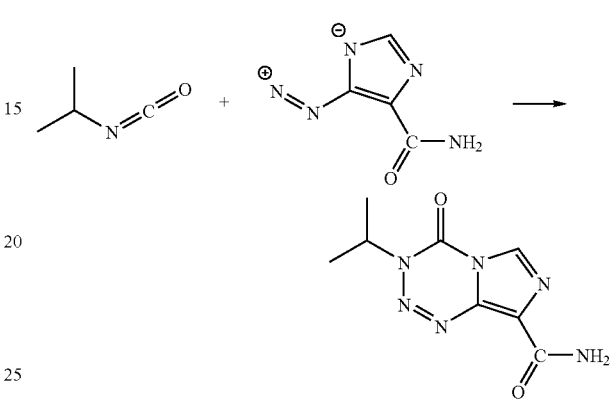

Isopropyl isocyanate (0.41 mL, 4.2 mmol) was added drop wise to a suspension of 5-diazoimidazole-4-carboxamide (0.5 g, 3.65 mmol) in dry dimethylsulfoxide (5 mL) at room temperature under nitrogen. After 24 hours, the reaction mixture was poured onto ice. The resulting mixture was extracted with dichloromethane (3×25 mL) and the combined organic extracts were washed with water (25 mL) and brine (25 mL), dried over sodium sulfate, and evaporated to dryness. The resulting solid was triturated with ethyl acetate and filtered. The residue was then washed with diethyl ether and ethyl acetate, filtered, and dried in vacuo to afford the target compound as a beige solid. Yield: 235 mg, 1.06 mmol 29%. LCMS (ES+) m/z 223 (M+H)+ at 1.57 minutes. $^1$H NMR (400 MHz, $d_6$-DMSO) δ: 8.77 (1H, s), 7.77 (1H, bs), 7.63 (1H, br s), 5.03 (1H, m), 1.49 (6H, d).

Synthesis 3

3-Cyclopentyl-8-carbamoylimidazotetrazin-4-one (FF-001)

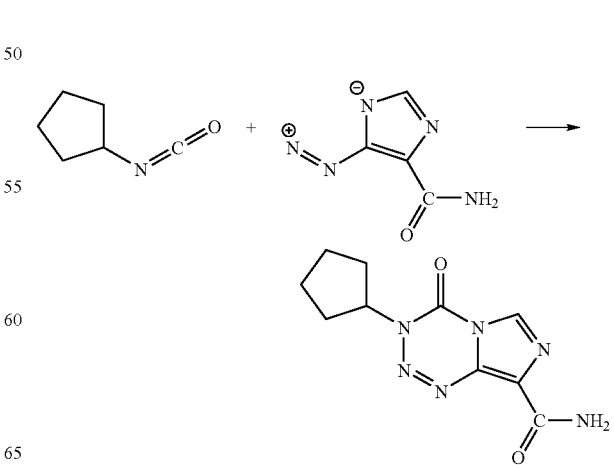

Cyclopentyl isocyanate (0.47 mL, 4.2 mmol) was added drop wise to a suspension of 5-diazoimidazole-4-carboxamide (0.5 g, 3.65 mmol) in dry dimethylsulfoxide (5 mL) at room temperature under nitrogen. After 24 hours, the reaction mixture was poured onto ice. The resulting mixture was extracted with dichloromethane (3×25 mL) and the combined organic extracts were washed with water (25 mL) and brine (25 mL), dried over sodium sulfate, and evaporated to dryness. The resulting solid was triturated with ethyl acetate and filtered. The residue was then washed with diethyl ether and ethyl acetate, filtered, and dried in vacuo to afford the target compound as a beige solid. Yield: 286 mg, 1.16 mmol 31%. LCMS (ES+) m/z 249 (M+H)+ at 2.09 minutes. $^1$H NMR (400 MHz, $d_6$-DMSO) δ: 8.75 (1H, s), 7.72 (1H, bs), 7.60 (1H, br s), 5.18 (1H, m), 1.95-2.15 (4H, overlapping m), 1.85 (2H, m), 1.65 (2H, m).

Synthesis 4

3-Piperidin-4-yl-8-carbamoylimidazotetrazin-4-one hydrobromide (HH-001)

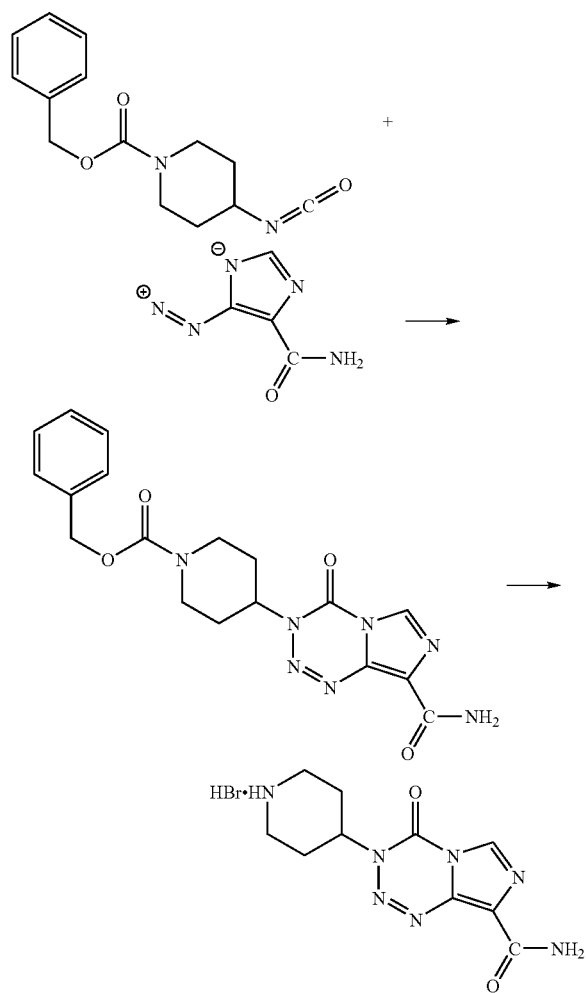

A suspension of 5-diazoimidazole-4-carboxamide (0.5 g, 3.65 mmol) in dry dimethylsulfoxide (5 mL) was added to a suspension of benzyl 4-isocyanatotetrahydro-1(2H)-pyridinecarboxylate (Sigma Aldrich) (1 g, 3.84 mmol) at room temperature under nitrogen. After 24 hours, the reaction mixture was poured onto ice and the resulting precipitate was washed with ethyl acetate (10 mL) and ether (10 mL) to afford the benzyloxycarbonyl protected imidazotetrazinone (3-(1-benzyloxycarbonylpiperidin-4-yl)-8-carbamoylimidazotetrazin-4-one) as a light brown solid which was used without further purification. Yield: 797 mg, 80% pure, 1.55 mmol, 42%. LCMS (ES+) m/z 249 (M+H)+ at 2.09 minutes. $^1$H NMR (400 MHz, $d_6$-DMSO) δ: 8.75 (1H, s), 7.72 (1H, bs), 7.60 (1H, br s), 5.18 (1H, m), 1.95-2.15 (4H, overlapping m), 1.85 (2H, m), 1.65 (2H, m).

HBr in acetic acid (1.906 mL, 16.05 mmol) was added to a solution of 3-(1-benzyloxycarbonylpiperidin-4-yl)-8-carbamoylimidazotetrazin-4-one (0.638 g, 80% pure, 1.28 mmol) in acetic acid (6.4 mL) and the mixture was heated to 50° C. After 5 hours, the mixture was allowed to cool to room temperature then diluted with ether. The resulting precipitate was removed by filtration and washed with ether (20 mL) to afford a grey solid which was dissolved in the minimum amount of hot water (approximately 20 mL) and allowed to cool. Tetrahydrofuran (approximately 20 mL) was added drop wise until a precipitate formed. Filtration afforded the title compound as a pale grey solid. Yield: 0.217 g, 0.816 mmol, 49% yield. LCMS (ES+), m/z 264 (M+H)+ at 1.05 minutes. $^1$H NMR (400 MHz, $d_6$-DMSO) δ: 8.81 (1H, s), 8.53 (2H, br s), 7.78 (1H, br s), 7.64 (1H, br s), 5.04 (1H, m), 3.43 (2H, br d), 3.16 (2H, dt), 2.28 (2h, qd) 2.13 (2h, br d).

Synthesis 5

3-Cyclopropyl-8-carbamoylimidazotetrazin-4-one (FF-002)

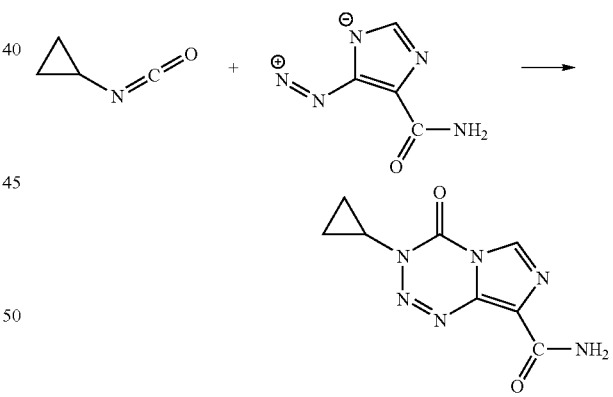

Cyclopropyl isocyanate was made according to the procedure described in WO 96/27588. Cyclopropyl isocyanate (3 mL) was added drop wise to a suspension of 5-diazoimidazole-4-carboxamide (0.5 g, 3.65 mmol) in dry dimethylsulfoxide (5 mL) at room temperature under nitrogen and the mixture was stirred in the dark at room temperature. After 72 hours, the reaction mixture was poured onto ice (approximately 25 mL). The resulting precipitate was collected and washed with ethyl acetate (10 mL) and ether (10 mL) and purified by flash column chromatography (SiO$_2$, 1:1 acetonitrile/dichloromethane) to afford the title compound as a white solid. Yield: 55 mg, 0.247 mmol, 7%. LCMS (ES+), m/z 221

(M+H)⁺ at 1.24 minutes. ¹H NMR (400 MHz, d₆-DMSO) δ: 8.78 (1H, s), 7.76 (1H, br s), 7.64 (1H, br s), 3.59 (1H, quintet), 1.12 (4h, d).

Synthesis 6

3-(Methylthio)methyl-8-carbamoylimidazotetrazin-4-one (KK-001)

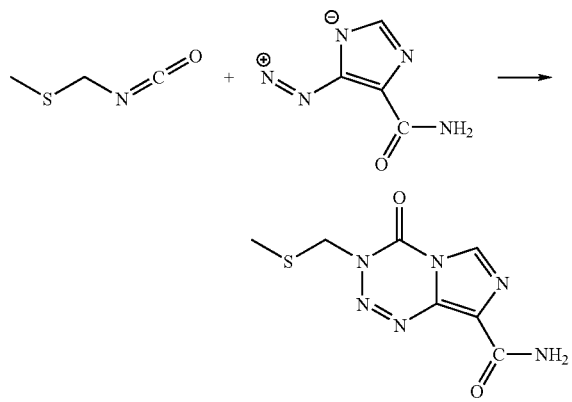

(Methylthio)methylisocyanate was made according to the procedure described in WO 96/27588 and used crude. Crude (methylthio)methylisocyanate was added drop wise to a suspension of 5-diazoimidazole-4-carboxamide (0.45 g, 3.28 mmol) in dry dimethylsulfoxide (5 mL). The reaction was stirred in the dark at room temperature. After 16 hours, the reaction mixture was poured onto ice (approximately 25 mL) and the resulting precipitate was washed with ethyl acetate (10 mL) and ether (10 mL) then purified by flash column chromatography (SiO₂, 1:1 acetonitrile/dichloromethane) and preparative HPLC to afford the title compound as a pale pink solid. Yield: 14.6 mg, 0.061 mmol, 1.9% yield. LCMS (ES+), m/z 241 (M+H)⁺ at 1.43 minutes. ¹H NMR (400 MHz, d₆-DMSO) δ: 8.84 (1H, s), 7.79 (1H, br s), 7.68 (1H, br s), 5.41 (2H, s), 2.23 (3h, s).

Synthesis 7

Ethyl 3-(8-carbamoyl-oxoimidazo[5,1-d][1,2,3,5]tetrazin-3(4H)-yl)propanoate (LL-002)

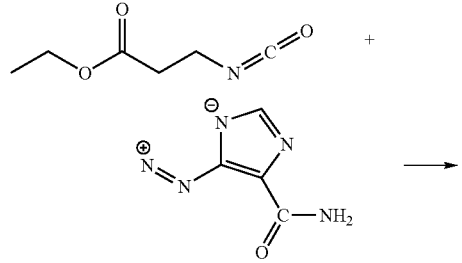

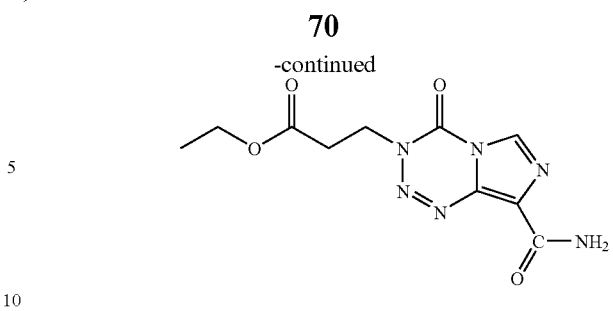

Ethyl 3-isocyanatopropionate (Alfa Lancaster) (0.504 mL, 3.83 mmol) was added drop wise to a suspension of 5-diazoimidazole-4-carboxamide (0.450 g, 3.65 mmol) in dry dimethylsulfoxide (4.5 mL) at room temperature under nitrogen. The reaction was stirred in the dark at room temperature. After 16 hours, the reaction mixture was poured onto ice (approximately 25 mL) and the resulting precipitate was washed with ethyl acetate (10 mL) and ether (10 mL) to afford the title compound as a pale brown solid. Yield: 770 mg, 2.75 mmol, 75%. LCMS (ES+), m/z 281 (M+H)⁺ at 1.60 minutes. ¹H NMR (400 MHz, d₆-DMSO) δ: 8.86 (1H, s), 7.75 (1H, br s), 7.62 (1H, br s), 4.51 (2H, t), 4.07 (2H, q), 2.89 (2H, t), 1.17 (3H, t).

Synthesis 8

3-(8-Carbamoyl-oxoimidazo[5,1-d][1,2,3,5]tetrazin-3(4H)-yl)propanoic acid (LL-001)

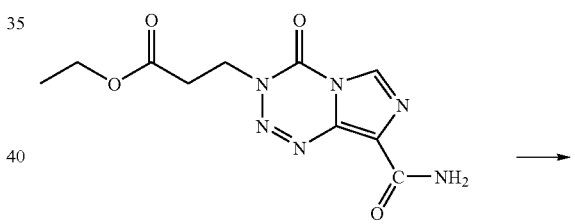

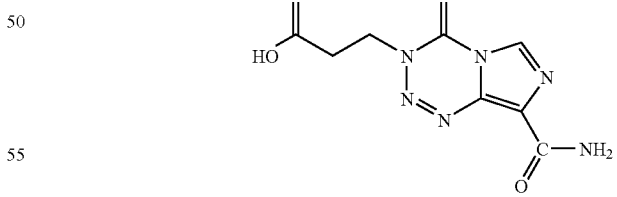

A suspension of ethyl 3-(8-carbamoyl-oxoimidazo[5,1-d][1,2,3,5]tetrazin-3(4H)-yl)propanoate (0.5 g, 1.784 mmol) in 5 M hydrochloric acid (2.34 mL, 11.70 mmol) was heated at 45° C. After 16 hours, the reaction mixture was filtered and the residue was washed with water (5 mL) and acetone (5 mL). A portion (50 mg from a total of 332 mg) was recrystallized from hot acetonitrile/water to afford the title compound as an off white solid. Yield: 32 mg, 0.13 mmol, 47% pro rata. LCMS (ES+), m/z 281 (M+H)⁺ at the solvent front.

$^1$H NMR (400 MHz, d$_6$-DMSO) δ: 12.5 (1H, br s), 8.80 (1H, s), 7.75 (1H, br s), 7.65 (1H, br s), 4.45 (2H, t), 2.75 (2H, t).

Synthesis 9

3-(8-Carbamoyl-oxoimidazo[5,1-d][1,2,3,5]tetrazin-3(4H)-yl)propanamide (JJ-004)

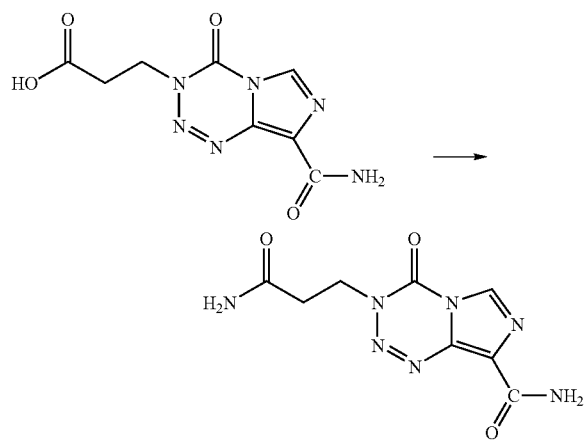

Isobutyl chloroformate (1 M in toluene, 0.218 mL, 0.218 mmol) then N-methyl morpholine (0.024 mL, 0.218 mmol) were added to a stirred mixture of 3-(8-carbamoyl-oxoimidazo[5,1-d][1,2,3,5]tetrazin-3(4H)-yl)propanoic acid (0.05 g, 0.198 mmol) in dimethylformamide (1.25 mL) under nitrogen at −10° C. to −15° C. The reaction mixture was stirred for one hour at this temperature then ammonia (0.5 M solution in 1,4-dioxane, 792 µL, 0.396 mmol) and triethylamine (27.5 µL, 0.198 mmol) in dimethylformamide (0.1 mL) were added. The reaction mixture was stirred at −10° C. to −15° C. for one further hour then allowed to warm to room temperature. After 16 hours, ether (2 mL) was added and the resulting precipitate was washed with ether (10 mL), acetonitrile (10 mL) and water to afford the title compound as a white solid. Yield 12 mg, 0.048 mmol, 24%. LCMS (ES+), m/z 252 (M+H)$^+$ at the solvent front. $^1$H NMR (400 MHz, d$_6$-DMSO) δ: 8.82 (1H, s), 7.77 (1H, br s), 7.65 (1H, br s), 7.45 (1H, br s), 6.92 (1H, br s) 4.45 (2H, t), 2.64 (2H, t).

Synthesis 10

2-(8-Carbamoyl-oxoimidazo[5,1-d][1,2,3,5]tetrazin-3(4H)-yl)ethanoic acid

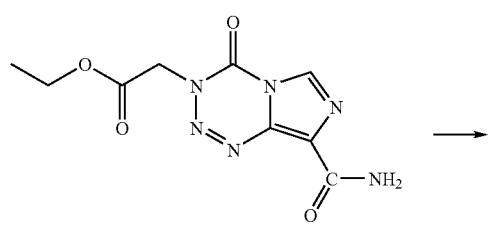

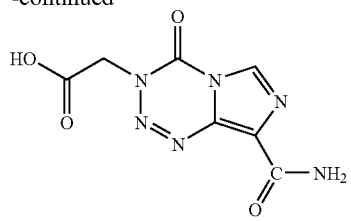

The title compound was prepared using a method similar to that described in Wang, Y., et al., 1995, *J. Chem. Soc. Perkin Trans.* 1, Vol. 21, pp. 2783-2787.

Ethyl 8-Carbamoyl-3,4-dihydro-4-oxoimidazo[5,1-d]-1,2,3,5-tetrazin-3-ylacetate (10.2 g) was suspended in hydrochloric acid (5 M, 50 mL). The suspension was stirred for 4 hours at 40-45° C. until hydrolysis was complete (TLC). The mixture was concentrated under reduced pressure to 20 mL and the solid product was collected and washed with acetone (3×20 mL). The product was dried under high vacuum to give the title compound. LCMS (ES$^-$), m/z 237 (M$^-$H$^-$) in the solvent front. Yield 25.04%.

Synthesis 11

2-(8-Carbamoyl-oxoimidazo[5,1-d][1,2,3,5]tetrazin-3(4H)-yl)ethanamide (JJ-001)

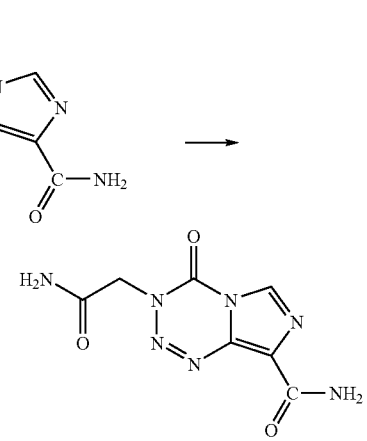

Isopropyl chloroformate (1M in toluene, 1.076 mL, 1.076 mmol) and then N-methyl morpholine (0.118 mL, 1.076 mmol) were added to a stirred mixture of 2-(8-carbamoyl-oxoimidazo[5,1-d][1,2,3,5]tetrazin-3(4H)-yl)ethanoic acid (0.233 g, 0.978 mmol) in dimethylformamide (4.7 mL) under nitrogen at −10° C. to −15° C. The reaction mixture was stirred for one hour at this temperature then ammonia (0.5 M solution in 1,4-dioxane, 3.91 mL, 1.956 mmol) and triethylamine (0.136 mL, 0.978 mmol) in dimethylformamide (0.1 mL) were added. The reaction mixture was allowed to stir at −10° C. to −15° C. for one further hour then allowed to warm to room temperature. After 64 hours, ether (10 mL) was added and the precipitate was washed with ether (10 mL), acetonitrile (10 mL) and water (4×10 mL) to afford the title compound. Yield 105 mg, 0.443 mmol, 45%. LCMS (ES+), m/z 238 (M+H)$^+$ at the solvent front. $^1$H NMR (400 MHz, $d_6$-DMSO) δ: 8.88 (1H, s), 7.84 (1H, br s), 7.72 (1H, br s), 7.70 (1H, br s), 7.44 (1H, br s) 4.88 (2H, s).

Synthesis 12

3-(Cyclopentyl)methyl-8-carbamoylimidazotetrazin-4-one (GG-002)

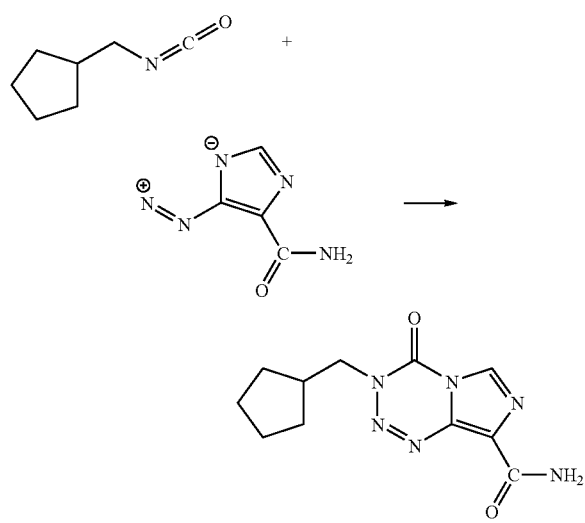

Cyclopentylmethyl isocyanate was made according to the procedure described in WO 96/27588 and used crude. Crude cyclopentylmethyl isocyanate distillate residue (approximately 9 mL) was added drop wise to a suspension of 5-diazoimidazole-4-carboxamide (0.5 g, 3.65 mmol) in dry dimethylsulfoxide (5 mL). The reaction mixture was stirred at the dark at room temperature under nitrogen. After 16 hours, the mixture was poured onto ice (approximately 25 mL) and the resulting precipitate was washed with ethyl acetate (10 mL) and ether (10 mL), then purified by flash column chromatography ($SiO_2$, 1:1 acetonitrile/dichloromethane) and recrystallized from acetonitrile to afford the title compound as an off white solid. Yield 30 mg, 0.11 mmol, 3%. LCMS (ES+), m/z 263 (M+H)$^+$ at 2.75 minutes. $^1$H NMR (400 MHz, $d_6$-DMSO) δ: 8.80 (1H, s), 7.78 (1H, br s), 7.66 (1H, br s), 4.23 (2H, d), 2.41 (1H, m), 1.75 (2H, m), 1.65 (2H, m), 1.53 (2H, m), 1.34 (2H, m).

Synthesis 13

(R)-3-(-1-Phenylethyl)-8-carbamoylimidazotetrazin-4-one (BB-001)

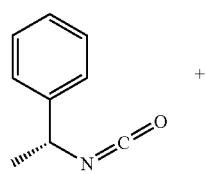
+
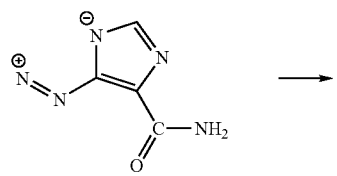

→

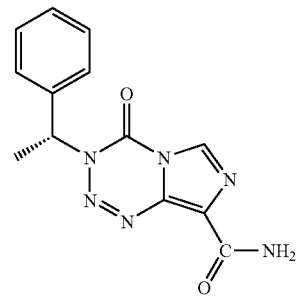

(R)-(+)-1-Phenylethyl isocyanate (Sigma Aldrich) (0.6 mL, 4.2 mmol) was added drop wise to a suspension of 5-diazoimidazole-4-carboxamide (0.5 g, 3.65 mmol) in dry dimethylsulfoxide (5 mL) at room temperature under nitrogen. The reaction mixture was stirred at the dark at room temperature under nitrogen. After 16 hours, the reaction mixture was poured onto ice and extracted with dichloromethane (3×25 mL). The combined organics were washed with water (25 mL) and brine (25 mL), dried over sodium sulfate, and evaporated to dryness. The resulting solid was triturated with ethyl acetate then purified by flash column chromatography ($SiO_2$, 3:7 acetonitrile/dichloromethane) to furnish the desired product as a white solid. Yield: 577 mg, 2.03 mmol, 56%. LCMS (ES$^+$) m/z 285 (M+H)$^+$ at 2.67 minutes. $^1$H NMR (400 MHz, $d_6$-DMSO) δ: 8.79 (1H, s), 7.78 (1H, br s), 7.66 (1H, bs), 7.46 (2H, m), 7.29-7.39 (3H, overlapping m), 6.11 (1H, q), 1.89, (3H, d).

Synthesis 14

(S)-3-(−1-Phenylethyl)-8-carbamoylimidazotetrazin-4-one (BB-002)

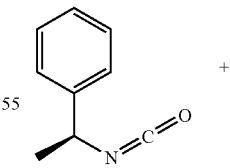
+
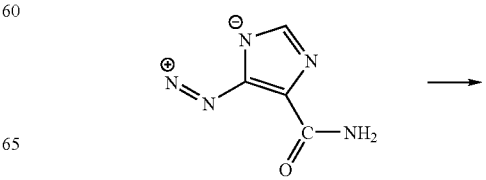

→

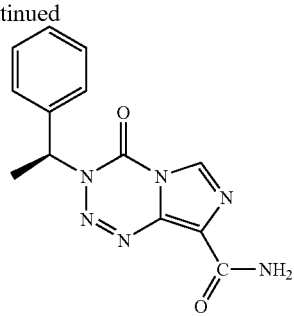

(S)-(–)-1-Phenylethyl isocyanate (Sigma Aldrich) (0.6 mL, 4.2 mmol) was added drop wise to a suspension of 5-diazoimidazole-4-carboxamide (0.5 g, 3.65 mmol) in dry dimethylsulfoxide (5 mL) at room temperature under nitrogen. The reaction mixture was stirred at the dark at room temperature under nitrogen. After 16 hours, the reaction mixture was poured onto ice and the resulting precipitate was purified by flash column chromatography ($SiO_2$, 3:7 acetonitrile/dichloromethane) to furnish the desired product as a white solid. Yield: 678 mg, 2.39 mmol, 65%. LCMS ($ES^+$) m/z 285 $(M+H)^+$ at 2.73 minutes. $^1H$ NMR (400 MHz, $d_6$-DMSO) δ: 8.79 (1H, s), 7.78 (1H, br s), 7.66 (1H, bs), 7.46 (2H, m), 7.29-7.39 (3H, overlapping m), 6.11 (1H, q), 1.89, (3H, d).

Synthesis 15

N-(8-Carbamoyl-oxoimidazo[5,1-d][1,2,3,5]tetrazin-3(4H)-yl)ethanoyl morpholine (JJ-005)

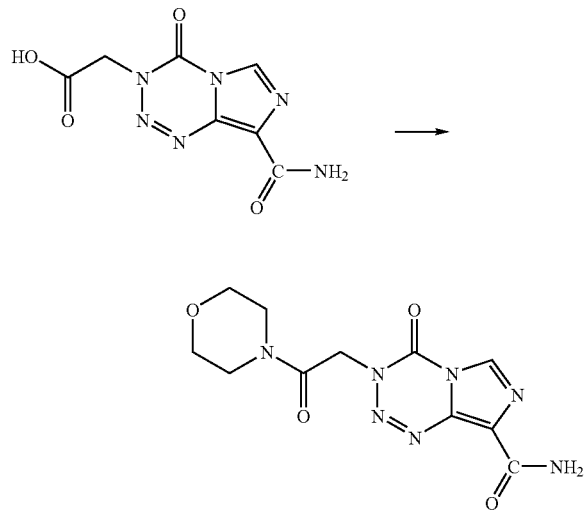 [SMILES: NC(=O)c1ncn2c(=O)n(CC(=O)O)nnc12 ; NC(=O)c1ncn2c(=O)n(CC(=O)N3CCOCC3)nnc12]

Isopropyl chloroformate (1 M in toluene, 1.155 mL, 1.155 mmol) and then N-methyl morpholine (0.127 mL, 1.155 mmol) were added to a stirred solution of 2-(8-carbamoyl-oxoimidazo[5,1-d][1,2,3,5]tetrazin-3(4H)-yl)ethanoic acid (0.25 g, 1.050 mmol) in dimethylformamide (1.34 mL) under nitrogen at –10° C. to –15° C. The reaction was stirred for one hour at this temperature then morpholine (0.183 g, 2.100 mmol) and triethylamine (0.146 mL, 1.050 mmol) in dimethylformamide (0.1 mL) were added. The reaction mixture was stirred at –10° C. to –15° C. for one hour then allowed to warm to room temperature. After 16 hours, ether (5 mL) was added and the resulting precipitate was washed with ether (2×5 mL), acetonitrile (2×5 mL), dichloromethane (2×5 mL) and ether (2×5 mL) then purified by flash column chromatography ($SiO_2$, 9:1 acetonitrile/dichloromethane) and triturated with ether to furnish the desired product as a white solid. Yield: 105 mg, 0.34 mmol, 33%. LCMS ($ES^+$) m/z 308 $(M+H)^+$ at 0.97 minutes. $^1H$ NMR (400 MHz, $d_6$-DMSO) δ: 8.87 (1H, s), 7.83 (1H, br s), 7.68 (1H, bs), 5.35 (2H, s), 3.66 (2H, m), 3.51-3.60 (4H, overlapping multiplets), 3.45 (2H, m).

Synthesis 16

N-Methyl (8-Carbamoyl-oxoimidazo[5,1-d][1,2,3,5]tetrazin-3(4H)-yl)ethanamide (JJ-002)

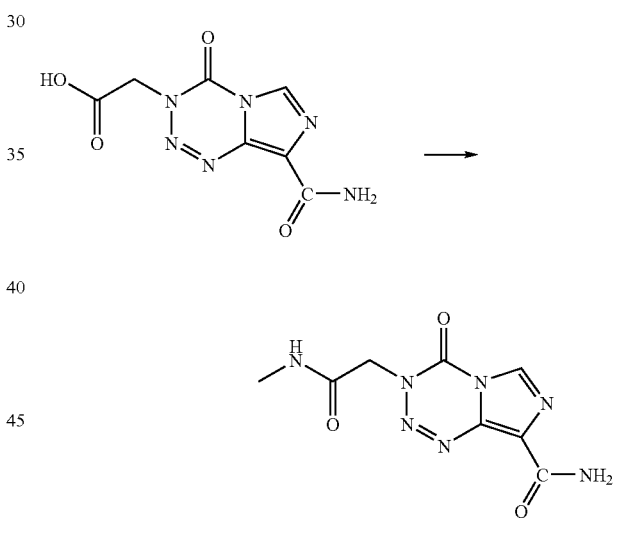

Isopropyl chloroformate (1 M in toluene, 1.155 mL, 1.155 mmol) then N-methyl morpholine (0.127 mL, 1.155 mmol) were added to a stirred solution of 2-(8-carbamoyl-oxoimidazo[5,1-d][1,2,3,5]tetrazin-3(4H)-yl)ethanoic acid (0.25 g, 1.050 mmol) in dimethylformamide (1.34 mL) under nitrogen at –10° C. to –15° C. After 1 hour, methylamine hydrochloride (142 mg, 2.100 mmol) then triethylamine (0.292 mL, 2.100 mmol) in dimethylformamide (0.1 mL) were added. The reaction mixture was stirred at –10° C. to –15° C. for one hour then allowed to warm to room temperature. After 16 hours, ether (5 mL) was added and the resulting precipitate was washed with ether (2×5 mL), acetonitrile (2×5 mL), dichloromethane (2×5 mL) and ether (2×5 mL), then purified by flash column chromatography ($SiO_2$, 9:1 acetonitrile/dichloromethane), recrystallized from acetonitrile and triturated with ether to furnish the desired product as a pale pink solid. Yield: 82 mg, 0.33 mmol, 31%. LCMS ($ES^+$) m/z 252

(M+H)+ at solvent front. ¹H NMR (400 MHz, d₆-DMSO) δ: 8.86 (1H, s), 8.14 (1H, br q), 7.83 (1H, br s), 7.69 (1H, bs), 4.89 (2H, s), 2.60 (3H, d).

Synthesis 17

N,N-Dimethyl (8-Carbamoyl-oxoimidazo[5,1-d][1,2,3,5]tetrazin-3(4H)-yl)ethanamide (JJ-003)

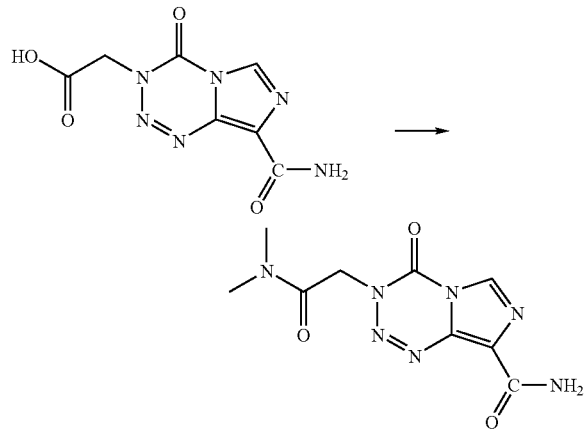

Isopropyl chloroformate (1 M in toluene, 1.155 mL, 1.155 mmol) then N-methyl morpholine (0.127 mL, 1.155 mmol) were added to a stirred solution of 2-(8-carbamoyl-oxoimidazo[5,1-d][1,2,3,5]tetrazin-3(4H)-yl)ethanoic acid (0.25 g, 1.050 mmol) in dimethylformamide (1.34 mL) under nitrogen at −10° C. to −15° C. After 1 hour, dimethylamine hydrochloride (0.171 g, 2.100 mmol) and then triethylamine (0.292 mL, 2.100 mmol) in dimethylformamide (0.1 mL) were added. The reaction mixture was stirred at −10° C. to −15° C. for one hour then allowed to warm to room temperature. After 40 hours, ether (5 mL) was added and the resulting precipitate was washed with ether (2×5 mL), acetonitrile (2×5 mL), dichloromethane (2×5 mL) and ether (2×5 mL) then purified by flash column chromatography (SiO₂, 9:1 acetonitrile/dichloromethane) and preparative HPLC to furnish the title compound. Yield: 23 mg, 0.082 mmol, 8%. LCMS (ES⁺) m/z 266 (M+H)+ at 0.80 minutes. ¹H NMR (400 MHz, d₆-DMSO) δ: 8.89 (1H, s), 7.86 (1H, br s), 7.72 (1H, bs), 5.33 (2H, s), 3.10 (3H, s), 2.86 (3H, s).

Synthesis 18

(R)-3-(−1-(4-Methoxyphenyl)ethyl)-8-carbamoylimidazotetrazin-4-one (BB-003)

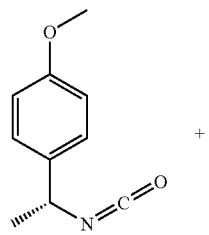

+

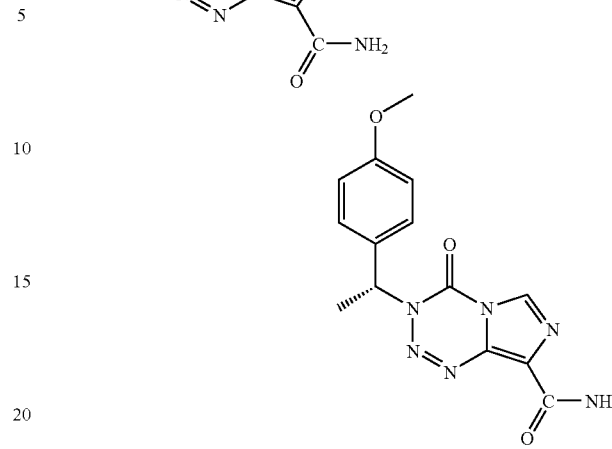

(R)-(+)-1-(4-Methoxyphenyl)ethylisocyanate (0.445 mL, 3.83 mmol) was added drop wise to a suspension of 5-diazoimidazole-4-carboxamide (0.5 g, 3.65 mmol) in dry dimethylsulfoxide (5 mL). The reaction mixture was stirred at the dark at room temperature under nitrogen. After 16 hours, the reaction mixture was poured onto ice and the resulting precipitate was washed with ether and purified by flash column chromatography (SiO₂, gradient 20% acetonitrile in dichloromethane to 100% acetonitrile) to furnish the desired product as a white solid. Yield: 189 mg, 0.58 mmol, 16%. LCMS (ES⁺) m/z 315 (M+H)+ at 2.37 minutes. ¹H NMR (400 MHz, d₆-DMSO) δ: 8.78 (1H, s), 7.76 (1H, br s), 7.64 (1H, bs), 7.39 (2H, m), 6.91 (2H, m), 6.05 (1H, q), 3.72 (3H, s), 1.85, (3H, d).

Synthesis 19

3-Propargyl-8-carbamoylimidazotetrazin-4-one (EE-001)

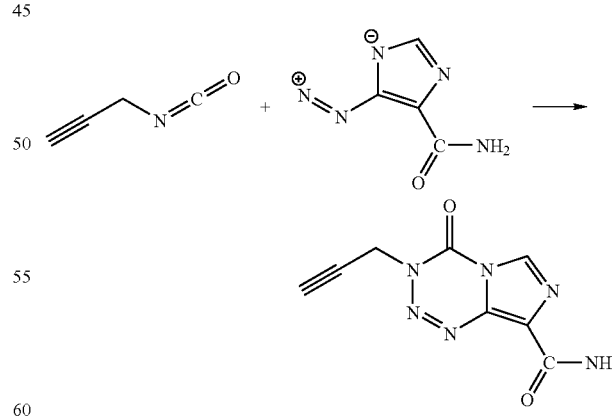

Triphosgene (1.8 g, 6 mmol) was added in one portion to a mixture of propargylamine (1 g, 18.2 mmol) in dichloromethane (75 mL) and saturated sodium hydrogen carbonate solution (75 mL) cooled to 0° C. The mixture was stirred at 0° C. for 1 hour and then poured into a separating funnel. The organic layer was separated and the aqueous layer washed with a further portion of dichloromethane (10 mL). The combined organic fractions were dried over magnesium sulfate and filtered. The dichloromethane was removed by distillation at atmospheric pressure. The pressure was gradually reduced using a high vacuum line until a colourless oil (propargyl isocyanate) distilled over.

The crude distillate (propargyl isocyanate) from the previous step (0.6 g, 7.3 mmol) was added drop wise to a suspension of 5-diazoimidazole-4-carboxamide (0.50 g, 3.6 mmol) in dry dimethylsulfoxide (5 mL). The reaction mixture was stirred in the dark at room temperature under nitrogen. After 16 hours, the reaction mixture was poured onto ice and the mixture was filtered. The aqueous filtrate was concentrated in vacuo and the residue was purified by reverse phase chromatography (C18 silica, gradient 0-100% acetonitrile in water), and flash column chromatography (SiO$_2$, gradient 0-100% acetonitrile in dichloromethane) to furnish the title compound as a white solid. Yield: 24 mg, 0.11 mmol, 3%. LCMS (ES$^+$) m/z 219 (M+H)$^+$ at 1.11 minutes. $^1$H NMR (400 MHz, d$_6$-DMSO) δ: 8.86 (1H, s), 7.82 (1H, br s), 7.70 (1H, bs), 5.14 (2H, d), 3.52 (1H, t).

Synthesis 20

(S)-3-(-1-Phenylpropyl)-8-carbamoylimidazotetrazin-4-one (BB-004)

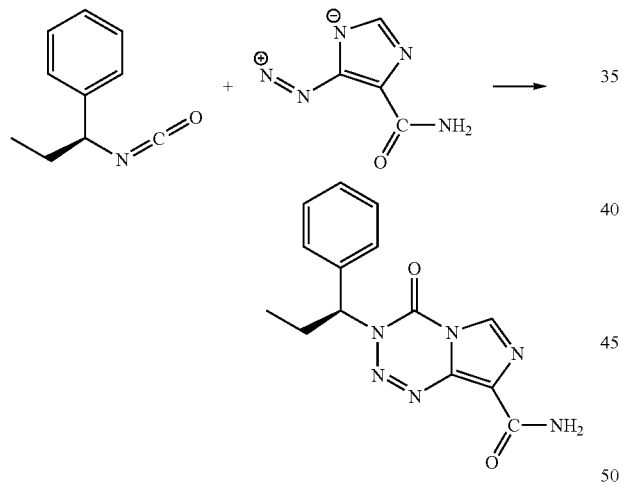

(S)-(−)-1-Phenylpropyl isocyanate (Alfa Lancaster) (0.6 mL, 4.2 mmol) was added drop wise to a suspension of 5-diazoimidazole-4-carboxamide (0.5 g, 3.65 mmol) in dry dimethylsulfoxide (5 mL). The reaction mixture was stirred at the dark at room temperature under nitrogen. After 16 hours, the reaction mixture was poured onto ice and extracted with dichloromethane (3×25 mL). The combined organic extracts were washed with water (25 mL) and brine (25 mL), dried over sodium sulfate, and evaporated to dryness. The residue was purified by reverse phase chromatography (C18 silica, gradient 0-100% acetonitrile in water), and then dried by co-evaporation with toluene to furnish the desired product as a pink solid. Yield: 359 mg, 1.20 mmol, 33%. LCMS (ES$^+$) m/z 299 (M+H)$^+$ at 2.62 minutes. $^1$H NMR (400 MHz, d$_6$-DMSO) δ: 8.78 (1H, s), 7.78 (1H, br s), 7.66 (1H, bs), 7.48 (2H, m), 7.30-7.42 (3H, overlapping m), 5.82 (1H, q), 2.41 (1H, m), 2.32 (1H, m), 0.94, (3H, t).

Synthesis 21

(+/−) 3-(-1-(4-Bromophenyl)ethyl)-8-carbamoylimidazotetrazin-4-one (BB-005)

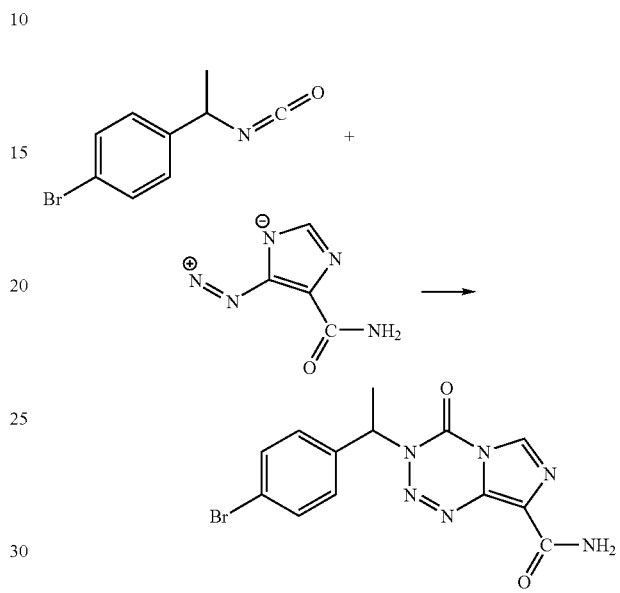

4-Bromo-α-methylbenzyl isocyanate (Alfa Lancaster) (0.32 mL, 2.212 mmol) was added drop wise to a suspension of 5-diazoimidazole-4-carboxamide (264 mg, 1.92 mmol) in dry dimethylsulfoxide (5 mL). The reaction mixture was stirred in the dark at room temperature under nitrogen. After 18 hours, the reaction mixture was poured onto ice and the resulting precipitate was purified by flash column chromatography (SiO$_2$, gradient 0-100% acetonitrile in dichloromethane) to furnish the title compound as a white solid. Yield: 525 mg, 1.45 mmol, 75%. LCMS (ES$^+$) m/z 363/365 (M+H)$^+$ at 2.77 minutes. $^1$H NMR (400 MHz, d$_6$-DMSO) δ: 8.78 (1H, s), 7.78 (1H, br s), 7.64 (1H, bs), 7.55 (2H, m), 7.40 (2H, m), 6.06 (1H, q), 1.84, (3H, d).

Synthesis 22

3-(2-(tert-Butyldimethylsilyloxy)ethyl)-4-oxo-3,4-dihydroimidazo[5,1-d][1,2,3,5]tetrazine-8-carboxamide (N,N-001)

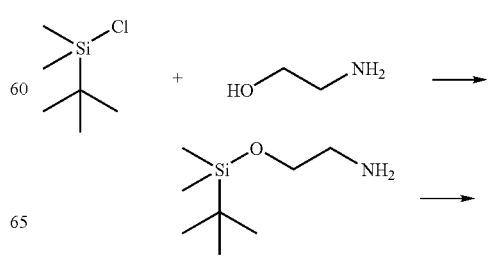

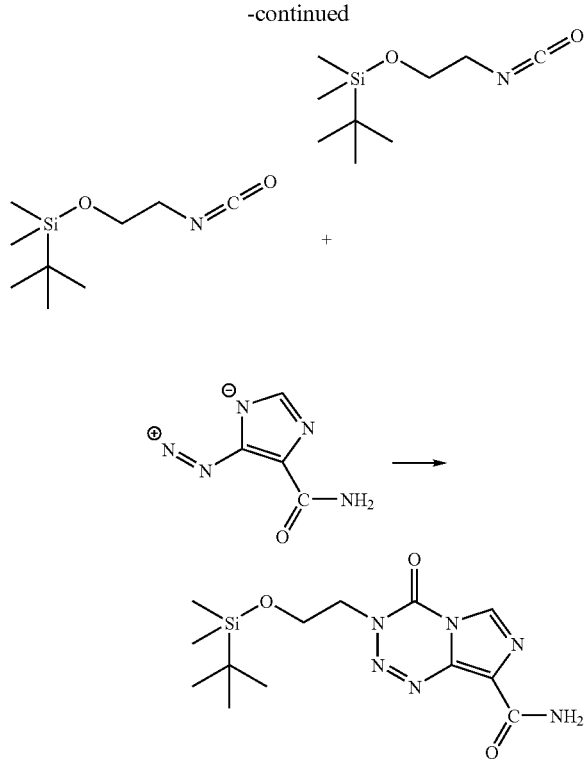

tert-Butyldimethylsilylchloride (24.87 g, 165 mmol) was added portion wise to a solution of ethanolamine (11.84 mL, 150 mmol) in triethylamine (46.0 mL, 330 mmol) and dichloromethane (100 mL) at 0° C. The reaction was stirred at this temperature for 1 hour and then allowed to warm to room temperature. After 16 hours, the reaction mixture was washed with sodium hydrogen carbonate solution (2×50 mL) and brine (50 mL), dried over magnesium sulfate, and concentrated in vacuo to give 2-(tert-butyldimethylsilyloxy)ethylamine as a colourless oil. Yield: 24.1 g, 137 mmol, 92%. $^1$H NMR (400 MHz, CDCl$_3$) δ: 3.63 (2H, t), 2.78 (2H, t), 0.91 (9H, t), 0.07 (6H, s).

Triphosgene (1.675 g, 5.65 mmol) was added portion-wise to a stirred mixture of 2-(tert-butyldimethylsilyloxy)ethylamine (3.00 g, 17.11 mmol) in dichloromethane (25 mL) and saturated sodium hydrogen carbonate solution (25 mL) at 0° C. After 90 minutes, the aqueous layer was removed and the organic layer was washed with brine, dried over magnesium sulfate, and concentrated in vacuo to give a colourless oil which was distilled under high vacuum. The fraction which distilled at 124° C. (2-(tert-butyldimethylsilyloxy)ethyl isocyanate) was collected and used without further characterization or purification.

Crude 2-(tert-butyldimethylsilyloxy)ethyl isocyanate (422 mg, 2.097 mmol) was added drop wise to a solution of 5-diazoimidazole-4-carboxamide (250 mg, 1.823 mmol) in dimethylsulfoxide (2.5 mL) and the reaction mixture was stirred at room temperature. After 16 hours, the crude reaction mixture was applied to reverse phase silica (C18 silica) and eluted with water and then acetonitrile. The acetonitrile fractions were combined and purified by flash column chromatography (SiO$_2$, gradient 0-100% acetonitrile in dichloromethane) to furnish the title compound as a white solid. Yield: 40 mg, 0.12 mmol, 6.5%. LCMS (ES$^+$) m/z 339 (M+H)$^+$ at 3.19 minutes.

$^1$H NMR (400 MHz, d$_6$-DMSO) δ: 8.87 (1H, s), 7.83 (1H, br s), 7.70 (1H, bs), 4.41 (2H, t), 3.98 (2H, t), 0.78 (9H, t), −0.03 (6H, s).

Synthesis 23

3-(2-Hydroxyethyl)-4-oxo-3,4-dihydroimidazo[5,1-d][1,2,3,5]tetrazine-8-carboxamide (N,N-002)

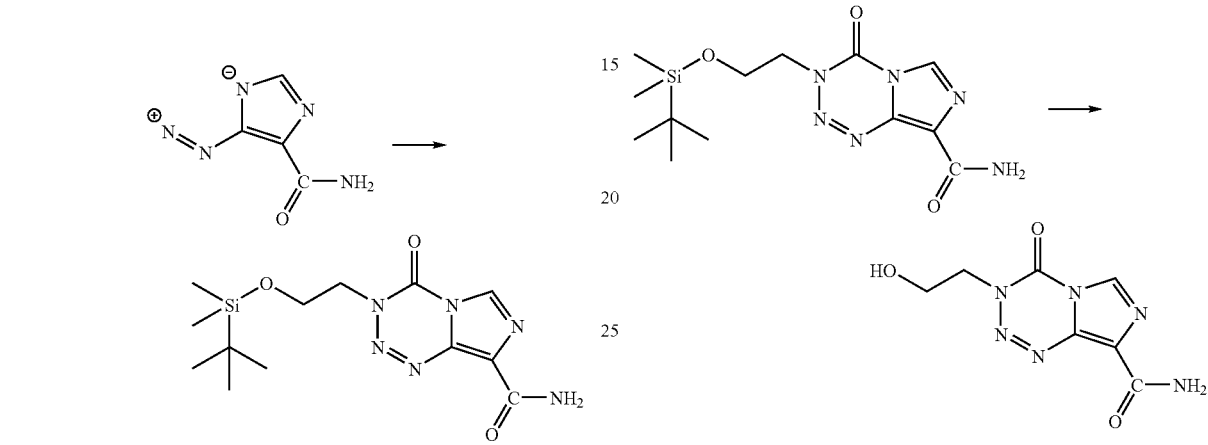

A solution of 3-(2-(tert-butyldimethylsilyloxy)ethyl)-4-oxo-3,4-dihydroimidazo[5,1-d][1,2,3,5]tetrazine-8-carboxamide (50 mg, 0.148 mmol) in THF:AcOH:water (5 mL of a 1:3:1 v/v/v mixture) was stirred at room temperature. After 3 hours, the reaction mixture was concentrated in vacuo and the residue was purified by flash column chromatography (SiO$_2$, gradient 0-100% acetonitrile in dichloromethane) to furnish the title compound as a white solid. Yield: 15 mg, 0.067 mmol, 45%. LCMS (ES$^+$) m/z 225 (M+H)$^+$ at 0.62 minutes. $^1$H NMR (400 MHz, d$_6$-DMSO) δ: 8.84 (1H, s), 7.81 (1H, br s), 7.68 (1H, bs), 4.85 (1H, t) 4.34 (2H, t), 3.79 (2H, q).

Synthesis 24

3-(-1-Phenyl-1-methylethyl)-8-carbamoylimidazotetrazin-4-one (BB-006)

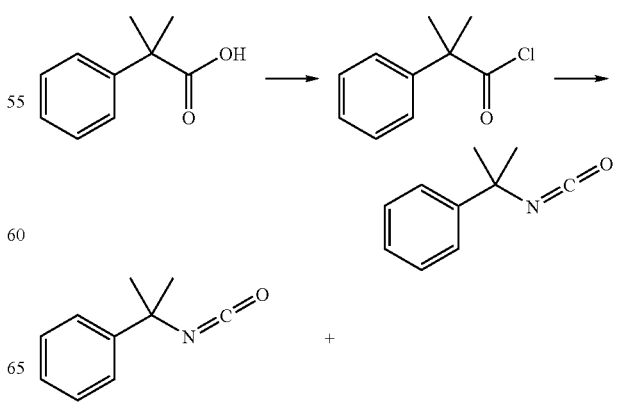

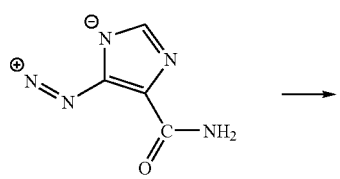

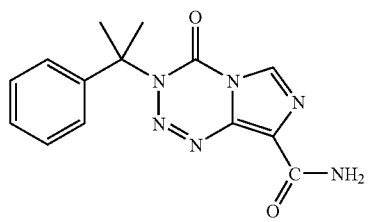

Thionyl chloride (1.33 mL, 18.27 mmol) was added drop wise to α,α-dimethylphenylacetic acid (Alfa Lancaster) (2.0 g, 12.18 mmol) and the mixture heated at reflux. After 5 hours, the thionyl chloride was removed by distillation at 78° C., then by co-evaporation with toluene at 110° C. The residue (α,α-dimethylphenylacetyl chloride) was used in the next step without further purification.

A solution of α,α-dimethylphenylacetyl chloride (2.225 g, 12.18 mmol) in toluene (10 mL) was added drop wise to a stirred solution of sodium azide (1.19 g, 2.27 mmol) in water (10 mL) at 0° C. On completion of the addition the stirred mixture was allowed to warm to room temperature. After 16 hours, the aqueous layer was removed and the toluene solution was washed with sodium hydrogen carbonate solution (2×5 mL), ice-cold water (5 mL) and brine (5 mL) and dried over magnesium sulfate. The solution was added drop wise to toluene (10 mL) which was preheated to 85° C. and heating continued after completion of the addition. After 2 hours, the toluene was removed by distillation at atmospheric pressure and the product was distilled at reduced pressure (high vacuum line) at 60° C. to furnish 1.1 g of a colourless oil (α,α-dimethylbenzyl isocyanate) which was used without further purification.

Crude α,α-dimethylbenzyl isocyanate (0.68 mL, 4.2 mmol) was added drop wise to a suspension of 5-diazoimidazole-4-carboxamide (0.5 g, 3.65 mmol) in dry dimethylsulfoxide (5 mL) under nitrogen and the reaction mixture was stirred at room temperature. After 16 hours, the reaction mixture was poured onto ice and extracted with dichloromethane (3×25 mL). The organic extracts were washed with water (25 mL), dried over sodium sulfate and evaporated to dryness. The residue was purified by flash column chromatography (SiO$_2$, gradient 0-100% acetonitrile in dichloromethane) and triturated with ether to furnish the title compound as a white solid. Yield: 30 mg, 0.10 mmol, 3%. LCMS (ES$^+$) m/z 299 (M+H)$^+$ at 2.46 minutes. $^1$H NMR (400 MHz, d$_6$-DMSO) δ: 8.66 (1H, s), 7.78 (1H, br s), 7.66 (1H, bs), 7.37 (2H, m), 7.31 (2H, m), 7.24 (2H, m), 2.00 (6H, s).

Synthesis 25

3-(2-Methoxybenzyl)-4-oxo-3,4-dihydroimidazo[5,1-d][1, 2, 3, 5]tetrazine-8-carboxamide (AA-001)

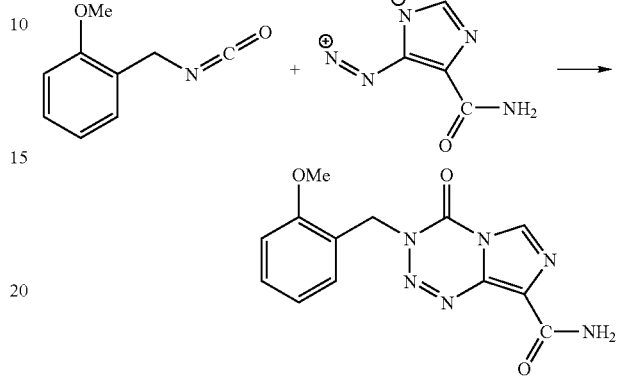

Ortho-methoxybenzyl isocyanate (Sigma Aldrich) (0.390 g, 2.4 mmol) was added drop wise to a suspension of 5-diazoimidazole-4-carboxamide (0.274 g, 2 mmol) in dry DMSO (2.5 mL) at room temperature under nitrogen. The resulting mixture was stirred at room temperature overnight. The reaction was quenched by the addition of ice and the solid product (off-white) removed by filtration, washed with water and ethyl acetate then recrystallised from chloroform/hexane. Yield: 0.343 g, 57%. IR v$_{max}$/cm$^{-1}$ 3460, 3094, 1728, 1683, 1589, 1454. $^1$H NMR δ$_H$ (DMSO-d$_6$) 5.45 (2H, s, CH$_2$Ar), 6.91 (1H, td, J 7.5, 0.8, ArH), 7.06 (1H, d, J 7.8, ArH), 7.27 (1H, d, J 7.5, 1.4, ArH), 7.30-7.33 (1H, m, ArH), 7.69 (1H, br s, NH), 7.81 (1H, br s, NH), 8.84 (1H, s, 6-H). δ$_C$ 47.9, 56.0, 111.3, 120.7, 123.7, 129.1, 129.4, 129.7, 131.4, 134.9, 139.6, 157.1, 162.0. MS Found 301.1100. Calc for (M+H): 301.1049. Found C, 51.6; H, 3.9; N, 28.0. Calc. for C$_{13}$H$_{12}$N$_6$O$_3$C, 52.0; H, 4.0; N, 28.0%.

Synthesis 26

4-Oxo-3-(3,4,5-trimethoxybenzyl)-3,4-dihydroimidazo[5,1-d][1,2,3,5]tetrazine-8-carboxamide (AA-002)

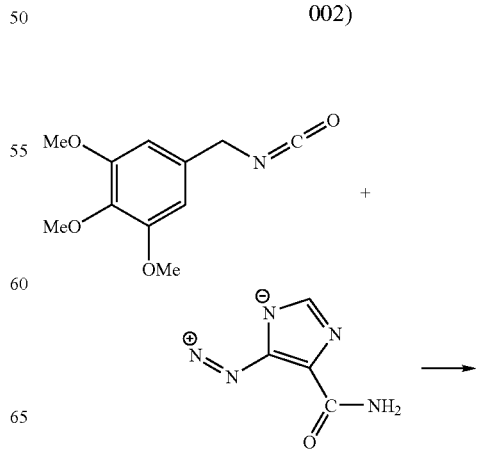

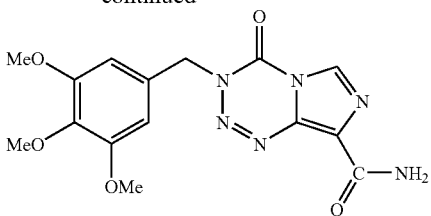

3,4,5-Trimethoxybenzyl isocyanate (Sigma Aldrich) (0.536 g, 2.4 mmol) was added drop wise to a suspension of 5-diazoimidazole-4-carboxamide (0.274 g, 2 mmol) in dry dimethylsulfoxide (2.5 mL) at room temperature under nitrogen. The resulting mixture was stirred at room temperature overnight. The reaction was quenched by the addition of ice and the solid product removed by filtration, washed with water and ethyl acetate, and then recrystallised from chloroform/hexane to give an off-white powder. Yield: 0.323 g, 45%. IR $v_{max}$/cm$^{-1}$ 1740, 1690, 1589. $^1$H NMR $\delta_H$ (DMSO-d$_6$) 3.64 (3H, s, 4-OMe), 3.76 (6H, s, 3,5-OMe), 5.42 (2H, s, CH$_2$Ar), 6.75 (2H, s, ArH), 7.68 (1H, br s, NH), 7.81 (1H, br s, NH), 8.84 (1H, s, 6-H). $\delta_C$ (DMSO-d$_6$) 52.5, 56.4, 60.4, 105.9, 129.4, 131.3, 131.7, 134.9, 137.6, 139.7, 153.4, 162.0. MS Found 361.1300. Calc for (M+H): 361.1260. Found C, 49.5; H, 4.4; N, 23.2. Calc. for C$_{15}$H$_{16}$N$_6$O$_5$C, 50.0; H, 4.5; N, 23.3%.

Synthesis 27

3-(3-Methoxybenzyl)-4-oxo-3,4-dihydroimidazo[5,1-d][1, 2, 3, 5]tetrazine-8-carboxamide (AA-003)

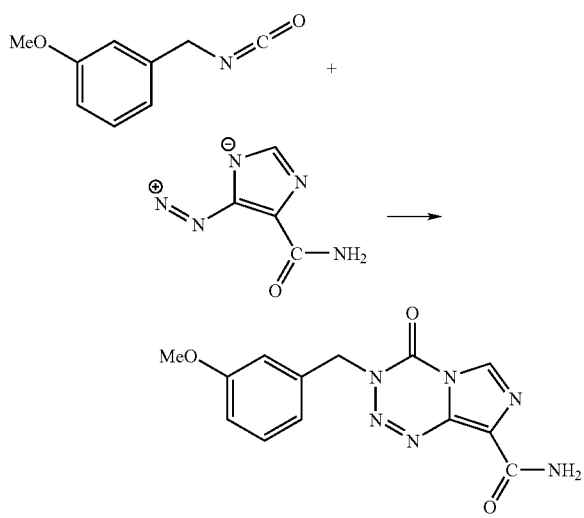

Meta-methoxybenzyl isocyanate (Sigma Aldrich) (0.390 g, 2.4 mmol) was added drop wise to a suspension of 5-diazoimidazole-4-carboxamide (0.274 g, 2 mmol) in dry dimethylsulfoxide (2.5 mL) at room temperature under nitrogen. The resulting mixture was stirred at room temperature overnight. The reaction was quenched by the addition of ice and the solid product (off-white) removed by filtration, washed with water and ethyl acetate, and recrystallised from chloroform. Yield: 0.335 g, 56%. IR $v_{max}$/cm$^{-1}$ 3092, 1730, 1678, 1601. $^1$H NMR $\delta_H$ (DMSO-d$_6$) 3.76 (3H, s, Me), 5.49 (2H, s, CH2Ar), 6.89-6.92 (1H, m, ArH), 7.00-7.02 (1H, m, ArH), 7.28-7.32 (1H, s, ArH), 7.70 (1H, br s, NH), 7.82 (1H, br s, NH), 8.84 (1H, s, 6-H). $\delta_C$ (DMSO-d$_6$) 52.2, 55.6, 113.7, 114.0, 120.4, 129.5, 130.1, 131.4, 134.9, 137.6, 139.7, 159.9, 162.0. Found 301.1091. Calc for (M+H): 301.1049. Found C, 51.3; H 3.9; N 27.8. Calc. for C$_{13}$H$_{12}$N$_6$O$_3$C, 52.0; H, 4.0; N, 28.0%.

Synthesis 28

4-oxo-3-phenethyl-3,4-dihydroimidazo[5,1-d][1,2,3,5]tetrazine-8-carboxamide (DD-001)

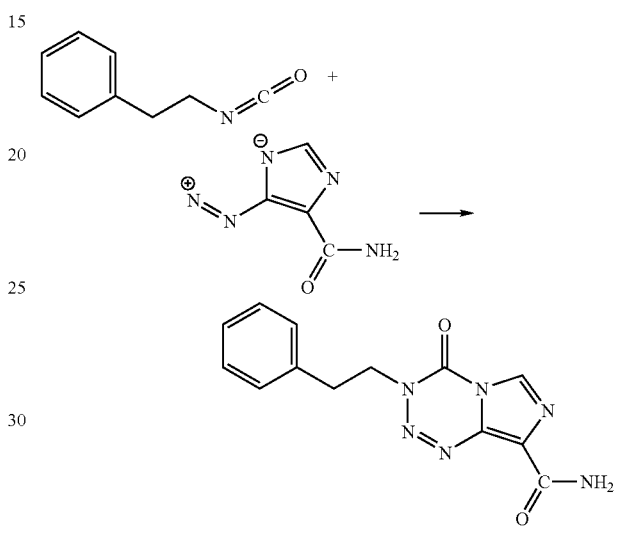

Phenethyl isocyanate (0.441 g, 3 mmol) was added drop wise to a suspension of 5-diazoimidazole-4-carboxamide (0.274 g, 2 mmol) in dry dimethylsulfoxide (2.5 mL) at room temperature under nitrogen. The resulting mixture was stirred at room temperature overnight. The reaction was quenched by the addition of ice and the solid product (pale pink) was removed by filtration, washed with water and ethyl acetate, and recrystallised from chloroform to give the title compound. Yield: 0.259 g, 46%. IR $v_{max}$/cm$^{-1}$ 3132, 1743, 1668. $^1$H NMR $\delta_H$ (DMSO-d$_6$) 3.14 (2H, t, J 7.4, CH$_2$), 4.53 (2H, t, J 7.4, CH$_2$), 7.21-7.33 (5H, m, ArH), 7.68 (1H, br s, NH), 7.81 (1H, br s, NH), 8.83 (1H, s, 6-H). $\delta_C$ 31.1, 34.6, 50.4, 127.1, 129.0, 129.2, 129.3, 131.2, 134.7, 138.2, 139.4, 162.0. MS Found 285.1161. Calc for (M+H): 285.1100. Found C, 55.0; H, 4.3; N, 29.4. Calc. for C$_{13}$H$_{12}$N$_6$O$_3$C 54.9; H 4.3; N, 29.6%.

Synthesis 29

3-(2,4-Dimethoxybenzyl)-4-oxo-3,4-dihydroimidazo[5,1-d][1,2,3,5]tetrazine-8-carboxamide (AA-004)

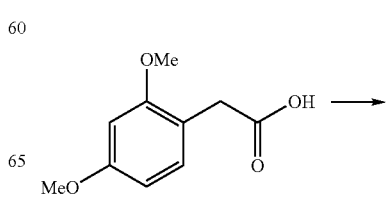

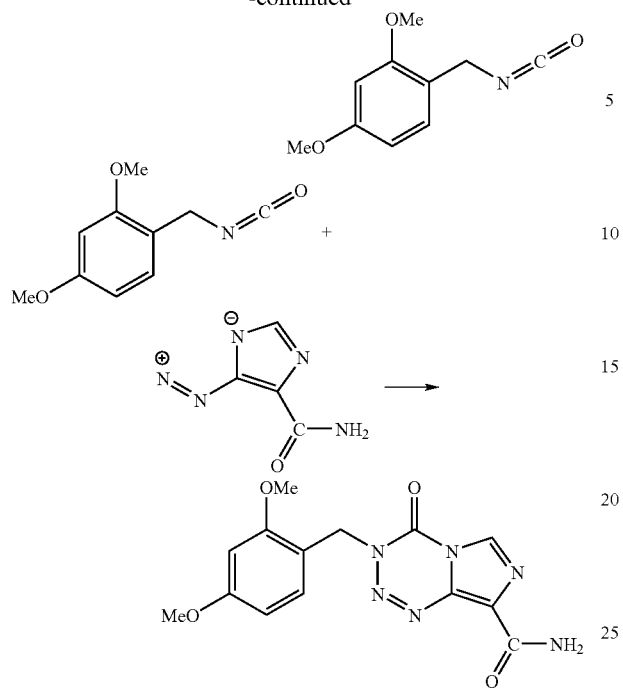

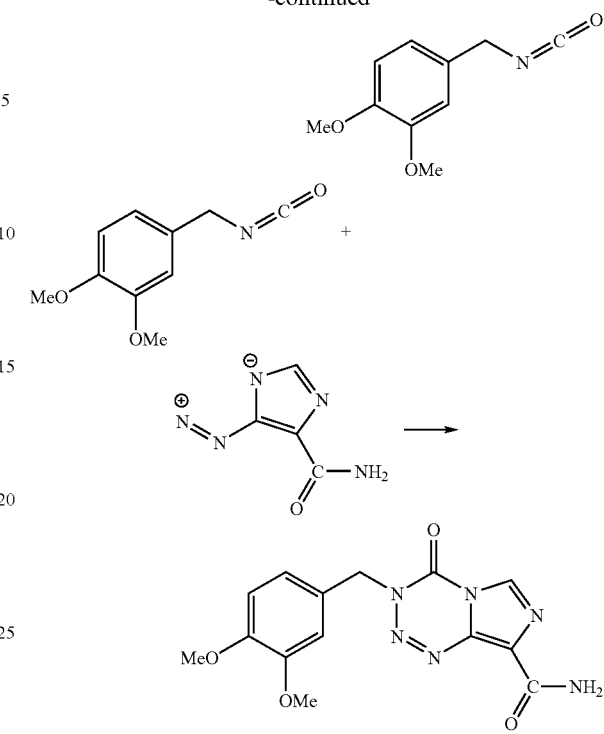

To 2,4-dimethoxyphenylacetic acid (3.92 g, 20 mmol) in dry toluene (100 mL) was added dry triethylamine (2.93 mL, 4.2 mmol) and diphenyl phosphorylazide (4.31 mL, 4 mmol). The mixture was stirred at room temperature for 0.5 hours, and then heated at reflux for a further 3 hours. After cooling, the mixture was concentrated under reduced pressure and purified by distillation using an oil pump to give 2,4-dimethoxybenzyl isocyanate (2.31 g, 60%). IR $v_{max}$/cm$^{-1}$ 2243.

2,4-dimethoxybenzyl isocyanate (0.717 g, 4.4 mmol) was added drop wise to a suspension of 5-diazoimidazole-4-carboxamide (0.548 g, 4 mmol) in dry dimethylsulfoxide (5 mL) at room temperature under nitrogen. The resulting mixture was stirred at room temperature overnight. The reaction was quenched by the addition of ice and the solid product (purple) removed by filtration, washed with water and ethyl acetate and recrystallised from chloroform/hexane to give the title compound. Yield: 0.613 g, 46%. IR $v_{max}$/cm$^{-1}$ 3473, 3121, 1734, 1697, 1605, 1589. $^1$H NMR $\delta_H$ (DMSO-d$_6$) 3.76 (3H, s, OMe), 3.80 (3H, s, OMe), 5.37 (2H, s, CH$_2$Ar), 6.48 (1H, dd, J=8.4, 2.4, ArH), 6.60 (1H, d, J=2.4, ArH), 7.22 (1H, d, J=8.4, ArH), 7.68 (1H, br s, NH), 7.80 (1H, br s, NH), 8.81 (1H, s, 6-H). $\delta_C$ (DMSO-d$_6$) 47.5, 55.8, 56.1, 98.9, 105.1, 115.9, 129.3, 130.7, 131.2, 134.8, 139.4, 158.5, 161.1, 162.0.

To 3,4-dimethoxyphenylacetic acid (0.785 g, 4 mmol) in dry toluene (22.5 mL) was added dry triethylamine (0.425 g, 4.2 mmol) and diphenyl phosphorylazide (1.101 g, 0.86 mL, 4 mmol). The reaction mixture was stirred at room temperature for 0.5 hours, and then heated at reflux for a further 3 hours. After cooling, the mixture was concentrated under reduced pressure and the crude product (3,4-dimethoxybenzyl isocyanate) was used in the next step.

Crude 3,4-dimethoxybenzyl isocyanate (4 mmol) was added to a suspension of 5-diazoimidazole-4-carboxamide (0.274 g, 2 mmol) in dry dimethylsulfoxide (2.5 mL) at room temperature under nitrogen. The resulting mixture was stirred at room temperature overnight. The reaction was quenched by the addition of ice and the solid product was removed by filtration and purified by column chromatography to give the title compound as a white solid. Yield: 0.068 g, 10%. IR $v_{max}$/cm$^{-1}$ 1734, 1686, 1616. $^1$H NMR $\delta_H$ (DMSO-d$_6$) 3.73 (3H, s, OMe), 3.74 (3H, s, OMe), 5.42 (2H, s, CH$_2$Ar), 6.91-6.98 (2H, m, ArH), 7.03 (1H, d, J=1.9, ArH), 7.70 (1H, br s, NH), 7.82 (1H, br s, NH), 8.83 (1H, s, 6-H). $\delta_C$ (DMSO-d$_6$) 52.2, 56.0, 56.0, 112.1, 112.4, 121.1, 128.3, 129.4, 131.3, 134.9, 139.6, 149.1, 149.2, 162.0.

Synthesis 30

3-(3,4-dimethoxybenzyl)-4-oxo-3,4-dihydroimidazo[5,1-d][1,2,3,5]tetrazine-8-carboxamide (AA-005)

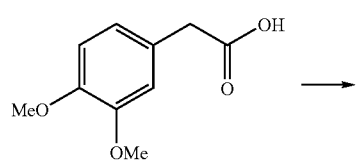

Synthesis 31

4-oxo-3-(thiophen-3-ylmethyl)-3,4-dihydroimidazo[5,1-d][1,2,3,5]tetrazine-8-carboxamide (CC-001)

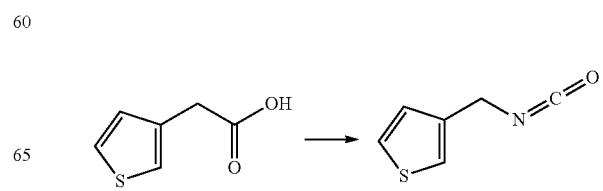

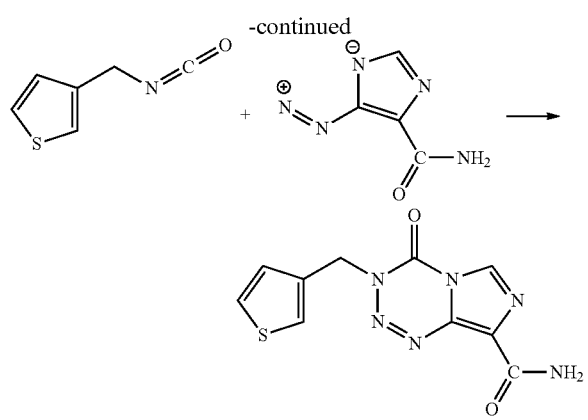

To 3-thiopheneacetic acid (2.84 g, 20 mmol) in dry toluene (22.5 mL) was added dry triethylamine (2.93 mL, 4.2 mmol) and diphenyl phosphorylazide (4.31 mL, 4 mmol). The mixture was stirred at room temperature for 0.5 hours, and then heated at reflux for a further 3 hours. After cooling, the mixture was concentrated under reduced pressure and purified by distillation using an oil pump to give thiophen-3-ylmethyl isocyanate (1.14 g, 40%) as a colourless oil.

Thiophen-3-ylmethyl isocyanate (0.306 g, 2.2 mmol) was added drop wise to a suspension of 5-diazoimidazole-4-carboxamide (0.274 g, 2 mmol) in dry dimethylsulfoxide (2.5 mL) at room temperature under nitrogen. The resulting mixture was stirred at room temperature overnight. The reaction was quenched by the addition of ice and the solid product (off-white) removed by filtration, washed with water and ethyl acetate and air dried. Yield: 0.235 g, 42%. IR $v_{max}$/cm$^{-1}$ 3094, 1728, 1688, 1604. $^1$H NMR $\delta_H$ (DMSO-d$_6$) 5.50 (2H, s, CH$_2$Ar), 7.17 (1H, dd, J 4.9, 1.3, ArH), 7.55-7.58 (2H, m, ArH), 7.70 (1H, br s, NH), 7.83 (1H, br s, NH), 8.85 (1H, s, 6-H). $\delta_C$ (DMSO-d$_6$) 48.0, 124.4, 127.3, 128.0, 129.5, 131.4, 134.9, 136.7, 139.5, 162.0.

Synthesis 32

4-oxo-3-(thiophen-2-ylmethyl)-3,4-dihydroimidazo[5,1-d][1,2,3,5]tetrazine-8-carboxamide (CC-002)

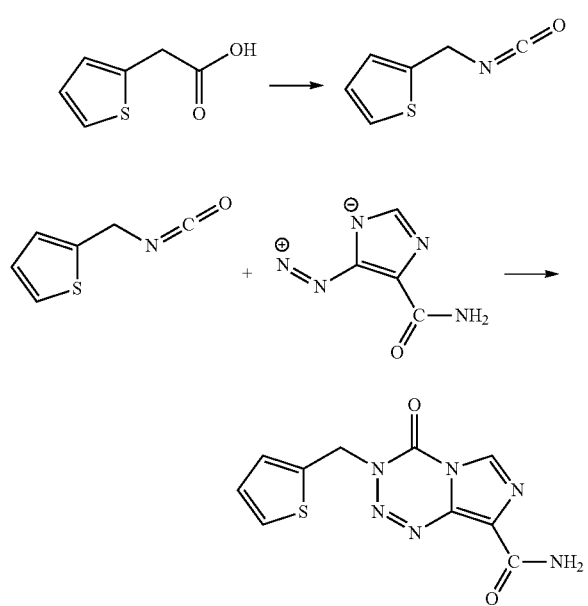

To 2-thiopheneacetic acid (2.84 g, 20 mmol) in dry toluene (22.5 mL) was added dry triethylamine (2.93 mL, 4.2 mmol) and diphenyl phosphorylazide (4.31 mL, 4 mmol). The reaction mixture was stirred at room temperature for 0.5 hours, and then heated at reflux for a further 3 hours. After cooling, the mixture was concentrated under reduced pressure and purified by distillation using an oil pump to give thiophen-2-ylmethyl isocyanate (0.35 g, 12%) as a colourless oil.

Thiophen-2-ylmethyl isocyanate (0.350 g, 2.5 mmol) was added drop wise to a suspension of 5-diazoimidazole-4-carboxamide (0.314 g, 2.3 mmol) in dry dimethylsulfoxide (2.5 mL) at room temperature under nitrogen. The resulting mixture was stirred at room temperature overnight. The reaction was quenched by the addition of ice and the solid product (off-white) was removed by filtration, washed with water and ethyl acetate and air dried to give the title compound. Yield: 0.405 g, 64%. IR $v_{max}$/cm$^{-1}$ 3094, 1732, 1690, 1607. $^1$H NMR $\delta_H$ (DMSO-d$_6$) 5.68 (2H, s, CH$_2$Ar), 7.03 (1H, dd, J=5.1, 3.5, ArH), 7.25 (1H, dd, J=3.5, 1.0, ArH), 7.55 (1H, dd, J=5.1, 1.0, ArH), 7.71 (1H, br s, NH), 7.83 (1H, br s, NH), 8.85 (1H, s, 6-H).

Synthesis 33

3-(Benzyloxy)methyl-8-carbamoylimidazotetrazin-4-one (MM-002)

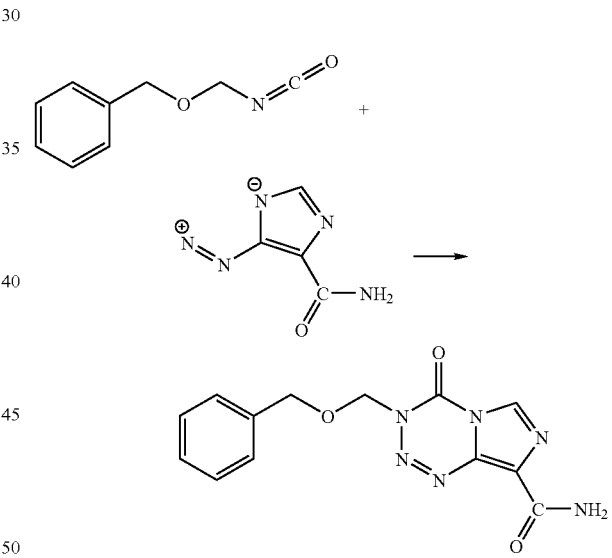

(Benzyloxy)methylisocyanate was prepared according to the procedure described by Balba et al., 1968, J. Agric. Food Chem., Vol. 16, No. 5, pp. 821-825 and used crude.

Crude (benzyloxy)methylisocyanate (4.0 g, 24 mmol) was added drop wise to a suspension of 5-diazoimidazole-4-carboxamide (0.5 g, 3.65 mmol) in dry dimethylsulfoxide (5 mL). The reaction mixture was stirred in the dark at room temperature. After 16 hours, the reaction mixture was poured onto ice (approximately 50 mL) and extracted with dichloromethane (3×50 mL). The organic extracts were dried over magnesium sulfate and evaporated in vacuo. The resulting solid was purified by flash column chromatography (SiO$_2$, gradient 0-100% acetonitrile in dichloromethane) to afford the title compound as a white solid. Yield: 383 mg, 1.25 mmol, 34% yield. LCMS (ES+), m/z 301 (M+H)$^+$ at 2.30 minutes. $^1$H NMR (400 MHz, d$_6$-DMSO) δ: 8.87 (1H, s), 7.84 (1H, br s), 7.71 (1H, br s), 7.25-7.34 (5H, overlapping m), 5.76 (2H, s), 4.71 (2H, s).

Synthesis 34

4-Oxo-3((2-(trimethylsilyl)ethoxy)methyl)-3,4-dihydroimidazo[5,1-d][1, 2, 3, 5]tetrazine-8-carboxamide

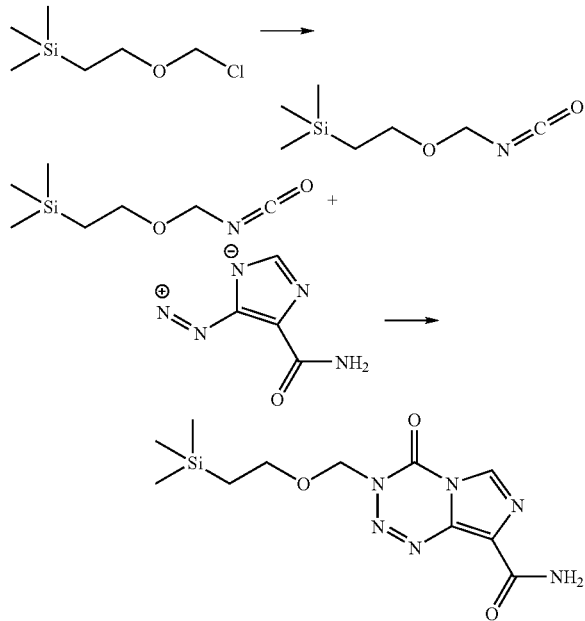

2-(Trimethylsilyl)ethoxymethyl chloride (Fluka) (1.6 mL, 9.04 mmol) was added dropwise to a suspension of silver cyanate (2.03 g, 1.35 mmol, 1.44 eq.) in dry diethyl ether (16 mL) under nitrogen at 0° C. in the dark. The mixture was then allowed to warm slowly to room temperature and was stirred overnight in the dark. The mixture was then filtered over Celite® and the pad of Celite® was washed several times with diethyl ether. The filtrate was concentrated to a small volume (~2-3 mL) by distillation at atmospheric pressure and the crude isocyanate (2-(trimethylsilyl)ethoxymethyl isocyanate) was kept under nitrogen and was used immediately in the next step. IR ($λ_{max}$, cm$^{-1}$): 2955 (w), 2883 (w), 2247 (s), 1249 (m), 1112 (s), 1089 (s), 831 (s).

The concentrated solution of the crude isocyanate in diethyl ether was added dropwise to a suspension of 5-diazoimidazole-4-carboxamide (708 mg, 5.16 mmol) in dimethylsulfoxide (7 mL) at room temperature in the dark. The mixture was then stirred at room temperature in the dark overnight. The reaction mixture became a red homogeneous solution overnight. The mixture was poured into ice and the resulting pale pink suspension was stirred for ~30 minutes. The precipitate was filtered and washed several times with water and dried by suction. The resulting paste was washed several times with diethyl ether until a fine pale pink powder was obtained. 1.27 g of the title compound were obtained (79% based on 5-diazoimidazole-4-carboxamide; 45% over two steps based on 2-(trimethylsilyl)ethoxymethyl chloride). $^1$H NMR (DMSO d$_6$): 8.89 (s, 1H), 7.84 (s, 1H), 7.71 (s, 1H), 5.65 (s, 2H), 3.70-3.75 (t, 2H, J=8.2 Hz), 0.90-0.95 (t, 2H, J=8.2 Hz), 0.00 (s, 9H). The NMR data also showed that the product was pure enough to be used without further purification.

Synthesis 35

3-(Hydroxymethyl)-4-oxo-3,4-dihydroimidazo[5,1-d][1,2,3,5]tetrazine-8-carboxamide (MM-001)

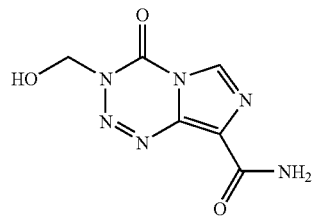 [SMILES: NC(=O)c1ncn2c(=O)n(CO)nnc12]

Boron trifluoride diethyl etherate (BF$_3$.Et$_2$O) (94 μL, 4 eq.) was added dropwise at 0° C. under nitrogen to a suspension of the 2-(trimethylsilyl)ethoxymethyl derivative of Temozolomide (4-oxo-3-((2-(trimethylsilyl)ethoxy)methyl)-3,4-dihydroimidazo[5,1-d][1,2,3,5]tetrazine-8-carboxamide) (60 mg, 0.19 mmol) in chloroform (3.5 mL). The mixture was stirred at 0° C. for 1 hour and was then stirred at room temperature for 1 hour. TLC analysis of the mixture showed completion of the reaction. The mixture was then concentrated to a small volume under vacuum. Diethyl ether was added carefully and the pale pink precipitate was filtered. The resulting white solid/paste was washed several times with diethyl ether and a white solid was obtained. The solid was triturated with diethyl ether with stirring and the precipitate was filtered. The white solid was then washed with ethyl acetate, then diethyl ether and was air-dried. 40 mg of a white solid were obtained. $^1$H NMR (DMSO d$_6$): 8.87 (s, 1H), 7.84 (s, 1H), 7.71 (s, 1H), 5.64 (s, 2H). IR ($λ_{max}$, cm$^{-1}$): 3553 (w), 3462 (w), 3356 (w), 3207 (broad), 3136 (w), 1770 (s), 1662-1653 (m), 1608 (s), 1467 (s), 1400 (w), 1259 (w), 1076 (s, broad), 746 (s). LCMS: crude product 93 to 99% pure. m/z: 210.95 (MH$^+$), 180.95 (MH$^+$—HCHO), 137.94 (100).

On a larger scale, it may be necessary or desirable to add two small portions of boron trifluoride diethyl etherate at room temperature with intervals (e.g., 30 minute intervals) to complete the reaction.

Synthesis 36

3-Methyl-4-oxo-3,4-dihydro-imidazo[5,1-d][1,2,3,5]tetrazine-8-carboxylic acid amide (Temozolomide)

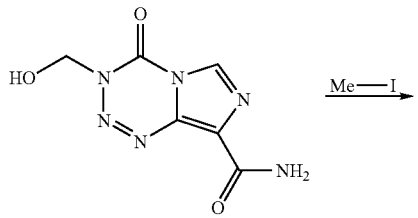

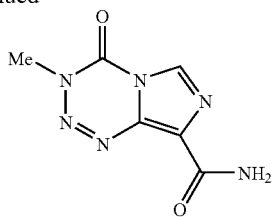

1,8-Diazabicycloundec-7-ene (DBU) (35 μL, 0.228 mmol, 1.2 eq.) was added dropwise to a suspension of the hydroxymethyl derivative of Temozolomide (3-(hydroxymethyl)-4-oxo-3,4-dihydroimidazo[5,1-d][1,2,3,5]tetrazine-8-carboxamide) (40 mg, 0.19 mmol) and iodomethane (2 M solution in tert-butylmethyl ether, 238 μL, 0.475 mmol, 2.5 eq.) in acetonitrile (1 mL). The resulting green suspension became homogeneous and was stirred overnight. The reaction was acidified with 1 N HCl and the yellow solution was extracted four times with ethyl acetate. The combined organic extracts were washed with water and then dried over $MgSO_4$. The solvent was removed under vacuum to give 8 mg of the title compound as a yellow solid (22% crude). The NMR data of the crude product were consistent with the NMR data of temozolomide. $^1$H NMR (DMSO $d_6$): 8.22 (s, 1H), 7.81 (s, 1H), 7.68 (s, 1H), 3.87 (s, 3H). LCMS: 91% pure; m/z: 217.4 (M+Na$^+$).

Synthesis 37

Ethyl 2-(8-carbamoyl-4-oxoimidazo[5,1-d][1,2,3,5]tetrazin-3(4H)-yl)acetate

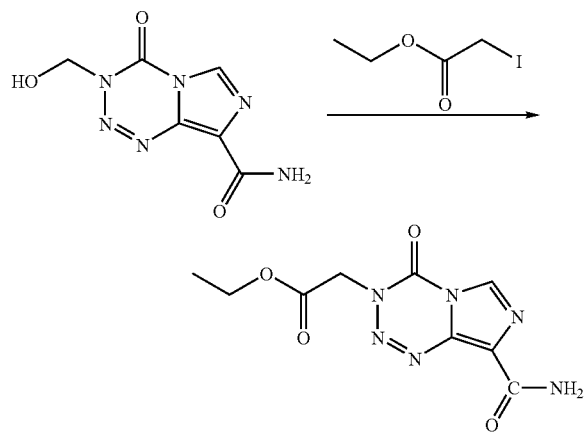

1,8-Diazabicycloundec-7-ene (DBU) (32 μL, 0.215 mmol, 1.5 eq.) was added dropwise to a suspension of the hydroxymethyl derivative of Temozolomide (3-(hydroxymethyl)-4-oxo-3,4-dihydroimidazo[5,1-d][1,2,3,5]tetrazine-8-carboxamide) (30 mg, 0.143 mmol) and ethyl iodoacetate (43 μL, 0.357 mmol, 2.5 eq.) in acetonitrile (700 μL). The resulting green suspension became homogeneous and was stirred overnight. The reaction was acidified with 1 N HCl and the yellow solution was extracted four times with ethyl acetate. The combined organic extracts were washed with water and then dried over $MgSO_4$. The solvent was removed under vacuum and the pale yellow solid was triturated with diethyl ether to remove the excess of ethyl iodoacetate. The precipitate was filtered to give 5 mg of the title compound as a yellow solid (13% crude). $^1$H NMR (DMSO $d_6$): 8.93 (s, 1H), 7.89 (s, 1H), 7.75 (s, 1H), 5.23 (s, 2H), 4.20-4.23 (q, 2H, J=7.1 Hz), 1.22-1.26 (t, 3H, J=7.1 Hz). LCMS: 97% pure; m/z: 289.4 (M+Na$^+$), 267.5 (MH$^+$).

Synthesis 38

Methyl 2-(8-carbamoyl-4-oxoimidazo[5,1-d][1,2,3,5]tetrazin-3(4H)-yl)acetate (LL-003)

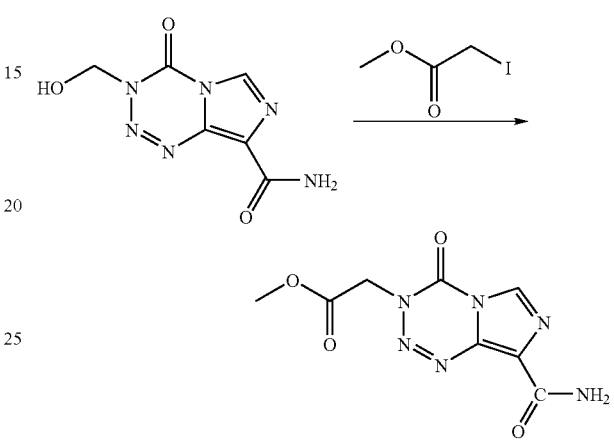

1,8-Diazabicycloundec-7-ene (DBU) (200 μL, 1.34 mmol, 4.1 eq.) was added dropwise to a suspension of the hydroxymethyl derivative of temozolomide (200 mg, 0.95 mmol) and methyl bromoacetate (360 μL, 3.81 mmol, 4 eq.) in acetonitrile (5 mL). The resulting green suspension became homogeneous and was stirred overnight. The reaction was acidified with 1 N HCl and the yellow solution was extracted four times with ethyl acetate. The combined organic extracts were washed with water and then dried over $MgSO_4$. The solvent was removed under vacuum and the pale yellow solid was triturated with diethyl ether to remove the excess of methyl bromoacetate. The precipitate was filtered and washed with diethyl ether and 62 mg of a pale yellow/green solid were obtained (26% crude). A pure sample was obtained by purification by flash chromatography (MeCN: DCM 50:50) and 43 mg of a white solid were obtained. $^1$H NMR ($d_6$ DMSO): 8.94 (s, 1H), 7.91 (s, 1H), 7.77 (s, 1H), 5.26 (s, 2H), 3.76 (s, 3H). LCMS: crude product 95.2% pure; m/z: 527.3 (2M+Na)$^+$, 275.3 (M+Na)$^+$, 253.4 (MH)$^+$, 151.4 (100).

Synthesis 39

4-Oxo-3-(2-oxobutyl)-3,4-dihydroimidazo[5,1-d][1,2,3,5]tetrazine-8-carboxamide (QQ-001)

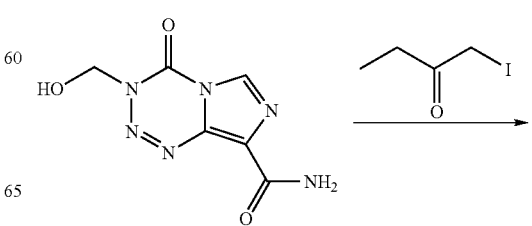

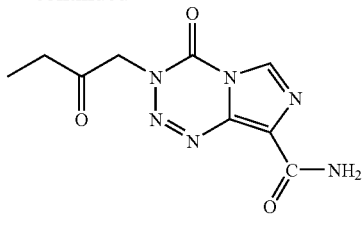

1,8-Diazabicycloundec-7-ene (DBU) (150 μL, 1.00 mmol, 1.4 eq.) was added dropwise to a suspension of the hydroxymethyl derivative of temozolomide (150 mg, 0.71 mmol) and 1-bromo-2-butanone (90%, stabilized with CaCO$_3$) (330 μL, 2.91 mmol, 4.1 eq.) in acetonitrile (4 mL). The resulting green suspension became homogeneous and was stirred overnight. The reaction was acidified with 1 N HCl and the yellow solution was extracted four times with ethyl acetate. The combined organic extracts were washed with water and then dried over MgSO$_4$. The solvent was removed under vacuum and the pale yellow solid was triturated with diethyl ether to remove the excess of 1-bromo-2-butanone. The precipitate was filtered and washed with diethyl ether and 59 mg of a pale yellow/green solid were obtained (33% crude). LCMS: crude product (99.5% pure); m/z: 523.4 (2M+Na)$^+$, 273.2 (M+Na)$^+$, 251.3 ((MH$^+$)$^+$, 100). $^1$H NMR (d$_6$ DMSO): 8.90 (s, 1H), 7.90 (s, 1H), 7.75 (s, 1H), 5.37 (s, 2H), 2.67-2.72 (q, 2H, J=7.2 Hz), 0.99-1.03 (t, 3H, J=7.2 Hz).

Synthesis 40

3-Cyclopropylmethyl-8-carbamoylimidazotetrazin-4-one (GG-003)

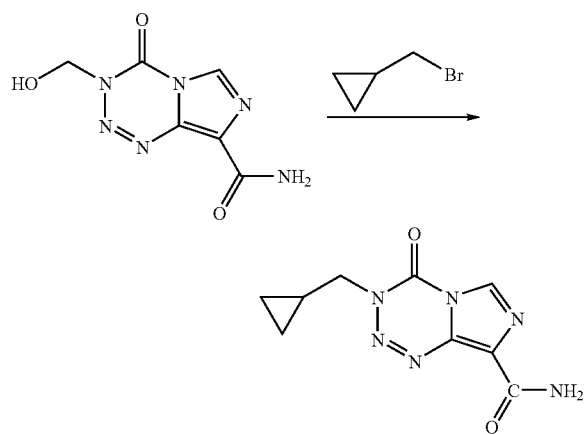

1,8-Diazabicyclo[5.4.0]undec-7-ene (DBU) (0.164 mL, 0.666 mmol) was added dropwise to a suspension of 3-(hydroxymethyl)-8-carbamoylimidazotetrazin-4-one (0.1 g, 0.476 mmol) and (bromomethyl)cyclopropane (0.185 mL, 1.903 mmol) in acetonitrile (2.3 mL). After four days, the resulting black reaction mixture was acidified with 1 M HCl and extracted with ethyl acetate (3×10 mL). The combined organic layers were washed with water (10 mL), dried over MgSO$_4$, filtered, and concentrated in vacuo. The residue was triturated with ether and purified by flash column chromatography (SiO$_2$, gradient 0-100% acetonitrile in dichloromethane) to afford the target compound as a pale green solid. Yield 13.2 mg, 0.056 mmol, 12. LCMS (ES$^+$) m/z 235 (M+H)$^+$ at 2.23 min. $^1$H NMR (400 MHz, d$_6$-DMSO) δ: 8.81 (1H, s), 7.79 (1H, br s), 7.67 (1H, bs), 4.18 (2H, d), 1.32 (1H, m), 0.56 (2H, m), 0.46 (2H, m).

Synthesis 41

2,2-Dimethyl-propionic acid 8-carbamoyl-4-oxo-imidazo[5,1-d][1,2,3,5]tetrazin-3-ylmethyl ester (LL-004)

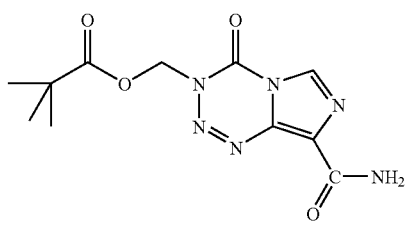 [SMILES: CC(C)(C)C(=O)OCn1nnc2c(C(N)=O)ncn2c1=O]

1,8-Diazabicyclo[5.4.0]undec-7-ene (DBU) (200 μL, 1.34 mmol, 1.4 eq.) was added dropwise to a suspension of 3-(hydroxymethyl)-8-carbamoylimidazotetrazin-4-one (200 mg, 0.95 mmol) and chloromethyl pivalate (1.65 mL, 11.5 mmol, 12.1 eq.) in acetonitrile (5.5 mL). The resulting light brown suspension became homogeneous and was stirred overnight. The reaction was acidified with 1 N HCl and the crude product was extracted four times with ethyl acetate. The combined organic extracts were washed with water and then dried over MgSO$_4$. The solvent was removed under vacuum and the mixture was triturated with a hexane:diethyl ether mixture to precipitate the crude product. The organic layer was removed with a pipette and ether was added to induce further precipitation of the product and the organic layer was removed with a pipette. This was repeated several times in order to remove the excess of chloromethyl pivalate and 59 mg of a yellow solid were obtained after filtration of the product. 10 mg of a crude product from a previous synthesis were combined for purification by flash chromatography (MeCN:DCM 50:50) and 36 mg of the title compound were obtained as a yellow solid (11% isolated yield). MS (ES$^+$) m/z 295.1 (M+H)$^+$ (100). $^1$H NMR (400 MHz, d$_6$-DMSO) δ: 8.92 (1H, s), 7.87 (1H, s), 7.73 (1H, s), 6.25 (2H, s), 1.17 (9H, s).

Synthesis 42

3-(3-Methyl-[1,2,4]oxadiazol-5-ylmethyl)-4-oxo-3,4-dihydro-imidazo[5,1-d][1,2,3,5]tetrazine-8-carboxylic acid amide (CC-003)

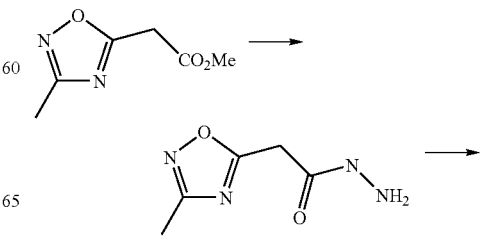

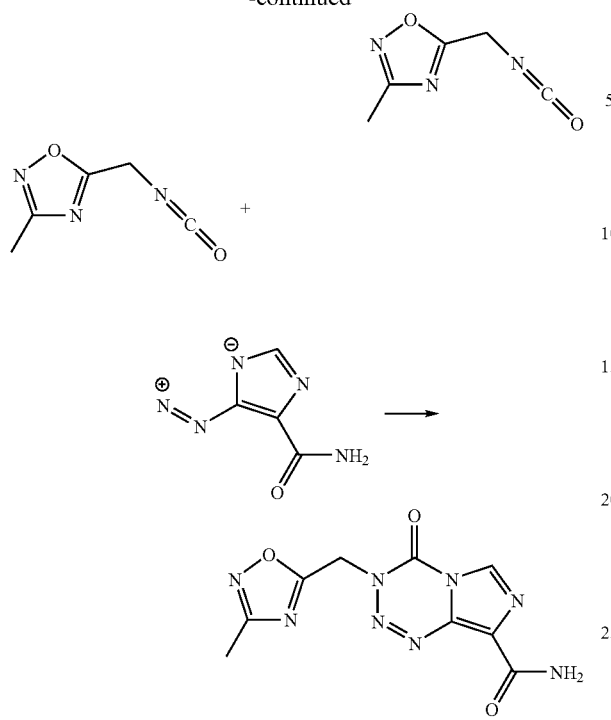

Hydrazine hydrate (75 µL, 64% in water) was added to a solution of 3-methyl[1,2,4]oxadiazol-5-yl)-acetic acid methyl ester (160 mg, 1.02 mmol) in EtOH (1 mL). The resultant mixture was heated to reflux for 1 hour whereupon it was cooled to room temperature and concentrated in vacuo. Et$_2$O was added to the mixture which was then cooled to 0° C. The resulting yellow precipitate was collected by filtration and washed with cold Et$_2$O to give (3-methyl-[1,2,4]oxadiazol-5-yl)acetic acid hydrazide (quantitative yield) in suitably pure form to be used without any further purification.

An aqueous solution of NaNO$_2$ (84 mg, 1.2 mmol) was added to a cooled (0° C.) solution of (3-methyl-[1,2,4]oxadiazol-5-yl)-acetic acid hydrazide (1.02 mmol) in a 1:1 mixture of CH$_2$Cl$_2$:1M HCl (1.5 mL). The reaction mixture was stirred at this temperature for 5 minutes before being poured onto crushed ice. The crude azide was extracted with CH$_2$Cl$_2$ and then dried (MgSO$_4$), filtered and concentrated in vacuo. Toluene (1.5 mL) was added to the crude residue and the resultant mixture heated to 80° C. for 1 hour whereupon it was cooled and concentrated in vacuo to give a crude orange residue corresponding to 5-isocyanatomethyl-3-methyl-[1,2,4]oxadiazole (quantitative yield assumed) ($^1$H NMR (400 MHz, CDCl$_3$) δ ppm: 4.56 (2H, s), 2.36 (3H, s). IR ($\mu_{max}$, cm$^{-1}$): 2260.7 (s, N=C=O), 1593.3 (m), 1494.9 (m), 1435.1 (w), 1325.1 (m)) which was then diluted in DMSO (1.5 mL) and added to a solution of 5-diazoimidazole-4-carboxamide (355 mg, 2.58 mmol) in 3.5 mL DMSO. The reaction mixture was stirred at room temperature for 10 minutes before the addition of sufficient ice water to cause precipitation of the crude product which was collected by vacuum filtration and washed with EtOH (1 reaction volume and then Et$_2$O (1 reaction volume) to give the title compound as a yellow solid (56% yield). $^1$H NMR (400 MHz, d$_6$-DMSO) δ ppm: 8.92 (1H, s), 7.88 (1H, s), 7.74 (1H, s), 5.89 (2H, s), 2.34 (3H, s).

MS (ES$^+$): 277.08 (MH$^+$, 100).

Synthesis 43

3-(3-Methyl-isoxazol-5-ylmethyl)-4-oxo-3,4-dihydro-imidazo[5,1-d][1,2,3,5]tetrazine-8-carboxylic acid amide (CC-004)

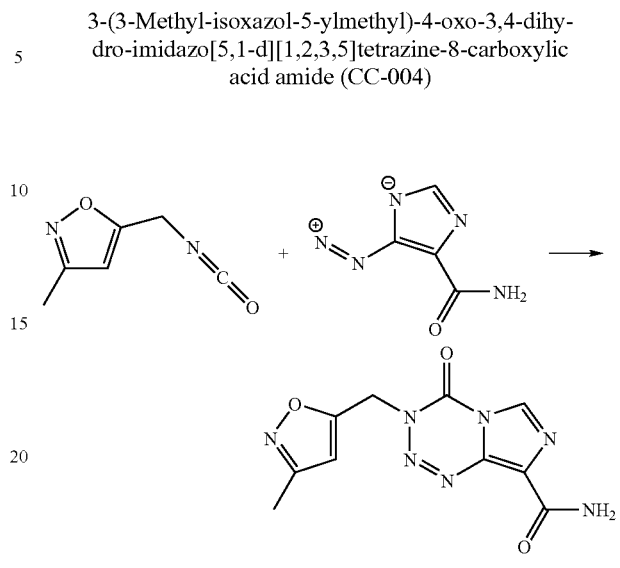

5-Isocyanatomethyl-3-methyl-isoxazole (735 mg, 5.32 mmol) was diluted in DMSO (1.5 mL) and added to a solution of 5-diazoimidazole-4-carboxamide (250 mg, 1.83 mmol) in 2 mL DMSO. The reaction mixture was stirred at room temperature for 16 hours before the addition of sufficient ice water to cause precipitation of the crude product which was collected by vacuum filtration and washed with Et$_2$O (1 reaction volume title compound as a yellow solid (503 mg, 98% yield). $^1$H NMR (400 MHz, d$_6$-DMSO) δ ppm: 8.86 (1H, s), 7.84 (1H, s), 7.71 (1H, s), 6.51 (1H, s), 5.64 (2H, s), 2.21 (3H, s).

Synthesis 44

4-Oxo-3-(1H-[1,2,3]triazol-4-ylmethyl)-3,4-dihydro-imidazo[5,1-d][1,2,3,5]tetrazine-8-carboxylic acid amide (CC-005)

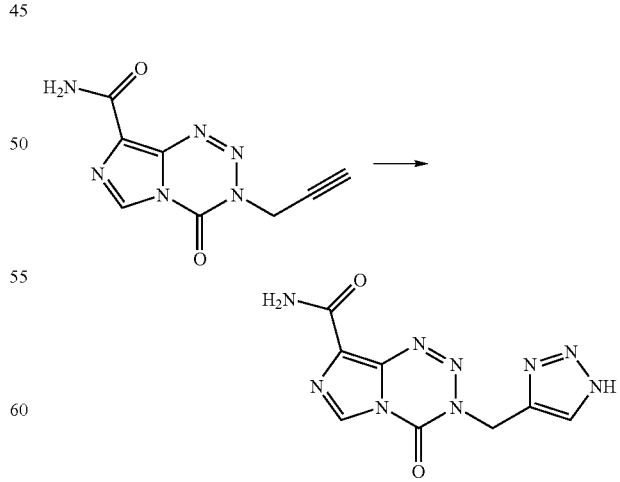

To an aqueous suspension of 3-propargyl-8-carbamoylimidazotetrazin-4-one (EE-001) (100 mg, 0.46 mmol), CuSO$_4$.5H$_2$O (5.7 mg, 0.0229 mmol) in water/t-BuOH (1 mL, 1:1-H$_2$O t-BuOH) was added sodium ascorbate (13.6 mg, 0.0687 mmol) and trimethylsilyl azide (105 μL, 0.802 mmol). The reaction mixture was stirred at room temperature for 72 hours, whereupon it was poured onto crushed ice. The resultant precipitate was filtered, washed with EtOAc and then Et$_2$O to give the title compound (25 mg, 42% yield) as a purple solid. $^1$H NMR (400 MHz, d$_6$-DMSO) δ ppm: 15.1 (1H, s (br)), 8.86 (1H, s), 7.92 (1H, s (br)), 7.81 (1H, s), 7.69 (1H, s), 5.61 (2H, s). MS (ES+): 545.2 ((2M$^+$Na)$^+$, 5), 262.1 (MH$^+$, 80), 126.1 (85), 85.1 (100).

Synthesis 45

3-But-2-ynyl-4-oxo-3,4-dihydro-imidazo[5,1-d][1,2,3,5]tetrazine-8-carboxylic acid amide (EE-002)

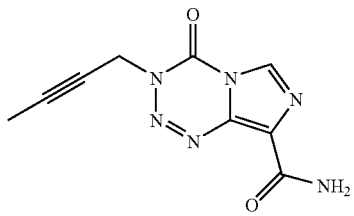 [SMILES: CC#CCn1nnc2c(C(N)=O)ncn2c1=O]

To a cooled solution of 3-(Hydroxymethyl)-4-oxo-3,4-dihydroimidazo[5,1-][1,2,3,5]tetrazine-8-carboxamide (MM-001) (1 equiv) in acetonitrile (0.17 M concentration substrate in solvent) was added the 1-bromo-2-butyne (4 equivs) and DBU (1.4 equivs). The mixture was stirred at this temperature for 30 minutes whereupon it was acidified with 1 N HCl. The mixture was extracted with EtOAc (3×1 reaction volume). The combined organic extracts were combined, dried (MgSO$_4$), filtered and concentrated in vacuo to give an oily residue which was then precipitated from Et$_2$O and washed with further Et$_2$O to give the title compound. $^1$H NMR (400 MHz, d$_6$-DMSO) δ ppm: 8.84 (1H, s), 7.82 (1H, s), 7.70 (1H, s), 5.08 (2H, q, J=2.4 Hz), 1.84 (3H, t, J=2.4 Hz).

Synthesis 46

4-Oxo-3-(3-trimethylsilanyl-prop-2-ynyl)-3,4-dihydro-imidazo[5,1-d][1,2,3,5]tetrazine-8-carboxylic acid amide (EE-003)

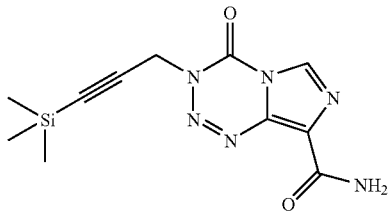 [SMILES: C[Si](C)(C)C#CCn1nnc2c(C(N)=O)ncn2c1=O]

To a cooled solution of 3-(Hydroxymethyl)-4-oxo-3,4-dihydroimidazo[5,1-][1,2,3,5]tetrazine-8-carboxamide (MM-001) (1 equiv) in acetonitrile (0.17 M concentration substrate in solvent) was added 3-bromo-1-(trimethylsilyl)-1-propyne (4 equivs) and DBU (1.4 equivs). The mixture was stirred at this temperature for 30 minutes whereupon it was acidified with 1 N HCl. The mixture was extracted with EtOAc (3×1 reaction volume). The combined organic extracts were combined, dried (MgSO$_4$), filtered and concentrated in vacuo to give an oily residue which was then precipitated from Et$_2$O and washed with further Et$_2$O to give the title compound. $^1$H NMR (400 MHz, d$_6$-DMSO) □ ppm: 8.87 (1H, s), 7.86 (1H, s), 7.72 (1H, s), 5.18 (2H, s), 0.16 (9H, s). LCMS: rt=3.24 min.; m/z: 313.4 (M+Na)$^+$, 291.2 (MH)$^+$, 151.4 (100).

Synthesis 47

3-(2-Methylsulfanyl-ethyl)-4-oxo-3,4-dihydro-imidazo[5,1-d][1,2,3,5]tetrazine-8-carboxylic acid amide (KK-002)

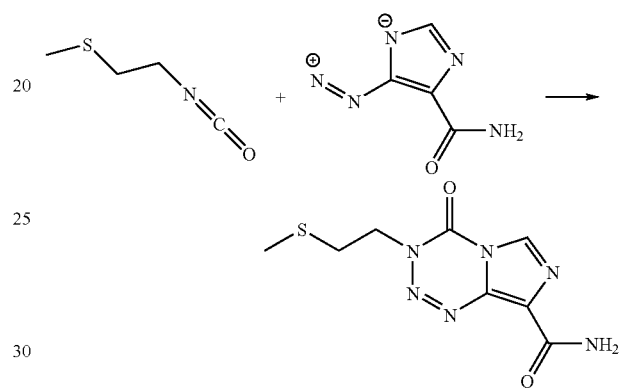

1-Isocyanato-2-methylsulfanyl-ethane (1.09 g, 9.31 mmol) was added drop wise to a suspension of 5-diazoimidazole-4-carboxamide (0.5 g, 3.65 mmol) in dry dimethylsulfoxide (5 mL) at room temperature under nitrogen. The resulting mixture was stirred at room temperature overnight. The reaction was quenched by the addition of ice and the solid product (brown) was removed by filtration, washed with Et$_2$O, and purified using flash chromatography (SiO$_2$) using MeCN:CH$_2$Cl$_2$ (0-100% MeCN) Yield: 52 mg, 26%. $^1$H NMR (400 MHz, d$_6$-DMSO) δ ppm: 8.87 (1H, s), 7.80 (1H, s), 7.66 (1H, s), 4.48 (2H, t), 2.94 (2H, t).

Synthesis 48

(8-Carbamoyl-4-oxo-imidazo[5,1-d][1,2,3,5]tetrazin-3-yl)-acetic acid tert-butyl ester (LL-006)

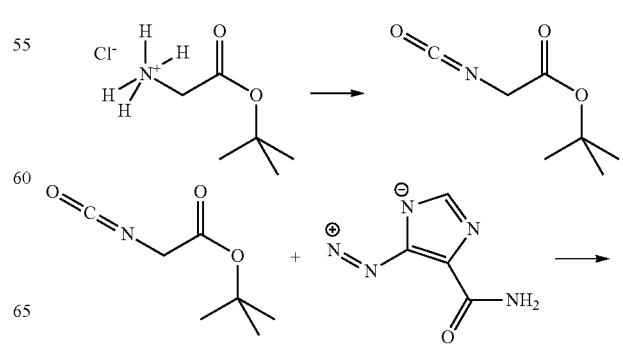

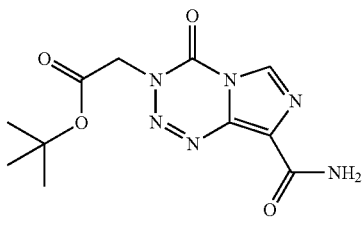

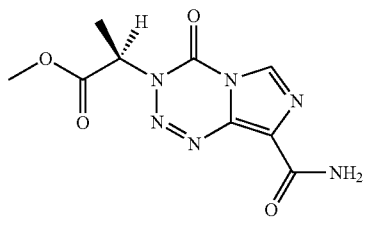

Triphosgene (584 mg, 1.97 mmol) was added to a mixture of glycine t-butyl ester.HCl in CH$_2$Cl$_2$:saturated NaHCO$_3$ (20 mL). The reaction mixture was stirred at 0° C. for 30 minutes before removing the organic phase and extracting further with CH$_2$Cl$_2$ (2×1 reaction volume). The combined organic extracts were dried (MgSO$_4$), filtered and concentrated in vacuo to give a thin oil which was further distilled under reduced pressure (bp 130° C. at 15 mm Hg) to give 642 mg of a clear liquid (68% yield) which was immediately diluted in DMSO (5 mL) before the addition of 5-diazoimidazole-4-carboxamide (480 g, 3.50 mmol) at room temperature under nitrogen. The resulting mixture was stirred at room temperature overnight. The reaction mixture was poured into ice-water (2 reaction volumes) and the resultant precipitate removed by vacuum filtration. The filtercake was washed with water (1 reaction volume), EtOAc (1 reaction volume) and Et$_2$O (1 reaction volume). Finally the crude residue was diluted in a minimum volume of hot EtOAc and recystallised to give the title compound as a pale yellow solid (71% yield, 0.32 g). $^1$H NMR (400 MHz, CDCl$_3$) δ ppm: 8.44 (1H, s), 7.24 (1H, s), 6.01 (1H, s), 5.05 (2H, s), 1.51 (9H, s). Data for tert-butyl 2-isocyanatoacetate: IR (λ$_{max}$, cm$^{-1}$): 2882.1 (w), 2245.2 (s, N=C=O), 1739.9 (s, C=O), 1458.2 (w), 1394.6 (w), 1369.5 (m), 1234.5 (s, C—O—C), 1153.5 (s, C—O—C), 950.9 (m), 908.5 (m), 839.1 (m), 744.6 (m).

Synthesis 49

(R)-2-(8-Carbamoyl-4-oxo-imidazo[5,1-d][1,2,3,5]tetrazin-3-yl)-propionic acid methyl ester (LL-007)

Triphosgene (701 mg, 2.36 mmol) was added to a mixture of L-alanine methyl ester.HCl in CH$_2$Cl$_2$:saturated NaHCO$_3$ (25 mL). The reaction mixture was stirred at 0° C. for 30 minutes before removing the organic phase and extracting further with CH$_2$Cl$_2$ (2×1 reaction volume). The combined organic extracts were dried (MgSO$_4$), filtered and concentrated in vacuo to give a thin oil which was further distilled under reduced pressure (bp 130° C. at 15 mm Hg) to give 642 mg of a clear liquid (68% yield) which was immediately diluted in DMSO (5 mL) before the addition of 5-diazoimidazole-4-carboxamide (480 g, 3.50 mmol) at room temperature under nitrogen. The resulting mixture was stirred at room temperature overnight. The reaction mixture was poured into ice-water (2 reaction volumes) and the resultant precipitate removed by vacuum filtration. The filter cake was washed with water (1 reaction volume), EtOAc (1 reaction volume) and Et$_2$O (1 reaction volume). Finally the crude residue was diluted in a minimum volume of hot EtOAc and recystallised to give the title compound as a pale yellow solid (211 mg). $^1$H NMR (400 MHz, d$_6$-DMSO) δ ppm: 8.90 (1H, s), 7.86 (1H, s), 7.73 (1H, s), 5.73 (1H, q, J=7.2 Hz), 3.71 (3H, s), 1.71 (3H, d, J=7.2 Hz).

Synthesis 50

(S)-2-(8-Carbamoyl-4-oxo-imidazo[5,1-d][1, 2, 3, 5]tetrazin-3-yl)-3-hydroxy-2-methyl-propionic acid methyl ester (LL-008)

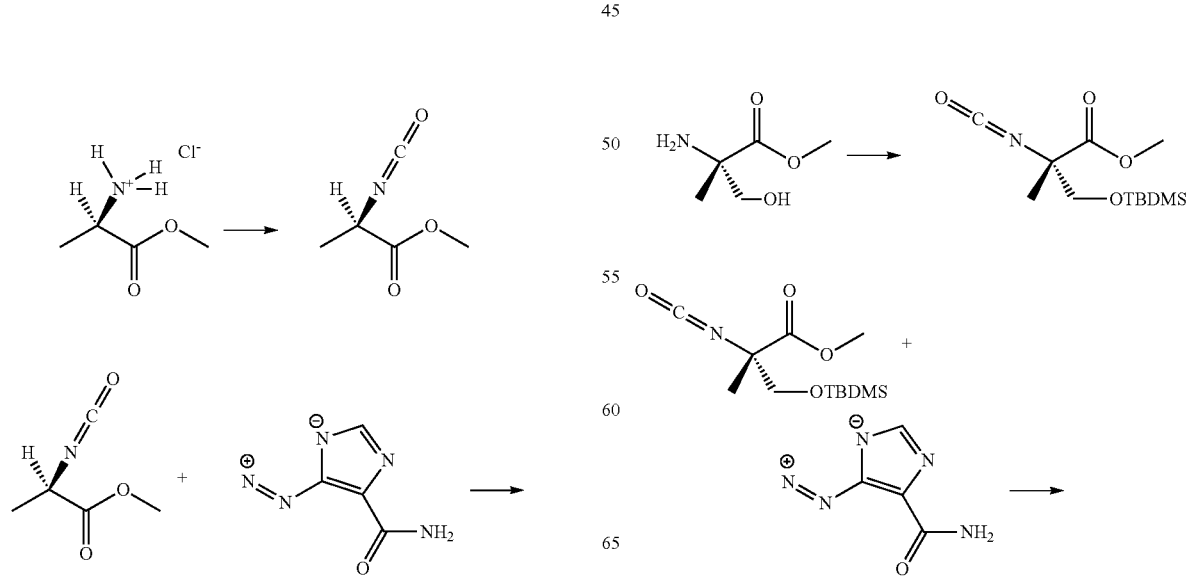

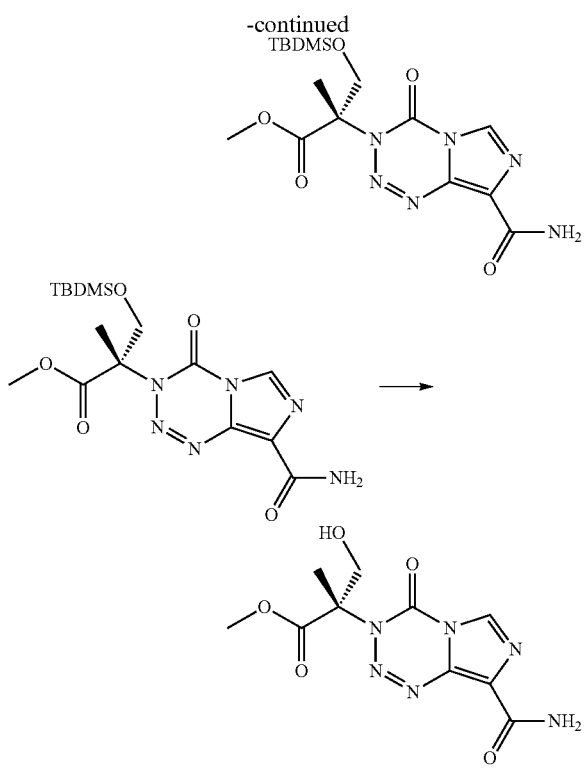

Triphosgene (234 mg, 0.79 mmol) was added portionwise to a biphasic solution of O-silylated serine methyl ester (558 mg, 2.39 mmol) in CH$_2$Cl$_2$ (8 mL) and saturated aqueous NaHCO$_3$ (8 mL). The mixture was stirred for 45 minutes at room temperature before the organic phase was removed. The aqueous faction was extracted further with CH$_2$Cl$_2$ (2×1 reaction volumes). The organic extracts were combined, dried (MgSO$_4$), filtered and concentrated in vacuo to give a thin liquid which corresponded to (S)-3-(tert-butyl-dimethyl-silanyloxy)-2-isocyanato-2-methyl-propionic acid methyl ester and was used without further purification. IR ($\lambda_{max}$, cm$^{-1}$): 2955.0-2930.0-2858.6 (m, C—H), 2249.1-2227.9 (s, N=C=O), 1755.3 (s, C=O), 1464.0 (w), 1438.9 (w), 1251.8-1211.3-1118.8-1072.5 (s, C—O—C), 977.2 (w), 910.4 (w), 835.2-825.6 (s), 777.3 (s), 725.3 (m), 665.5 (m).

To a solution of (S)-3-(tert-butyl-dimethyl-silanyloxy)-2-isocyanato-2-methyl-propionic acid methyl ester (510 mg, 1.86 mmol) in dry DMSO (1.5 mL) was added 5-diazoimidazole-4-carboxamide (135 g, 0.98 mmol) at room temperature under nitrogen. The reaction mixture was stirred for 2 hours whereupon it was poured onto crushed ice. The resultant white precipitate was collected by vacuum filtration. The filter cake was washed with water (2×1 reaction volume), EtOAc (1 reaction volume) and then Et$_2$O (1 reaction volume) to give (S)-3-(tert-Butyl-dimethyl-silanyloxy)-2-(8-carbamoyl-4-oxo-imidazo[5,1-d][1,2,3,5]tetrazin-3-yl)-2-methyl-propionic acid methyl ester as a pale off white solid (140 mg, 34%). $^1$H NMR (400 MHz, d$_6$-DMSO) δ ppm: 8.96 (CH, s, 1H), 7.91 (CONH$_2$, s, 1H), 7.77 (CONH$_2$, s, 1H), 5.77 (CH, dd, J=8.8 Hz, 5.6 Hz, 1H), 4.36 (CH$_2$, dd, J=10.6 Hz, 5.6 Hz, 1H), 4.23 (CH$_2$, dd, J=10.6 Hz, 8.8 Hz, 1H), 3.72 (CO$_2$CH$_3$, s, 3H), 0.72 (SiC(CH$_3$)$_3$, s, 9H), 0.03 (SiCH$_3$, s, 3H), −0.06 (SiCH$_3$, s, 3H).

(S)-3-(tert-Butyl-dimethyl-silanyloxy)-2-(8-carbamoyl-4-oxo-imidazo[5,1-d][1,2,3,5]tetrazin-3-yl)-2-methyl-propionic acid methyl ester (80 mg, 0.21 mmol) was diluted in 1 mL of 1.25 M ethanolic HCl solution. The reaction mixture was then stirred at room temperature for 45 minutes, whereupon the mixture concentrated in vacuo. The crude residue was diluted in Et$_2$O which promoted the formation of a precipitate. The solid was removed by vacuum filtration, washed with Et$_2$O (3×1 reaction volumes) and purified by flash chromatography (SiO$_2$) using CH$_2$Cl$_2$: MeOH (9:1) as eluent to give the title compound (38 mg, 61%) as a white solid. $^1$H NMR (400 MHz, d$_6$-DMSO) δ ppm: 8.94 (1H, s), 7.91 (1H, s), 7.76 (1H, s), 5.70 (1H, dd, J=8.0 Hz, 6.0 Hz), 5.10 (OH, s (br), 1H), 4.11 (2H, multiplet), 3.70 (3H, s).

Synthesis 51

3-(2-Methanesulfonyl-ethyl)-4-oxo-3,4-dihydro-imidazo[5,1-d][1,2,3,5]tetrazine-8-carboxylic acid amide (UU-001)

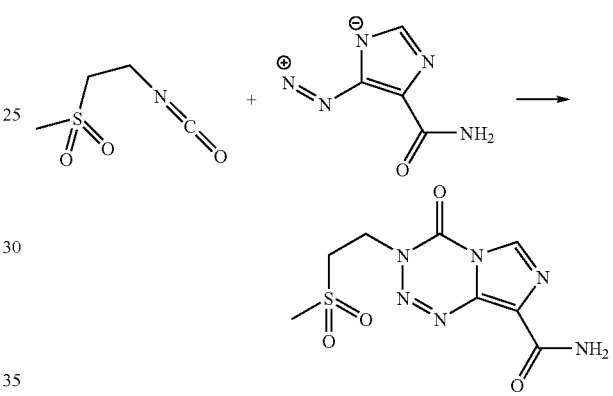

To a solution of 5-diazoimidazole-4-carboxamide (0.5 g, 12.0 mmol) in dry DMSO (5 mL) was added 1-Isocyanato-2-methanesulfonyl-ethane (1.04 g, 3.65 mmol). The mixture was stirred at room temperature for 16 hours, whereupon it was poured onto crushed ice and the resultant precipitate collected by filtration. The filter cake was washed with Et$_2$O (3×1 reaction volume) and dried to give the title compound as an off white solid (990 mg, 95%). $^1$H NMR (400 MHz, d$_6$-DMSO) δ ppm: 8.89 (1H, s), 7.84 (1H, s), 7.71 (1H, s), 4.73 (2H, t, J=6.8 Hz), 3.70 (2H, t, j=6.8 Hz), 2.44 (3H, s).

Synthesis 52

3-Methanesulfonylmethyl-4-oxo-3,4-dihydro-imidazo[5,1-d][1,2,3,5]tetrazine-8-carboxylic acid amide (UU-002)

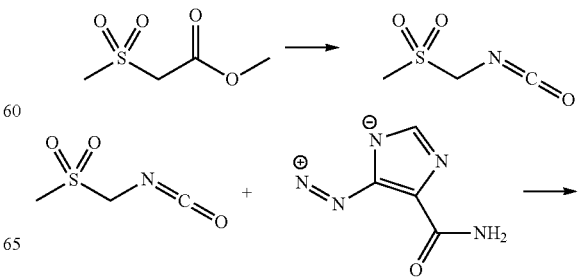

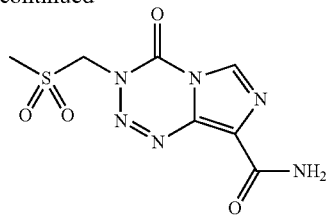

To a solution of methanesulfonyl-acetic acid methyl ester (0.5 μL, 3.71 mmol) in EtOH (4 mL) was added hydrazine hydrate (216 μL, 4.45 mmol). The mixture was refluxed for 90 minutes before being cooled to room temperature, evaporated to dryness in vacuo. The resulting residue was diluted in 1 N HCl and CHCl$_3$ to give a biphasic solution to which aqueous NaNO$_2$ was added dropwise while at 0° C. The mixture was stirred like this for 5 minutes before being extracted with CHCl$_3$ (3×1 reaction volumes). The combined organic extracts were then dried (MgSO$_4$), filtered and concentrated to give a solid residue (256 mg, 51%) which was used without further purification. $^1$H NMR (400 MHz, CDCl$_3$) δ ppm: 4.27 (2H, s), 2.93 (3H, s). IR ($\lambda_{max}$, cm$^{-1}$): 3325.4 (w), 3009.1 (w), 2237.5 (m, N=C=O), 1791.9 (w), 1697.4 (w), 1570.1 (w), 1525.7 (w), 1450.5 (w), 1411.9 (w), 1305.8-1282.7-1126.5 (s, SO$_2$), 922.0 (m), 906.6 (m), 769.6 (m), 634.6 (m).

Isocyanato-methanesulfonyl-methane (250 mg, 1.85 mmol) was added drop wise to a suspension of 5-diazoimidazole-4-carboxamide (210 mg, 1.53 mmol) in dry DMSO (2 mL) at room temperature under nitrogen. The resulting mixture was stirred at room temperature for 72 hours. The reaction was quenched by the pouring onto crushed ice. The resultant precipitate was collected by filtration and washed with Et$_2$O (3 reaction volumes) and dried to give the title compound as a white solid (283 mg, 68%). $^1$H NMR (400 MHz, d$_6$-DMSO) δ ppm: 8.94 (1H, s), 7.90 (1H, s), 7.75 (1H, s), 5.82 (2H, s), 3.15 (3H, s).

Synthesis 53

3-Methanesulfinylmethyl-4-oxo-3,4-dihydro-imidazo[5,1-d][1,2,3,5]tetrazine-8-carboxylic acid amide (UU-003)

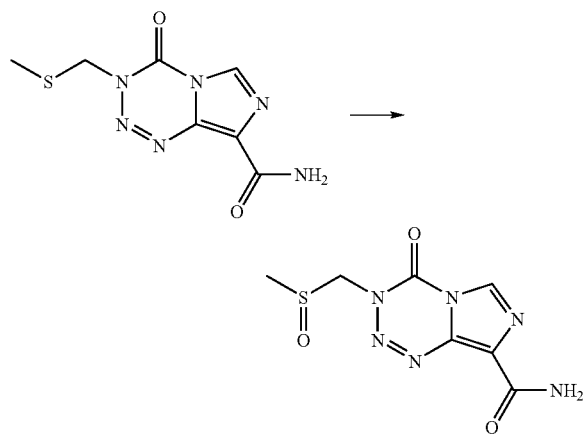

Method A: To a suspension of 3-methylsulfanylmethyl-4-oxo-3,4-dihydro-imidazo[5,1-d][1,2,3,5]tetrazine-8-carboxylic acid amide (Compound KK-001) (40 mg, 0.17 mmol) and FeCl$_3$ (1 mg, 0.005 mmol) in MeCN (1 mL) at room temperature was added periodic acid (42 mg, 0.18 mmol). The mixture was stirred for 75 minutes whereupon it was diluted with saturated Na$_2$S$_2$O$_3$ (1 mL) and then diluted with EtOAc (3 reaction volumes). The mixture was sonicated and the crude product removed by filtration to give a white solid that was then washed with H$_2$O, MeCN, EtOAc and finally Et$_2$O to give a white solid corresponding to the desired product (20 mg, 46%).

Method B: 3-Methylsulfanylmethyl-4-oxo-3,4-dihydro-imidazo[5,1-d][1,2,3,5]tetrazine-8-carboxylic acid amide (Compound KK-001) (50 mg, 0.21 mmol) was solubilised in 5 mL CH$_2$Cl$_2$:MeOH (1:1) and cooled to −78° C. Ozone was gently bubbled through the solution for about 10 minutes until the solution was saturated with O$_3$. the solution was stirred for 3 minutes before nitrogen was bubbled through the reaction mixture to remove the O$_3$. Dimethylsufide (excess) was then added and the resultant mixture stirred for 30 minutes while warming to room temperature. The mixture was concentrated in vacuo and then diluted in Et$_2$O (3 reaction volumes). The resultant precipitate was then removed by filtration, washed with Et$_2$O to give the title compound in pure form (100% yield, 54 mg). $^1$H NMR (400 MHz, d$_6$-DMSO) δ ppm: 8.92 (1H, s), 7.89 (1H, s), 7.74 (1H, s), 5.59 (1H, d, J=13.2 Hz), 5.47 (1H, d, J=13.2 Hz), 2.77 (3H, s). MS (ES$^+$): 257.04 (MH$^+$, 8), 120.05 (72), 79.03 (100).

Synthesis 54

(8-Carbamoyl-4-oxo-imidazo[5,1-d][1,2,3,5]tetrazin-3-ylmethyl)-phosphonic acid diethyl ester (VV-001)

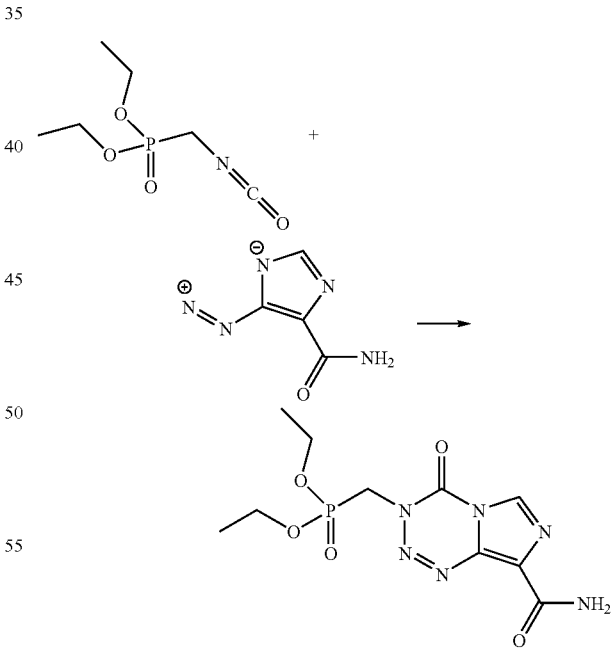

Isocyanatomethyl-phosphonic acid diethyl ester (953 mg, 6.95 mmol) in EtOAc (10 mL) was added drop wise to a suspension of 5-diazoimidazole-4-carboxamide (0.5 g, 3.65 mmol) in dry dimethylsulfoxide (10 mL) at room temperature under nitrogen. The resulting mixture was stirred at room temperature for 16 hours. The mixture was poured into Et$_2$O and the resultant collected by filtration and washed with Et$_2$O (3 reaction volumes) and dried to give the title compound as a solid (1.14 g, 50%). $^1$H NMR (400 MHz, $d_6$-DMSO) δ ppm: 8.91 (1H, s), 7.88 (1H, s), 7.74 (1H, s), 4.85 (2H, t, J=11.2 Hz), 4.12 (4H, m), 1.25 (6H, t, 7.2).

Synthesis 55

(8-Carbamoyl-4-oxo-imidazo[5,1-d][1,2,3,5]tetrazin-3-ylmethyl)-carbamic acid 9H-fluoren-9-ylmethyl ester (WW-001)

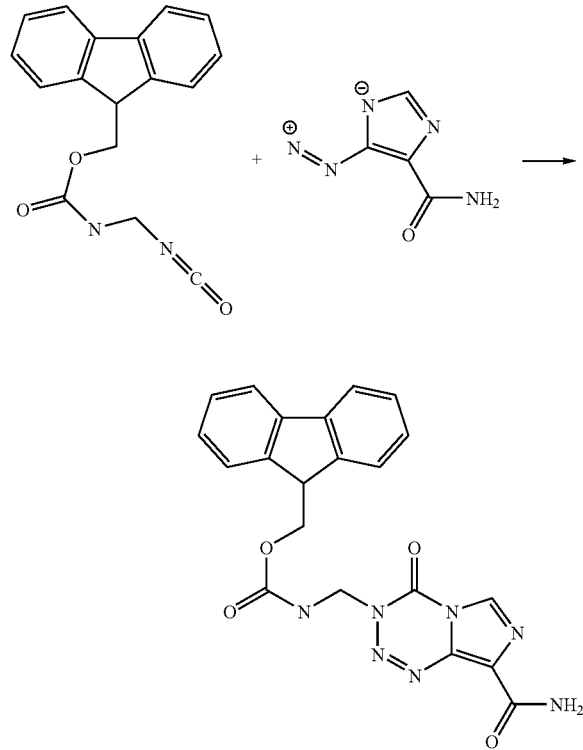 [SMILES: O=C=NCNC(=O)OCC1c2ccccc2-c2ccccc21 ; NC(=O)c1nc[n-]c1N=[NH2+] ; NC(=O)c1ncn2c(=O)n(CNC(=O)OCC3c4ccccc4-c4ccccc43)nnc12]

Isocyanatomethyl-carbamic acid 9H-fluoren-9-ylmethyl ester (1.13 g, 3.83 mmol) was added drop wise to a suspension of 5-diazoimidazole-4-carboxamide (0.5 g, 3.65 mmol) in dry dimethylsulfoxide (5 mL) at room temperature under nitrogen. The resulting mixture was stirred at room temperature overnight. The reaction was quenched by the pouring onto crushed ice. The resultant precipitate was collected by filtration and washed with $Et_2O$ (3 reaction volumes) and dried to give the title compound as a white solid (600 mg, 33.9%). $^1$H NMR (400 MHz, $d_6$-DMSO) δ ppm: 8.86 (1H, s), 8.61 (1H, t-broad), 7.89-7.26 (9H, m), 5.55 (2H, t, J=6.8 Hz), 4.40-4.19 (5H, m), 2.01 (2H, s).

Synthesis 56

3-(2-Methoxyimino-butyl)-4-oxo-3,4-dihydro-imidazo[5,1-d][1,2,3,5]tetrazine-8-carboxylic acid amide (XX-001)

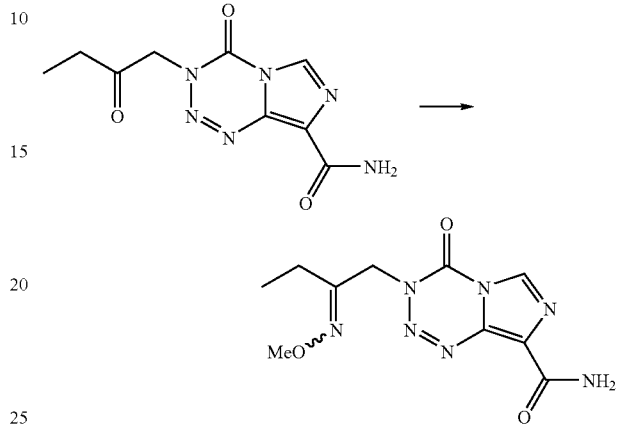

4-Oxo-3-(2-oxo-butyl)-3,4-dihydro-imidazo[5,1-d][1,2,3,5]tetrazine-8-carboxylic acid amide (Compound QQ-001) (25 mg, 0.1 mmol), $MeONH_2 \cdot HCl$ (13 mg, 0.15 mmol) were dissolved in an EtOH; Pyridine solution (1:1-0.5 ml). The reaction mixture was stirred for 16 hours before being concentrated in vacuo to give a crude residue which was redissolved in EtOAc (2 ml) and MeCN (2 mL). The solution was washed with aqueous 1M HCl and then dried ($MgSO_4$), filtered and concentrated in vacuo. The crude product was redissolved in MeCN and passed through a silica plug. The filtrate was concentrated in vacuo to give the desired product as a green solid (17 mg, 61%). $^1$H NMR (400 MHz, $d_6$-DMSO) δ ppm: 8.87 (1H, s), 8.86 (1H, s), 7.84 (2H, s), 7.71 (2H, s), 5.17 (2H, s), 5.04 (2H, s), 3.83 (2.85H, s), 3.73 (3H, s), 2.32 (2H, q, J=7.6 Hz), 2.19 (2H, q, J=7.2 Hz), 1.04 (3H, t, J=7.6 Hz), 0.99 (3H, t, J=7.2 Hz). m/z: 302.3 (($M+Na$)$^+$, 100), 280.4 ($MH^+$).

Biological Methods

General Cell Culture Methods

The cell culture techniques were carried out in a Class II microbiological safety cabinet which was swabbed with 70% IMS in distilled water before each use. Glioma cells were routinely cultured in Costar tissue culture flasks in RPMI 1640 liquid medium (containing 0.3 g/L L-glutamine and 2 g/L sodium bicarbonate) supplemented with 10% heat inactivated FBS (55-59° C.) for 1 hour to denature complement proteins which would otherwise evoke a cellular immune response resulting in cell lysis, 1% non-essential amino acids, 50 μg/mL gentamicin and 400 μg/mL G418 (vector selected reagent). Colorectal and melanoma cells were maintained in RPMI 1640 supplemented with 10% FBS. MRC-5 cells were cultured in EMEM. Cells were grown in a humidified incubator containing 5% $CO_2$ at 37° C. Cells were sub-cultured when growth exceeded approximately 80% confluence, normally twice weekly. The medium was aspirated from the flask and approximately 0.8 mL trypsin-EDTA 1× solution added. The cells were re-incubated at 37° C. until they visibly detached from the flask. The cell suspension was then re-suspended in 5 mL medium and 0.5-1 mL of the cell suspension was transferred to a new flask (25 cm²) with 7 mL culture medium. The cells were further incubated at 37° C. incubator. Cells were disposed after passage nearly 30 times in order to minimize phenotypic drift. New batches of cells were taken from liquid nitrogen storage by thawing rapidly (37° C. water bath) and re-suspension in a 25 cm² flask with 10 mL of culture medium. Two passages were allowed to resume normal growth. For long-term maintenance, viable cells at 60-80% confluence were detached by minimum amount of trypsin/EDTA and re-suspended in sterile filtered freezing medium (95% FBS, 5% DMSO), transferred to sterile cryogenic vials, and frozen overnight at −20° C. followed by −80° C. for 1-2 days and stored in liquid nitrogen for long term storage.

Drug Solutions

Most test compounds, including temozolomide, were prepared as stock solution (100 mM) in DMSO and stored at −20° C. for not more than 6 months.

MTT Assay for 7-Day Toxicity Assay

This assay was first described in Mosmann, T., 1983, "Rapid colorimetric assay for cellular growth and survival: Application to proliferation and cytotoxicity assays", *Journal of Immunological Methods*, Vol. 65, Nos. 1-2, pp. 55-63.

Glioma cell lines, SNB19 and U373, both MGMT transfected (i.e., SNB19M and U373M) and vector controls (i.e., SNB19V and U373V); colorectal carcinoma cell lines, HCT116, HT29, and DLD1; melanoma cell line, SKMEL-28; breast cell line, MCF-7; and normal human fetal lung fibroblast cell line, MRC-5; were harvested at 60-80% confluence—during the logarithmic phase of growth.

Following harvesting, cells in suspension were gently syringed through a 23 gauge needle to obtain a near-single cell suspension. The desired cell seeding densities were used and added into 96-well plates in 180 μL culture medium if only one test compound was to be added, or 160 μL if two test compounds were to be added in combination, which were allowed to attach at 37° C. (5% $CO_2$) overnight. For the 7 day assay, the cell seeding density for different cell lines was as follows: SNB19V, SNB19M: 650 cells/well; U373V, U373M: 650 cells/well; SNB19VR, U373VR: 650 cells/well; HCT116, DLD-1, SKMEL-28, MRC-5, MCF-7: 400 cells/well.

The two peripheral lanes were used as blank wells (cell free) and filled with 200 μL of medium in order to minimise medium evaporation from the plate. A separate time zero ($T_0$) plate was set up alongside other plates. Serial dilutions in tissue culture medium of a 100 mM stock of test compound in DMSO were prepared immediately before each assay to ten times the final concentrations required, and then 20 μL was added to each well (200 μL total media per well) to achieve final concentrations of 0.5 μM, 1 μM, 5 μM, 10 μM, 50 μM, 100 μM, 500 μM, and 1000 μM. A minimum of four wells received the same test compound concentration. To control wells, including those in the $T_0$ plate, 20 μL of medium was added. Previous assays had been carried out to verify that cell viability was not affected by the amount of DMSO added into the test compound-treated wells. A separate plate treated in the same way, but free of test compound, was used as a measure of cell viability at the time of drug addition (day 0).

After incubation at 37° C., 5% $CO_2$ for 7 days (or immediately for the day 0 plate), cell viability was quantified using the MTT assay. 50 μL of sterile filtered MIT (3-(4,5-dimethylthiazol-2-yl)-2,5-diphenyltetrazolium bromide) (2 mg/mL in phosphate buffered saline) were added to each well (final concentration 0.4 mg/mL) and the plates were re-incubated for 4 hours to allow metabolic conversion of MTT by dehydrogenases in viable cells to insoluble formazan crystals. The medium and any unconverted MTT was aspirated, 150 μL of DMSO was added to each well, and the plates were shaken on a plate shaker (Stuart Scientific 503) to ensure complete formazan solubilisation. Absorbance was then read at 550 nm on an Anthos Labtec Systems plate reader and data was automatically transferred to a computer using Deltasoft 3™ software, where the absorbance readings (corrected to background absorbance in blank wells) were displayed.

The intensity of absorbance is directly proportional to cell viability. A linear relationship exists between cell number and the amount of formazan and so the mean absorbance determined for each well of the same concentration can be used as a quantitative measure of viable cells compared to the controls. A graph of absorbance against drug concentration was plotted and the test compound concentration ($GI_{50}$) causing 50% inhibition of control cell growth (absorbance increase from day 0) was calculated by interpolation.

Generation of TMZ Resistant Cell Lines

SNB19V and U373V cell lines were cultured in the presence of incremental concentrations of TMZ (1, 2, 5, 10, 20, 50, 100 μM) (and up to 150 μM for U373V) to generate corresponding TMZ acquired resistant cell lines (i.e., SNB19VR and U373VR). At each step of selection, cells were exposed to a higher TMZ concentration when the re-growth was apparent and labelled as SNB19VR and U373VR, respectively, to distinguish them from the parental cell lines.

Clonogenic Survival Assay

A clonogenic assay, which measures tumour cell survival and subsequent proliferative ability following drug exposure was used to verify that the cells remaining metabolically active following treatment with TMZ and new derivatives. See, e.g., Brown, J. M., et al., 1999, "Apoptosis, p53, and tumor cell sensitivity to anticancer agents", *Cancer Research*, Vol. 59, No. 7, pp. 1391-1399.

Exponentially growing cells were seeded in triplicate at a density of 200 cells/well in 6 well plate and allowed to attach overnight and then exposed to increasing concentration of TMZ and test compounds (0, 5, 10, 100, 500, 1000 μM). After 18 hours, the plates were changed to drug free media and left to grow in the 37° C., 5% $CO_2$ incubator. After 14 days, the plates were rinsed in PBS and fixed with pre-chilled methanol in room temperature for 20 minutes, and then stained with 0.5% methylene blue in 1:1 methanol/$H_2O$ (v/v) for 10 minutes and thoroughly washed in distilled water and air dried. Cell colonies containing >30 cells were counted. Growth inhibition by TMZ and test compounds was estimated by dividing the mean number of colonies under drug treatment by the mean number of colonies without drug treatment.

Biological Data

The biological data are summarised in the following tables.

TABLE 1

Temozolomide

| # | Cell Line | TMZ GI50 (μM) | Average (μM) |
|---|---|---|---|
| 1 | Glioma SNB19V (MGMT−) | 25.3, 24.7, 27.6, 27.6, 33.3, 32.4, 23.4, 52.0, 49.4, 32.5, 64.8, 50.5, 34.1, 27.5, 30.0 | 35.7 |
| 2 | Glioma SNB19M (MGMT+) | 363.8, 394.0, 661.6, 476.9, 572.7, 414.6, 464.3, 459.5, 454.4, 339.2, 470.1, 567.5 | 470.0 |
| 3 | Glioma U373V (MGMT low) | 92.9, 41.9, 43.6, 68.4, 40.0, 34.5, 38.3, 143, 123.2, 55.3, 88.7, 62.4, 36.3, 64.9, 86.0 | 68.0 |

TABLE 1-continued

Temozolomide

| # | Cell Line | TMZ GI50 (µM) | Average (µM) |
|---|---|---|---|
| 4 | Glioma U373M (MGMT+) | 372.2, 238.5, 449.3, 412.4, 519.1, 389.7, 243.6, 248.5, 413.6, 400.1, 369.0 | 368.7 |
| 5 | Colon HCT116 (MMR mutated) | 607.4, 570.1, 594.4 | 590.6 |
| 6 | Colon HT29 (MMR proficient) | 701.6, 577.7 | 639.7 |
| 7 | Colon DLD1 | 435.3 | 435.3 |
| 8 | Melanoma SKMEL-28 (MMR proficient) | 418.9, 443.0 | 431.0 |
| 9 | Breast MCF-7 (MMR proficient) | 342.3, 423.6 | 383.0 |
| 10 | Glioma SNB19VR (MGMT−) (TMZ resistant) | 313.9, 251.4, 274.8, 282.0, 282.5, 293.7, 263.1 | 280.2 |
| 11 | Glioma U373VR (MGMT low) (TMZ resistant) | 316.2, 293.1, 233.6, 327.8, 299.1, 257.5, 325.8, 257.1 | 288.8 |
| 12 | Normal Human Fetal Lung Fibroblast MRC-5 | 441.0, 457.8 | 449.4 |

TABLE 2

Aryl-Alkyl Compounds

| # | Cell Line | TMZ GI50 (µM) | AA-001 GI50 (µM) | AA-002 GI50 (µM) | AA-003 GI50 (µM) | AA-005 GI50 (µM) | PX-004 GI50 (µM) |
|---|---|---|---|---|---|---|---|
| 1 | Glioma SNB19V (MGMT−) | 35.7 | 212.0, 66.7 | 210.0, 64.2, 65.2, 17.6 | 264.0, 46.8, 71.1, 222.4 | 217.5, 113.7 | 31.7, 71.0 |
| 2 | Glioma SNB19M (MGMT+) | 470.0 | 322.0, 71.7 | 359.0, 131.5, 199.5, 96.8 | 328.0, 68.3, 163.0, 245.0 | 282.4, 232.2 | 31.5, 89.0 |
| 3 | Glioma U373V (MGMT low) | 68.0 | 596.0, 154.1 | 650.0, 31.7, 113.4, 75.7 | 561.0, 30.3, 167.4, 245.9 | 197.0, 259.0 | 55.4, 199.0 |
| 4 | Glioma U373M (MGMT+) | 368.7 | 291, 103.2 | 266.0, 41.3, 81.2 39.7 | 409.0, 40.0, 122.3, 269.4 | 301.2, 224.2 | 39.7, 141.0 |
| 5 | Colon HCT116 (MMR mutated) | 590.6 | — | 393.2 | 309.3, 279.9 | — | 70.9, 55.6 |
| 6 | Colon HT29 (MMR proficient) | 639.7 | — | 128.3 | 344.6 | — | 27.2 |
| 7 | Colon DLD1 | 435.3 | — | — | — | — | 45.4 |
| 8 | Melanoma SKMEL-28 (MMR proficient) | 431.0 | — | 293.2 | 422.4 | — | 53.4 |
| 9 | Breast MCF-7 (MMR proficient) | 383.0 | — | — | 315.6 | — | — |
| 10 | Glioma SNB19VR (MGMT−) (TMZ resistant) | 280.2 | — | — | — | — | 50.1, 52.5 |
| 11 | Glioma U373VR (MGMT low) (TMZ resistant) | 288.8 | — | — | — | — | 55.6, 21.6 |
| 12 | Normal Human Fetal Lung Fibroblast MRC-5 | 449.4 | — | — | — | — | 60.3, 55.5 |

TABLE 3

Aryl-Alkyl Compounds

| # | Cell Line | TMZ GI50 (µM) | BB-001 GI50 (µM) | BB-002 GI50 (µM) | BB-003 GI50 (µM) | BB-004 GI50 (µM) | BB-005 GI50 (µM) |
|---|---|---|---|---|---|---|---|
| 1 | Glioma SNB19V (MGMT−) | 35.7 | 33.6, 31.8 | 35.3, 34.1 | 55.8, 93.7 | 52.4, 65.8 | 42.0, 80.2, 81.0, 70.2, |
| 2 | Glioma SNB19M (MGMT+) | 470.0 | 46.1, 53.4 | 41.2, 49.7 | 72.3, 97.1 | 48.4, 60.0 | 41.3, 71.2, 81.7, 90.9 |
| 3 | Glioma U373V (MGMT low) | 68.0 | 49.0, 71.3 | 61.6, 70.7 | 71.0, 138.4 | 84.3, 72.8 | 27.6, 156.7, 72.3, 99.9 |

TABLE 3-continued

Aryl-Alkyl Compounds

| # | Cell Line | TMZ GI50 (μM) | BB-001 GI50 (μM) | BB-002 GI50 (μM) | BB-003 GI50 (μM) | BB-004 GI50 (μM) | BB-005 GI50 (μM) |
|---|---|---|---|---|---|---|---|
| 4 | Glioma U373M (MGMT+) | 368.7 | 67.1, 79.6 | 69.6 95.0 | 73.3, 193.4 | 63.1, 99.4 | 10.3, 211, 366.0, 90.0 |
| 5 | Colon HCT116 (MMR mutated) | 590.6 | 151.2, 193.5 | 205.8 | — | — | — |
| 6 | Colon HT29 (MMR proficient) | 639.7 | 287.8, 43.5 | 243.2 | — | — | — |
| 7 | Colon DLD1 | 435.3 | 80.6 | — | — | — | — |
| 8 | Melanoma SKMEL-28 (MMR proficient) | 431.0 | 297.8, 98.3 | 221.6 | — | — | — |
| 9 | Breast MCF-7 (MMR proficient) | 383.0 | — | — | — | — | — |
| 10 | Glioma SNB19VR (MGMT−) (TMZ resistant) | 280.2 | 46.6 | — | — | 29.1 | — |
| 11 | Glioma U373VR (MGMT low) (TMZ resistant) | 288.8 | 63.7 | — | — | 35.8 | — |
| 12 | Normal Human Fetal Lung Fibroblast MRC-5 | 449.4 | 173.6 | — | — | 189.0 | — |

TABLE 4

Aryl-Alkyl Compounds

| # | Cell Line | TMZ GI50 (μM) | CC-001 GI50 (μM) | CC-002 GI50 (μM) | CC-003 GI50 (μM) | CC-004 GI50 (μM) | CC-005 GI50 (μM) |
|---|---|---|---|---|---|---|---|
| 1 | Glioma SNB19V (MGMT−) | 35.7 | 79.6, 117.2 | 76.7, 52.0 | 207.8, 175.8 | 38.0, 54.9 | 357.1, 238.7 |
| 2 | Glioma SNB19M (MGMT+) | 470.0 | 207.5, 135.2 | 63.6, 54.7 | 198.4, 208.5 | 39.8, 110.4 | 257.2, 408.8 |
| 3 | Glioma U373V (MGMT low) | 68.0 | 205.9, 159.5 | 149.1, 81.4 | 149.9, 351.9 | 10.3, 96.0 | 261.3, 399.6 |
| 4 | Glioma U373M (MGMT+) | 368.7 | 198.3, 232.1 | 96.8, 52.2 | 196.3, 390.8 | 29.3 | 333.5, 330.2 |
| 5 | Colon HCT116 (MMR mutated) | 590.6 | — | — | — | — | — |
| 6 | Colon HT29 (MMR proficient) | 639.7 | — | — | — | — | — |
| 7 | Colon DLD1 | 435.3 | — | — | — | — | — |
| 8 | Melanoma SKMEL-28 (MMR proficient) | 431.0 | — | — | — | — | — |
| 9 | Breast MCF-7 (MMR proficient) | 383.0 | — | — | — | — | — |
| 10 | Glioma SNB19VR (MGMT−) (TMZ resistant) | 280.2 | — | — | — | — | — |
| 11 | Glioma U373VR (MGMT low) (TMZ resistant) | 288.8 | — | — | — | — | — |
| 12 | Normal Human Fetal Lung Fibroblast MRC-5 | 449.4 | — | — | — | — | — |

TABLE 5

Aryl-Alkyl Compounds

| # | Cell Line | TMZ GI50 (μM) | DD-001 GI50 (μM) |
|---|---|---|---|
| 1 | Glioma SNB19V (MGMT−) | 35.7 | 77.0, 127.7, 91.1 |
| 2 | Glioma SNB19M (MGMT+) | 470.0 | 95.0, 70.2, 92.6 |

TABLE 5-continued

Aryl-Alkyl Compounds

| # | Cell Line | TMZ GI50 (μM) | DD-001 GI50 (μM) |
|---|---|---|---|
| 3 | Glioma U373V (MGMT low) | 68.0 | 215.0, 37.5, 91.6 |
| 4 | Glioma U373M (MGMT+) | 368.7 | 125.0, 49.6, 98.7 |
| 5 | Colon HCT116 (MMR mutated) | 590.6 | 301.5 |
| 6 | Colon HT29 (MMR proficient) | 639.7 | 498.4 |
| 7 | Colon DLD1 | 435.3 | 385.4 |
| 8 | Melanoma SKMEL-28 (MMR proficient) | 431.0 | 423.5 |
| 9 | Breast MCF-7 (MMR proficient) | 383.0 | — |
| 10 | Glioma SNB19VR (MGMT−) (TMZ resistant) | 280.2 | — |
| 11 | Glioma U373VR (MGMT low) (TMZ resistant) | 288.8 | — |
| 12 | Normal Human Fetal Lung Fibroblast MRC-5 | 449.4 | — |

TABLE 6

Alkynyl Compounds

| # | Cell Line | TMZ GI50 (μM) | EE-001 GI50 (μM) | EE-002 GI50 (μM) | EE-003 GI50 (μM) |
|---|---|---|---|---|---|
| 1 | Glioma SNB19V (MGMT−) | 35.7 | 40.4, 53.3, 21.7, 26.9 | 33.5, 45.8 | 41.7, 36.6 |
| 2 | Glioma SNB19M (MGMT+) | 470.0 | 41.6, 52.1, 26.9, 30.6 | 38.1, 37.1 | 42.9, 35.2 |
| 3 | Glioma U373V (MGMT low) | 68.0 | 39.6, 51.0, 23.4, 36.3 | 42.1, 31.1 | 26.8, 33.6 |
| 4 | Glioma U373M (MGMT+) | 368.7 | 45.1, 42.8, 24.6, 31.7 | 41.1, 25.1 | 31.5, 30.0 |
| 5 | Colon HCT116 (MMR mutated) | 590.6 | 59.9 | — | — |
| 6 | Colon HT29 (MMR proficient) | 639.7 | 21.1 | — | — |
| 7 | Colon DLD1 | 435.3 | 29.9 | — | — |
| 8 | Melanoma SKMEL-28 (MMR proficient) | 431.0 | 48.5 | — | — |
| 9 | Breast MCF-7 (MMR proficient) | 383.0 | — | — | — |
| 10 | Glioma SNB19VR (MGMT−) (TMZ resistant) | 280.2 | 54.9 | — | — |
| 11 | Glioma U373VR (MGMT low) (TMZ resistant) | 288.8 | 40.3 | — | — |
| 12 | Normal Human Fetal Lung Fibroblast MRC-5 | 449.4 | 56.1, 66.6 | — | — |

TABLE 7

Cyclic-Alkyl Compounds

| # | Cell Line | TMZ GI50 (μM) | FF-001 GI50 (μM) | FF-002 GI50 (μM) | GG-001 GI50 (μM) | GG-002 GI50 (μM) | GG-003 GI50 (μM) | HH-001 GI50 (μM) |
|---|---|---|---|---|---|---|---|---|
| 1 | Glioma SNB19V (MGMT−) | 35.7 | 318.0, 266.5 | 516.0, 375.7, 392.3 | >1000, 379.5 | 888.2, 750.6 | 170.3, 402.7 | 167.0, 189.6 |
| 2 | Glioma SNB19M (MGMT+) | 470.0 | 292.0, 238.1 | 637.0, 418.3, 593.4 | 831.0, 444.9 | 796.2, 602.5 | 152.1, 292.6 | 193.0, 82.7 |
| 3 | Glioma U373V (MGMT low) | 68.0 | 169.0, 163.3 | 293.0, 385.6, 240.6 | 717.0, >1000 | 790.1, >1000 | 386.1 | 39.0, 91.2 |
| 4 | Glioma U373M (MGMT+) | 368.7 | 228.0, 203.6 | 369.0, 345.5, 366.7 | 900.0, 373.5 | 642.5, 727.5 | 57.5, 237.7 | 72.0, 115.1 |
| 5 | Colon HCT116 (MMR mutated) | 590.6 | — | — | — | — | — | — |
| 6 | Colon HT29 (MMR proficient) | 639.7 | — | — | — | — | — | — |
| 7 | Colon DLD1 | 435.3 | — | — | — | — | — | — |
| 8 | Melanoma SKMEL-28 (MMR proficient) | 431.0 | — | — | — | — | — | — |
| 9 | Breast MCF-7 (MMR proficient) | 383.0 | — | — | — | — | — | — |
| 10 | Glioma SNB19VR (MGMT−) (TMZ resistant) | 280.2 | — | — | — | — | — | — |
| 11 | Glioma U373VR (MGMT low) (TMZ resistant) | 288.8 | — | — | — | — | — | — |
| 12 | Normal Human Fetal Lung Fibroblast MRC-5 | 449.4 | — | — | — | — | — | — |

TABLE 8

Amide-Substituted Alkyl Compounds

| # | Cell Line | TMZ GI50 (μM) | JJ-001 GI50 (μM) | JJ-002 GI50 (μM) | JJ-003 GI50 (μM) | JJ-004 GI50 (μM) | JJ-005 GI50 (μM) |
|---|---|---|---|---|---|---|---|
| 1 | Glioma SNB19V (MGMT−) | 35.7 | 37.5, 38.5 | 73.5, 58.1 | 73.6, 61.8 | 348.0, 293.8 | 70.3, 52.4 |
| 2 | Glioma SNB19M (MGMT+) | 470.0 | 107.4, 83.2 | 257.5, 234.8 | 78.6, 68.1 | 417.0, 280.6 | 119.1, 84.9 |
| 3 | Glioma U373V (MGMT low) | 68.0 | 56.2, 74.6 | 234.1, 287.2 | 92.4, 77.8 | 276.0, 94.6 | 195.1, 290.7 |
| 4 | Glioma U373M (MGMT+) | 368.7 | 86.7, 58.0 | 305.6, 221.0 | 98.6, 86.4 | 620.0, 49.2 | 90.4, 173.4 |
| 5 | Colon HCT116 (MMR mutated) | 590.6 | — | — | — | — | — |
| 6 | Colon HT29 (MMR proficient) | 639.7 | — | — | — | — | — |
| 7 | Colon DLD1 | 435.3 | — | — | — | — | — |
| 8 | Melanoma SKMEL-28 (MMR proficient) | 431.0 | — | — | — | — | — |
| 9 | Breast MCF-7 (MMR proficient) | 383.0 | — | — | — | — | — |
| 10 | Glioma SNB19VR (MGMT−) (TMZ resistant) | 280.2 | — | — | — | — | — |
| 11 | Glioma U373VR (MGMT low) (TMZ resistant) | 288.8 | — | — | — | — | — |
| 12 | Normal Human Fetal Lung Fibroblast MRC-5 | 449.4 | — | — | — | — | — |

TABLE 9

Thiol-Substituted Alkyl Compounds

| # | Cell Line | TMZ GI50 (μM) | KK-001 GI50 (μM) | KK-002 GI50 (μM) |
|---|---|---|---|---|
| 1 | Glioma SNB19V (MGMT−) | 35.7 | 118.0, 96.5 | 288.1, 320.8 |
| 2 | Glioma SNB19M (MGMT+) | 470.0 | 202.0, 100.0 | 258.9, 304.5 |
| 3 | Glioma U373V (MGMT low) | 68.0 | 45.0, 73.4 | 152.5, 299.7 |
| 4 | Glioma U373M (MGMT+) | 368.7 | 59.0, 54.0 | 228.7, 285.9 |
| 5 | Colon HCT116 (MMR mutated) | 590.6 | — | — |
| 6 | Colon HT29 (MMR proficient) | 639.7 | — | — |
| 7 | Colon DLD1 | 435.3 | — | — |
| 8 | Melanoma SKMEL-28 (MMR proficient) | 431.0 | — | — |
| 9 | Breast MCF-7 (MMR proficient) | 383.0 | — | — |
| 10 | Glioma SNB19VR (MGMT−) (TMZ resistant) | 280.2 | — | — |
| 11 | Glioma U373VR (MGMT low) (TMZ resistant) | 288.8 | — | — |
| 12 | Normal Human Fetal Lung Fibroblast MRC-5 | 449.4 | — | — |

TABLE 10

Carboxylic Acid-Substituted Alkyl Compounds

| # | Cell Line | TMZ GI50 (μM) | LL-001 GI50 (μM) | LL-002 GI50 (μM) | LL-003 GI50 (μM) | LL-004 GI50 (μM) | LL-005 GI50 (μM) | LL-006 GI50 (μM) | PX-016 GI50 (μM) |
|---|---|---|---|---|---|---|---|---|---|
| 1 | Glioma SNB19V (MGMT−) | 35.7 | 356.0, 355.2 | 447.0, 287.8 | 21.3, 29.7 | 47.2, 35.9, 51.9, | 56.6, 40.1 | 7.9, 53.7 | 55.2, 48.7, 57.3, 48.4 |
| 2 | Glioma SNB19M (MGMT+) | 470.0 | 397.0, 232.0 | 248.0, 261.4 | 34.8, 33.5 | 8.6, 36.6, 38.8, | 46.0, 34.7 | 60.5, 87.2, 64.0 | 61.7, 61.8, 66.7, 54.0 |
| 3 | Glioma U373V (MGMT low) | 68.0 | 234.0, 248.0 | 77.0, 181.2 | 9.6, 11.6 | 7.4, 23.8, 8.3, | 15.7, 8.0 | 70.1, 133.8, 63.3 | 49.9, 59.6, 73.9, 69.5 |
| 4 | Glioma U373M (MGMT+) | 368.7 | 236.0, 280.9 | 156.0, 130.9 | 25.4, 33.7 | 8.3, 38.3, 40.0, | 45.6, 33.3 | 105.4, 275.4, 210.4 | 49.6, 62.5, 54.7 |
| 5 | Colon HCT116 (MMR mutated) | 590.6 | — | — | — | — | — | — | 65.2, 66.0 |
| 6 | Colon HT29 (MMR proficient) | 639.7 | — | — | — | — | — | — | 71.6, 26.2 |
| 7 | Colon DLD1 | 435.3 | — | — | — | — | — | — | 61.1 |
| 8 | Melanoma SKMEL-28 (MMR proficient) | 431.0 | — | — | — | — | — | — | 92.8, 91.3 |

TABLE 10-continued

Carboxylic Acid-Substituted Alkyl Compounds

| # | Cell Line | TMZ GI50 (μM) | LL-001 GI50 (μM) | LL-002 GI50 (μM) | LL-003 GI50 (μM) | LL-004 GI50 (μM) | LL-005 GI50 (μM) | LL-006 GI50 (μM) | PX-016 GI50 (μM) |
|---|---|---|---|---|---|---|---|---|---|
| 9 | Breast MCF-7 (MMR proficient) | 383.0 | — | — | — | — | — | — | — |
| 10 | Glioma SNB19VR (MGMT−) (TMZ resistant) | 280.2 | — | — | — | — | — | — | 37.6, 62.0 |
| 11 | Glioma U373VR (MGMT low) (TMZ resistant) | 288.8 | — | — | — | — | — | — | 57.5, 71.1 |
| 12 | Normal Human Fetal Lung Fibroblast MRC-5 | 449.4 | — | — | — | — | — | — | 108.8, 197.1 |

TABLE 11

Oxy-Alkyl Compounds

| # | Cell Line | TMZ (μM) | NN-001 GI50 (μM) | NN-002 GI50 (μM) | PX-020 GI50 (μM) | PX-021 GI50 (μM) |
|---|---|---|---|---|---|---|
| 1 | Glioma SNB19V (MGMT−) | 35.7 | 128.3, 97.0 | 199.7, 209.6 | 21.0, 42.9, 29.7, 29.6 | 36.0, 26.9, 26.8 |
| 2 | Glioma SNB19M (MGMT+) | 470.0 | 182.2, 262.8 | 395.9, 437.2 | 26.6, 43.4, 28.7 | 29.1, 26.7, 26.7 |
| 3 | Glioma U373V (MGMT low) | 68.0 | 172.2, 228.7 | 208.7, 367.7 | 21.3, 22.0, 30.2, 30.4 | 28.2, 22.3, 25.5 |
| 4 | Glioma U373M (MGMT+) | 368.7 | 98.2, 68.3 | 247.6, 398.1 | 26.5, 39.6 | 27.2, 23.6, 21.9 |
| 5 | Colon HCT116 (MMR mutated) | 590.6 | — | — | 57.4, 47.4, 52.4, 56.1, 29.5 | 33.6, 39.8, 36.6, 40.1 |
| 6 | Colon HT29 (MMR proficient) | 639.7 | — | — | 59.4, 49.8 | 58.5, 55.8 |
| 7 | Colon DLD1 | 435.3 | — | — | 55.4 | 53.7 |
| 8 | Melanoma SKMEL-28 (MMR proficient) | 431.0 | — | — | 56.1, 55.1 | 47.1, 56.8 |
| 9 | Breast MCF-7 (MMR proficient) | 383.0 | — | — | 33.4 | 30.3 |
| 10 | Glioma SNB19VR (MGMT−) (TMZ resistant) | 280.2 | — | — | 25.8, 28.9, 27.8, 29.2, 16.8 | 7.7, 109.7 |
| 11 | Glioma U373VR (MGMT low) (TMZ resistant) | 288.8 | — | — | 33.6, 17.9, 32.4, 55.8, 23.3 | 16.1, 165.5 |
| 12 | Normal Human Fetal Lung Fibroblast MRC-5 | 449.4 | — | — | 61.6, 51.5, 74.1 | 48.6, 65.4 |

TABLE 12

Unsubstituted Alkyl Compounds

| # | Cell Line | TMZ GI50 (μM) | PP-001 GI50 (μM) |
|---|---|---|---|
| 1 | Glioma SNB19V (MGMT−) | 35.7 | >1000, >1000 |
| 2 | Glioma SNB19M (MGMT+) | 470.0 | >1000, 753.1 |
| 3 | Glioma U373V (MGMT low) | 68.0 | 387.0, 580.4 |
| 4 | Glioma U373M (MGMT+) | 368.7 | 427.0, 656.6 |
| 5 | Colon HCT116 (MMR mutated) | 590.6 | — |
| 6 | Colon HT29 (MMR proficient) | 639.7 | — |
| 7 | Colon DLD1 | 435.3 | — |

TABLE 12-continued

Unsubstituted Alkyl Compounds

| # | Cell Line | TMZ GI50 (μM) | PP-001 GI50 (μM) |
|---|---|---|---|
| 8 | Melanoma SKMEL-28 (MMR proficient) | 431.0 | — |
| 9 | Breast MCF-7 (MMR proficient) | 383.0 | — |
| 10 | Glioma SNB19VR (MGMT−) (TMZ resistant) | 280.2 | — |
| 11 | Glioma U373VR (MGMT low) (TMZ resistant) | 288.8 | — |
| 12 | Normal Human Fetal Lung Fibroblast MRC-5 | 449.4 | — |

TABLE 13

Halo-Alkyl Compounds

| # | Cell Line | TMZ GI50 (μM) | PX-030 GI50 (μM) |
|---|---|---|---|
| 1 | Glioma SNB19V (MGMT−) | 35.7 | 44.6, 24.6 |
| 2 | Glioma SNB19M (MGMT+) | 470.0 | 36.6, 25.4 |
| 3 | Glioma U373V (MGMT low) | 68.0 | 34.8, 23.8 |
| 4 | Glioma U373M (MGMT+) | 368.7 | 23.7, 25.1 |
| 5 | Colon HCT116 (MMR mutated) | 590.6 | 22.3 |
| 6 | Colon HT29 (MMR proficient) | 639.7 | — |
| 7 | Colon DLD1 | 435.3 | — |
| 8 | Melanoma SKMEL-28 (MMR proficient) | 431.0 | — |
| 9 | Breast MCF-7 (MMR proficient) | 383.0 | — |
| 10 | Glioma SNB19VR (MGMT−) (TMZ resistant) | 280.2 | 8.0, 42.9 |
| 11 | Glioma U373VR (MGMT low) (TMZ resistant) | 288.8 | 28.9, 34.5 |
| 12 | Normal Human Fetal Lung Fibroblast MRC-5 | 449.4 | 50.9, 67.2 |

TABLE 14

| # | Compound | Glioma SNB19V (MGMT−) GI50 (μM) | Glioma SNB19M (MGMT+) GI50 (μM) |
|---|---|---|---|
| 1 | Temozolomide | 32.2 | 875.0, 834.3 |
| 2 | BB-001 | 22.2 | 8.5 |
| 3 | EE-001 | 7.0 | 7.8 |
| 4 | PX-020 | 38.6 | 30 |
| 5 | PX-021 | 43.3 | 22.1 |
| 6 | PX-030 | 38.9 | 31.5 |

TABLE 15

Sulfonyl-Alkyl Compounds

| # | Cell Line | TMZ GI50 (μM) | UU-001 GI50 (μM) | UU-002 GI50 (μM) | UU-003 GI50 (μM) |
|---|---|---|---|---|---|
| 1 | Glioma SNB19V (MGMT−) | 35.7 | 92.4, 154.3 | 6.9, 13.9, 20.6 | 30.3, 38.1, 25.3, 21.8 |
| 2 | Glioma SNB19M (MGMT+) | 470.0 | 73.1, 180.9 | 13.7, 26.6, 14.5 | 8.4, 8.5, 19.6, 20.8 |
| 3 | Glioma U373V (MGMT low) | 68.0 | 42.6, 90.3 | 35.9, 4.5 | 6.8, 8.6, 4.3, 13.0 |
| 4 | Glioma U373M (MGMT+) | 368.7 | 35.8, 160.2 | 9.7, 8.5, 4.2 | 4.6, 8.6, 7.6, 8.2 |
| 5 | Colon HCT116 (MMR mutated) | 590.6 | — | — | 6.7, 5.3, 5.0 |
| 6 | Colon HT29 (MMR proficient) | 639.7 | — | — | — |
| 7 | Colon DLD1 | 435.3 | — | — | 8.2, 8.2, 9.3 |
| 8 | Melanoma SKMEL-28 (MMR proficient) | 431.0 | — | — | — |
| 9 | Breast MCF-7 (MMR proficient) | 383.0 | — | — | — |
| 10 | Glioma SNB19VR (MGMT−) (TMZ resistant) | 280.2 | — | — | 6.8, 3.9, 20.9 |
| 11 | Glioma U373VR (MGMT low) (TMZ resistant) | 288.8 | — | — | 3.4, 9.1, 5.5 |
| 12 | Normal Human Fetal Lung Fibroblast MRC-5 | 449.4 | — | — | 56.8, 55.2, 52.1 |

TABLE 16

Phosphate-Alkyl Compounds

| # | Cell Line | TMZ GI50 (μM) | VV-001 GI50 (μM) |
|---|---|---|---|
| 1 | Glioma SNB19V (MGMT−) | 35.7 | 73.6, 63.4 |
| 2 | Glioma SNB19M (MGMT+) | 470.0 | 85.6, 102.3 |
| 3 | Glioma U373V (MGMT low) | 68.0 | 305.5, 173.5 |
| 4 | Glioma U373M (MGMT+) | 368.7 | 683.9, 312.0 |
| 5 | Colon HCT116 (MMR mutated) | 590.6 | — |
| 6 | Colon HT29 (MMR proficient) | 639.7 | — |

TABLE 16-continued

Phosphate-Alkyl Compounds

| # | Cell Line | TMZ GI50 (μM) | VV-001 GI50 (μM) |
|---|---|---|---|
| 7 | Colon DLD1 | 435.3 | — |
| 8 | Melanoma SKMEL-28 (MMR proficient) | 431.0 | — |
| 9 | Breast MCF-7 (MMR proficient) | 383.0 | — |
| 10 | Glioma SNB19VR (MGMT−) (TMZ resistant) | 280.2 | — |
| 11 | Glioma U373VR (MGMT low) (TMZ resistant) | 288.8 | — |
| 12 | Normal Human Fetal Lung Fibroblast MRC-5 | 449.4 | — |

TABLE 17

Carbamate-Alkyl Compounds

| # | Cell Line | TMZ GI50 (μM) | WW-001 GI50 (μM) |
|---|---|---|---|
| 1 | Glioma SNB19V (MGMT−) | 35.7 | 64.8, 67.8 |
| 2 | Glioma SNB19M (MGMT+) | 470.0 | 56.0, 71.2 |
| 3 | Glioma U373V (MGMT low) | 68.0 | 35.8, 60.1 |
| 4 | Glioma U373M (MGMT+) | 368.7 | 50.0, 62.5 |
| 5 | Colon HCT116 (MMR mutated) | 590.6 | — |
| 6 | Colon HT29 (MMR proficient) | 639.7 | — |
| 7 | Colon DLD1 | 435.3 | — |
| 8 | Melanoma SKMEL-28 (MMR proficient) | 431.0 | — |
| 9 | Breast MCF-7 (MMR proficient) | 383.0 | — |
| 10 | Glioma SNB19VR (MGMT−) (TMZ resistant) | 280.2 | — |
| 11 | Glioma U373VR (MGMT low) (TMZ resistant) | 288.8 | — |
| 12 | Normal Human Fetal Lung Fibroblast MRC-5 | 449.4 | — |

TABLE 18

Oxime-Alkyl Compounds

| # | Cell Line | TMZ GI50 (μM) | XX-001 GI50 (μM) |
|---|---|---|---|
| 1 | Glioma SNB19V (MGMT−) | 35.7 | 51.7, 9.9 |
| 2 | Glioma SNB19M (MGMT+) | 470.0 | 47.9, 47.2 |
| 3 | Glioma U373V (MGMT low) | 68.0 | 18.5, 10.6 |
| 4 | Glioma U373M (MGMT+) | 368.7 | 40.9, 7.4 |
| 5 | Colon HCT116 (MMR mutated) | 590.6 | — |
| 6 | Colon HT29 (MMR proficient) | 639.7 | — |
| 7 | Colon DLD1 | 435.3 | — |
| 8 | Melanoma SKMEL-28 (MMR proficient) | 431.0 | — |
| 9 | Breast MCF-7 (MMR proficient) | 383.0 | — |
| 10 | Glioma SNB19VR (MGMT−) (TMZ resistant) | 280.2 | — |
| 11 | Glioma U373VR (MGMT low) (TMZ resistant) | 288.8 | — |
| 12 | Normal Human Fetal Lung Fibroblast MRC-5 | 449.4 | — |

As shown by the data in Table 1 (above), Temozolomide (TMZ) is demonstrably more active in the glioma lines which are MGMT− (SNB 19V and U373V) than those which express MGMT (MGMT+ lines SNB 19M and U373M). Activity of TMZ against a range of other cell lines is weak (GI50 values 200-700 micromolar) probably because these lines express high levels of MGMT.

As shown by the data in Table 2 (above), these compounds are less active than TMZ in the MGMT− glioma lines and approx equiactive in the MGMT+ lines.

As shown by the data in Table 3 (above), Compounds BB-001 through BB-005 are approximately as active as TMZ in the MGMT− lines, but are more potent in the MGMT+ lines.

As shown by the data in Table 6 (above), Compound EE-001 is more potent than TMZ in the glioma MGMT− and MGMT+ lines as well as other lines (e.g., colon, melanoma). Compound EE-001 is a particularly efficacious compound, independent of the MGMT repair status of cell line.

As shown by the data in Table 7 (above), these compounds are, in general, less active than TMZ in glioma cell lines.

As shown by the data in Table 8 (above), Compound JJ-001 is the most potent of these compounds with good activity against both MGMT− and MGMT+ glioma cell lines. Substitution on the primary amide group appears to reduces activity (JJ-002 to JJ-005).

As shown by the data in Table 9 (above), Compound KK-001 is more active than TMZ against the MGMT+ cell lines.

As shown by the data in Table 10 (above), the acetic acid ester derivatives LL-003 and PX-016 show surprising efficacy against both glioma MGMT− and MGMT+ cell lines. The corresponding propionic acid ester LL-002 is >10-fold less active.

As shown by the data in Table 11 (above), Compounds PX-020 and PX-021 are surprising efficacious against both glioma MGMT− and MGMT+ cell lines.

As shown in Table 15 (above), the sulfone and sulfoxide compounds UU-001, UU-002 and UU-003 show surprising efficacy against both giomer MGMT− and MGMT+ cell lines and a range of other cell lines (e.g., colon and melanoma). Compounds UU-002 and UU-003 are particularly efficacious compounds, independent of the MGMT repair status of the cell line.

As shown in Table 16 (above), the phosphonate compound VV-001 is surprisingly more active than TMZ against SNB19M and SNB19V glioma cell lines, regardless of MGMT status.

As shown in Table 17 (above), the carbamate compound WW-001 is surprisingly more active than TMZ in MGMT+ variants of the SNB19 and U373 glioma cell lines.

As shown in Table 18 (above), the oxime-alkyl compound XX-001 is surprisingly more active than TMZ in MGMT+ glioma cell lines. This enhanced activity is also observed in the MGMT− glioma cell line U373V.

3TM compounds (as described herein) with -Q as —CH$_2$CO$_2$Me, —CH$_2$CO$_2$Et, —CH$_2$C≡CH, —CH$_2$OMe, or —CH$_2$Cl have activity against tumour cell lines regardless of the MGMT and MMR (Mis-Match Repair) status of the cell line. These compounds are especially preferred.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

The invention claimed is:

1. A compound of the following formula or a salt thereof:

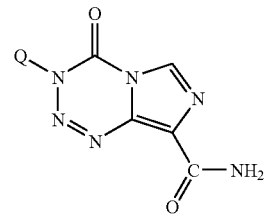

wherein:
(a) -Q is independently a group of the following formula:

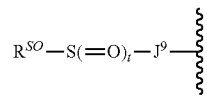

wherein:
-J$^9$- is independently saturated aliphatic C$_{1-4}$alkylene;
t is independently 1 or 2; and
—R$^{SO}$ is independently saturated aliphatic C$_{1-4}$alkyl, phenyl, or benzyl, wherein said phenyl and benzyl are independently optionally substituted with one or more substituents selected from —F, —Cl, —Br, —I, —R$^{SOR}$, —CF$_3$, —OH, —OR$^{SOR}$, and —OCF$_3$, wherein each —R$^{SOR}$ is independently saturated aliphatic C$_{1-4}$alkyl; or (b) -Q is independently a group of the following formula:

wherein —R$^{YNE}$ is independently aliphatic C$_{2-6}$alkynyl, and is optionally substituted; or (c) -Q is independently a group of the following formula:

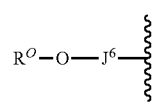

wherein:
-J$^6$- is independently saturated aliphatic C$_{1-4}$alkylene;
—R$^O$ is independently —H or —R$^{OO}$;
—R$^{OO}$ is independently phenyl, benzyl, or —Si(R$^{SI}$)$_3$;
each —R$^{SI}$ is independently saturated aliphatic C$_{1-4}$alkyl; or (d) -Q is independently a group of the following formula:

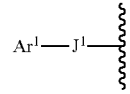

wherein:
—Ar$^1$ is independently C$_{5-6}$heteroaryl, and is optionally substituted;

-J¹- is independently saturated aliphatic $C_{1-4}$alkylene;
with the proviso that -Q is not furan 2 yl methyl; or
(e) -Q is independently a group of the following formula:

$$Cy^2-J^2-\xi$$

wherein:
— $Cy^2$ is independently
  non-aromatic $C_{3-7}$heterocyclyl and is optionally substituted;
-J²- is independently a covalent bond or saturated aliphatic $C_{1-4}$alkylene;
or wherein:
— $Cy^2$ is independently saturated $C_{3-7}$cycloalkyl and is optionally substituted;
-J²- is independently saturated aliphatic $C_{1-4}$alkylene; or
(f) -Q is independently a group of the following formula:

$$\begin{array}{c} R^{N3A} \quad O \\ \diagdown \quad \| \\ N-C-J^3-\xi \\ \diagup \\ R^{N3B} \end{array}$$

wherein:
-J³- is independently saturated aliphatic $C_{1-4}$alkylene; and
either:
— $R^{N3A}$ is independently —H or — $R^{N3C}$;
— $R^{N3B}$ is independently —H or — $R^{N3D}$;
— $R^{N3C}$ is independently saturated aliphatic $C_{1-4}$alkyl;
— $R^{N3D}$ is independently saturated aliphatic $C_{1-4}$alkyl;
or:
— $R^{N3A}$ and — $R^{N3B}$, taken together with the nitrogen atom to which they are attached, form a 4-, 5-, 6-, or 7-membered non-aromatic ring having exactly one ring heteroatom which is nitrogen, or having exactly two ring heteroatoms, which are nitrogen and oxygen, or nitrogen and nitrogen; or
(g) -Q is independently a group of the following formula:

$$R^S-S-J^4-\xi$$

wherein:
-J⁴- is independently saturated aliphatic $C_{1-4}$alkylene; and
— $R^S$ is independently saturated aliphatic $C_{1-4}$alkyl; or
(h) -Q is independently a group selected from groups of the following formulae:

$$R^E-O-\overset{O}{\underset{\|}{C}}-J^5-\xi$$

$$R^F-\overset{O}{\underset{\|}{C}}-O-J^5-\xi$$

wherein:
-J⁵- is independently saturated aliphatic $C_{1-4}$alkylene, and is optionally substituted with one or more substituents independently selected from —OH and —OR$^{EER}$, wherein
each —R$^{EER}$ is independently saturated aliphatic $C_{1-4}$alkyl;
—R$^E$ is independently —H or —R$^{EE}$;
—R$^F$ is independently —R$^{EE}$;
—R$^{EE}$ is independently saturated aliphatic $C_{1-4}$alkyl;
with the proviso that -Q is not —$CH_2C(=O)OH$ or —$CH_2C(=O)OCH_2CH_3$; or
(i) -Q is independently a group of the following formula:

$$R^{AC}-\overset{O}{\underset{\|}{C}}-R^{6A}-\xi$$

wherein:
-$J^{6A}$- is independently saturated aliphatic $C_{1-4}$alkylene; and
—$R^{AC}$ is independently saturated aliphatic $C_{1-4}$alkyl; or
(j) -Q is independently a group of the following formula:

$$O_2N-J^7-\xi$$

wherein -J⁷- is independently saturated aliphatic $C_{1-4}$alkylene; or
(k) -Q is independently a group of the following formula:

$$NC-J^8-\xi$$

wherein -J⁸- is independently saturated aliphatic $C_{1-4}$alkylene; or
(l) -Q is independently a group of the following formula:

$$\begin{array}{c} R^{PR} \\ \diagdown O \\ \quad | \\ O=P-J^{10}-\xi \\ \quad | \\ \diagup O \\ R^{PR} \end{array}$$

wherein:
-$J^{10}$- is independently saturated aliphatic $C_{1-4}$alkylene;
each —R$^{PR}$ is independently saturated aliphatic $C_{1-4}$alkyl, phenyl, or benzyl, wherein said phenyl and benzyl are independently optionally substituted with one or more substituents selected from —F, —Cl, —Br, —I, —R$^{PRR}$, —CF$_3$, —OH, —OR$^{PRR}$, and —OCF$_3$, wherein each —R$^{PRR}$ is independently saturated aliphatic $C_{1-4}$alkyl; or
(m) -Q is independently a group of the following formula:

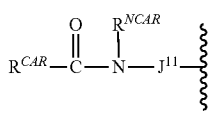

wherein:
-J$^{11}$- is independently saturated aliphatic C$_{1-4}$alkylene; and
—R$^{NCAR}$ is independently —H or —R$^{CAR}$;
each —R$^{CAR}$ is independently saturated aliphatic C$_{1-4}$alkyl, phenyl, benzyl, fluorenyl, or —CH$_2$-fluorenyl, wherein said phenyl, benzyl, and fluorenyl are independently optionally substituted with one or more substituents selected from —F, —Cl, —Br, —I, —R$^{CARR}$, —CF$_3$, —OH, —OR$^{CARR}$, and —OCF$_3$, wherein each —R$^{CARR}$ is independently saturated aliphatic C$_{1-4}$alkyl; or
(n) -Q is independently a group of the following formula:

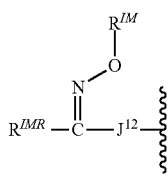

wherein:
-J$^{12}$- is independently saturated aliphatic C$_{1-4}$alkylene; and
—R$^{IM}$ is independently —H or —R$^{IMR}$;
each —R$^{IMR}$ is independently saturated aliphatic C$_{1-4}$alkyl, phenyl, or benzyl, wherein said phenyl and benzyl are independently optionally substituted with one or more substituents selected from —F, —Cl, —Br, —I, —R$^{IMRR}$, —CF$_3$, —OH, —OR$^{IMRR}$, and —OCF$_3$, wherein each —R$^{IMRR}$ is independently saturated aliphatic C$_{1-4}$alkyl.

2. A compound according to claim 1 of the following formula or a salt thereof:

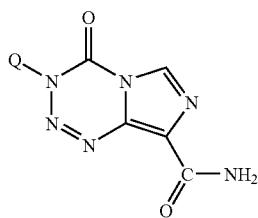

wherein -Q is independently a group of the following formula:

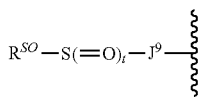

wherein:
-J$^9$- is independently saturated aliphatic C$_{1-4}$alkylene;
t is independently 1 or 2; and —R$^{SO}$ is independently saturated aliphatic C$_{1-4}$alkyl, phenyl, or benzyl, wherein said phenyl and benzyl are independently optionally substituted with one or more substituents selected from —F, —Cl, —Br, —I, —R$^{SOR}$, —CF$_3$, —OH, —OR$^{SOR}$, and —OCF$_3$, wherein each —R$^{SOR}$ is independently saturated aliphatic C$_{1-4}$alkyl.

3. A compound according to claim 2, wherein t is independently 1.

4. A compound according to claim 2, wherein t is independently 2.

5. A compound according to claim 3, wherein -J$^9$- is independently —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, or —CH(CH$_2$CH$_3$)—.

6. A compound according to claim 4, wherein -J$^9$- is independently —CH$_2$—, —CH$_2$CH$_2$—, —CH$_2$CH$_2$CH$_2$—, —CH(CH$_3$)—, —CH(CH$_3$)CH$_2$—, —CH$_2$CH(CH$_3$)—, or —CH(CH$_2$CH$_3$)—.

7. A compound according to claim 3, wherein -J$^9$- is independently —CH$_2$— or —CH$_2$CH$_2$—.

8. A compound according to claim 4, wherein -J$^9$- is independently —CH$_2$— or —CH$_2$CH$_2$—.

9. A compound according to claim 3, wherein —R$^{SO}$ is independently saturated aliphatic C$_{1-4}$alkyl.

10. A compound according to claim 4, wherein —R$^{SO}$ is independently saturated aliphatic C$_{1-4}$alkyl.

11. A compound according to claim 5, wherein —R$^{SO}$ is independently saturated aliphatic C$_{1-4}$alkyl.

12. A compound according to claim 6, wherein —R$^{SO}$ is independently saturated aliphatic C$_{1-4}$alkyl.

13. A compound according to claim 7, wherein —R$^{SO}$ is independently saturated aliphatic C$_{1-4}$alkyl.

14. A compound according to claim 8, wherein —R$^{SO}$ is independently saturated aliphatic C$_{1-4}$alkyl.

15. A compound according to claim 3, wherein —R$^{SO}$ is independently -Me.

16. A compound according to claim 4, wherein —R$^{SO}$ is independently -Me.

17. A compound according to claim 5, wherein —R$^{SO}$ is independently -Me.

18. A compound according to claim 6, wherein —R$^{SO}$ is independently -Me.

19. A compound according to claim 7, wherein —R$^{SO}$ is independently -Me.

20. A compound according to claim 8, wherein —R$^{SO}$ is independently -Me.

21. A compound according to claim 2, selected from the following compounds or a salt thereof:

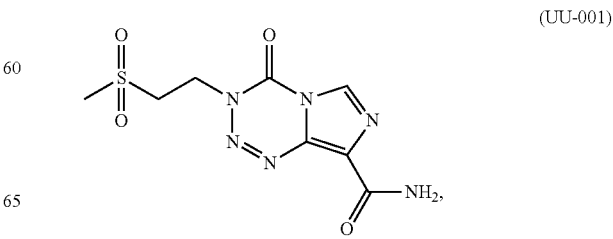

(UU-001)

(UU-002)

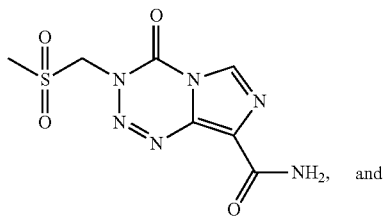

and (UU-003)

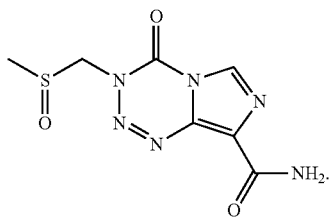

22. A pharmaceutical composition comprising a compound according to claim 1, and a pharmaceutically acceptable carrier or diluent.

23. A method of treatment of glioma comprising administering to a subject in need of treatment a therapeutically-effective amount of a compound according to claim 1.

24. A method for the preparation of a compound of Formula (I):

(I)

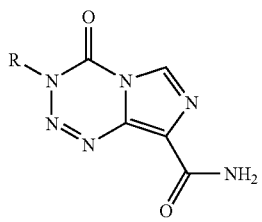

wherein R is independently a group of the following formula:

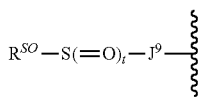

wherein:

-$J^9$- is independently saturated aliphatic $C_{1-4}$alkylene;

t is independently 1 or 2; and

—$R^{SO}$ is independently saturated aliphatic $C_{1-4}$alkyl, phenyl, or benzyl, wherein said phenyl and benzyl are independently optionally substituted with one or more substituents selected from —F, —Cl, —Br, —I, —$R^{SOR}$, —$CF_3$, —OH, —$OR^{SOR}$, and —$OCF_3$, wherein each —$R^{SOR}$ is independently saturated aliphatic $C_{1-4}$alkyl;

comprising the step of reacting a compound of Formula (II) or a salt thereof:

(II)

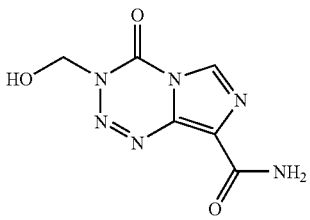

with a compound of the formula $R^{T1}$—$R^{ALK}$—X, wherein:

—X is independently a halogen atom;

—$R^{ALK}$— is independently saturated aliphatic $C_{1-4}$alkylene;

—$R^{T1}$ is independently —S(=O)$R^{T2}$ or —S(=O)$_2R^{T2}$;

each —$R^{T2}$ is independently saturated aliphatic $C_{1-4}$alkyl, phenyl, or benzyl, wherein said phenyl and benzyl are independently optionally substituted with one or more substituents selected from —F, —Cl, —Br, —I, —$R^{SOR}$—$CF_3$, —OH, —$OR^{SOR}$, and —$OCF_3$, wherein each —$R^{SOR}$ is independently saturated aliphatic $C_{1-4}$alkyl; wherein said reaction is performed in the presence of an organic base at a reaction temperature of about 0° C. to about 30° C. for a reaction time of about 1 to about 48 hours;

and further comprising a step of acidifying the reaction mixture resulting from said reaction.

25. A compound of Formula (II) or a salt thereof:

(II)

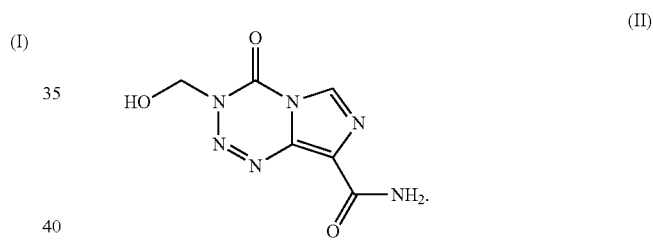

26. A compound according to claim 1 of the following formula or a salt thereof:

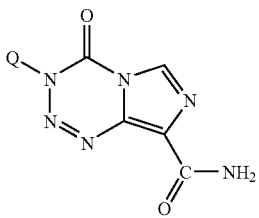

wherein -Q is independently a group of the following formula:

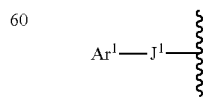

wherein:

—$Ar^1$ is independently $C_{5-6}$heteroaryl, and is optionally substituted;

-J¹- is independently saturated aliphatic $C_{1-4}$alkylene;
with the proviso that -Q is not furan-2-yl-methyl.

27. A compound according to claim 26, wherein -J¹- is independently saturated aliphatic $C_{1-3}$alkylene.

28. A compound according to claim 26, wherein -J¹- is independently —CH₂—, —CH(CH₃)—, or —CH(CH₂CH₃)—.

29. A compound according to claim 26, wherein -J¹- is independently —CH(CH₃)—.

30. A compound according to claim 26, wherein —Ar¹ is independently unsubstituted or substituted with one or more substituents independently selected from: —F, —Cl, —Br, —I, —OH, —OR$^{Z1}$, —SH, —SR$^{Z1}$, —NO₂, —CN, —NH₂, —NHR$^{Z1}$, —NR$^{Z1}$₂, —COOH, —COOR$^{Z1}$, —CONH₂, —CONHR$^{Z1}$, —CONR$^{Z1}$₂, —NHCOOH, —NR$^{Z1}$COOH, —NHCOOR$^{Z1}$, and —NR$^{Z1}$COOR$^{Z1}$, wherein each —R$^{Z1}$ is independently saturated aliphatic $C_{1-4}$alkyl, phenyl, or benzyl, wherein said phenyl and benzyl are independently optionally substituted with one or more substituents selected from —F, —Cl, —Br, —I, —R$^{Z1R}$, —CF₃, —OH, and —OR$^{Z1R}$, wherein each —R$^{Z1R}$ is independently saturated aliphatic $C_{1-4}$alkyl.

31. A compound according to claim 26, wherein —Ar¹ is independently unsubstituted or substituted with one or more substituents independently selected from: —F, —Cl, —Br, and —I.

32. A compound according to claim 26, wherein —Ar¹ is independently unsubstituted.

33. A compound according to claim 1 of the following formula or a salt thereof:

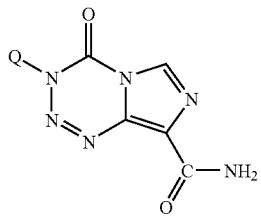

wherein -Q is independently a group of the following formula:

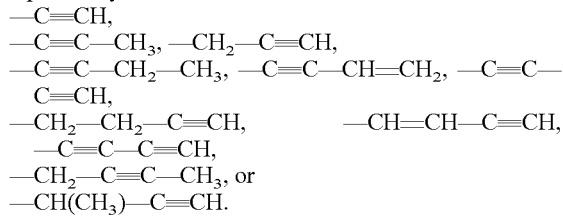

wherein —R$^{YNE}$ is independently aliphatic $C_{2-6}$alkynyl, and is optionally substituted.

34. A compound according to claim 33, wherein —R$^{YNE}$ is independently aliphatic $C_{3-5}$alkynyl, and is optionally substituted.

35. A compound according to claim 33, wherein R$^{YNE}$ is independently unsubstituted or substituted with one or more substituents independently selected from: —F, —Cl, —Br, —I, —OH, —OR$^{Z3}$, —SH, —SR$^{Z3}$, —SiR$^{Z3}$₃, —NO₂, —CN, —NH₂, —NHR$^{Z3}$, —NR$^{Z3}$₂, —COOH, —COOR$^{Z3}$, —CONH₂, —CONHR$^{Z3}$, —CONR$^{Z3}$₂, —NHCOOH, —NR$^{Z3}$COOH, —NHCOOR$^{Z3}$, and —NR$^{Z3}$COOR$^{Z3}$, wherein each R$^{Z3}$ is independently saturated aliphatic $C_{1-4}$alkyl, phenyl, or benzyl, wherein said phenyl and benzyl are independently optionally substituted with one or more substituents selected from —F, —Cl, —Br, —I, —R$^{Z3R}$, —CF₃, —OH, and —OR$^{Z3R}$, wherein each —R$^{Z3R}$ is independently saturated aliphatic $C_{1-4}$alkyl.

36. A compound according to claim 33, wherein —R$^{YNE}$ is independently unsubstituted.

37. A compound according to claim 33, wherein —R$^{YNE}$ is independently:
—C≡CH,
—C≡C—CH₃, —CH₂—C≡CH,
—C≡C—CH₂—CH₃, —C≡C—CH=CH₂, —C≡C—C≡CH,
—CH₂—CH₂—C≡CH,       —CH=CH—C≡CH,
—C≡C—C≡CH,
—CH₂—C≡C—CH₃, or
—CH(CH₃)—C≡CH.

38. A compound according to claim 33, wherein —R$^{YNE}$ is independently —CH₂—C≡CH.

* * * * *